United States Patent
Warren et al.

(10) Patent No.: US 9,903,814 B2
(45) Date of Patent: Feb. 27, 2018

(54) SYSTEMS AND METHODS FOR OPTICALLY COUPLING OPTOELECTRONIC COMPONENTS OF A HAZARD DETECTION SYSTEM TO DETERMINE A SMOKE CONDITION OF AN ENVIRONMENT

(71) Applicant: Google Inc., Mountain View, CA (US)

(72) Inventors: Daniel Adam Warren, San Francisco, CA (US); Ian C. Smith, Mountain View, CA (US); Morakinyo John Aina, Mountain View, CA (US); Andrew W. Goldenson, Palo Alto, CA (US); Dietrich Ho, Mountain View, CA (US); Anurag Gupta, Mountain View, CA (US)

(73) Assignee: GOOGLE LLC, Mountain View, CA (US)

( * ) Notice: Subject to any disclaimer, the term of this patent is extended or adjusted under 35 U.S.C. 154(b) by 146 days.

(21) Appl. No.: 14/986,452

(22) Filed: Dec. 31, 2015

(65) Prior Publication Data
US 2017/0191930 A1     Jul. 6, 2017

(51) Int. Cl.
    *G08B 21/00*    (2006.01)
    *G01N 21/53*    (2006.01)
    (Continued)

(52) U.S. Cl.
    CPC ............... *G01N 21/53* (2013.01); *G01K 7/00* (2013.01); *G01N 2201/062* (2013.01); *G01N 2201/1211* (2013.01); *G08B 17/107* (2013.01)

(58) Field of Classification Search
    CPC .................................................. G01N 21/53
    (Continued)

(56) References Cited

U.S. PATENT DOCUMENTS

| 5,530,433 A | 6/1996 | Morita |
|---|---|---|
| 2005/0057365 A1 | 3/2005 | Qualey |

(Continued)

FOREIGN PATENT DOCUMENTS

| DE | 202015000820 | 3/2015 |
|---|---|---|
| JP | 08-201263 | 8/1996 |

(Continued)

OTHER PUBLICATIONS

Bera et al., "Drive Circuits for Temperature-Invariant Performance of Junction Diodes." Circuits, Devices & Systems, IET, vol. 3, Issue 4, Aug. 2009, http://ieeexploreieee.org/xpl/articleDetailsjsp?tp=&arnumber=5191320&queryText%3Dlight+emitting+diode+temperature+compensation, 2 pages.

(Continued)

*Primary Examiner* — Jeffery Hofsass
(74) *Attorney, Agent, or Firm* — Van Court & Aldridge LLP

(57) ABSTRACT

Apparatus, systems, methods, and related computer program products for handling temperature variation with optoelectronic components of a hazard detection system are described herein. A power characteristic of an optoelectronic component of the hazard detection system may be used to determine a temperature of an environment of the hazard detection system. A power characteristic of an optoelectronic component of the hazard detection system may be used to determine a smoke condition of an environment of the hazard detection system. Optoelectronic components of the hazard detection system may be optically coupled to determine a smoke condition of an environment of the hazard detection system. Multiple optoelectronics of the hazard detection system may be operative to detect forward (Continued)

scatter and back scatter of one or more types of light to determine a characteristic of a hazard particle.

20 Claims, 21 Drawing Sheets

(51) Int. Cl.
*G01K 7/00* (2006.01)
*G08B 17/107* (2006.01)

(58) Field of Classification Search
USPC ......... 340/628, 630; 356/337, 338, 340, 341
See application file for complete search history.

(56) References Cited

U.S. PATENT DOCUMENTS

| | | | |
|---|---|---|---|
| 2006/0017580 | A1 | 1/2006 | Hess et al. |
| 2011/0194111 | A1* | 8/2011 | Dohi .................. G01N 21/53 356/340 |
| 2015/0170490 | A1 | 6/2015 | Shaw |

FOREIGN PATENT DOCUMENTS

| | | |
|---|---|---|
| JP | 2008-242627 | 10/2008 |
| JP | 2013-109751 | 6/2013 |
| WO | 00-07161 | 2/2000 |

OTHER PUBLICATIONS

Bera et al., "Temperature Behavior and Compensation of Light-Emitting Diode." Photonics Technology Letters, IEEE, vol. 17, Issue 11, Nov. 2005, http://ieeexplore.ieee.org/xpl/articleDetails.jsp?reload=true&tp=&arnumber=1522295&queryText%3Dlight+emitting+diode+temperature+compensation, 2 pages.

Chhajed et al., "Junction Temperature in Light-Emitting Diodes Assessed by Different Methods." Integrated Optoelectronic Devices 2005, International Society for Optics and Photonics, 2005, www.ka-electronics.com/images/pdf/Junction_Temperature_LED_Tempco.pdf.

Chonko, "Use Forward Voltage Drop to Measure Junction Temperature." Electronic Design, 8 pages, Dec. 15, 2005, http://electronicdesign.com/lighting/use-forward-voltage-drop-measure-junction-temperature.

Karha et al., "Relationships Between Junction Temperature, Forward Voltage and Spectrum of LEDs." Apr. 6, 2013, pp. 1-14, http://www.m4ssl.npl.co.uk/wp-content/uploads/2013/01/Petri-Kaha-RELATIONSHIPS-BETWEEN-JUNCTION-TEMPERATURE.pdf.

Mroczka et al., "Methods of Temperature Stabilization of Light-Emitting Diode Radiation." Rev. Sci. Instrum. 65, 803 (1994), http://dx.doi.org/10.1063/1.1144904, 2 pages.

Shane, "Taos TSL230R Light Sensor C Tutorial." Feb. 8, 2012, 25 pages, http://www.expertcore.org/viewtopic.php?f=92&t=3073&p=9452&hilit.

Zabiliute, "Temperature Characteristics of LEDs." 2013, pp. 1-10, http://web.vu.lt/tmi/a.zabiliute/wp-content/uploads/sites/2/2013/11/LED_Temperature_characterstics.pdf.

"TSL230RD, TSL230ARD, TSL230BRD Programmable Light-to-Frequency Converters." ams AG datasheet, Oct. 2007, 15 pages.

"What Are Some Methods to Achieve Constant LED Brightness Over Large Temperature Ranges?" May 6, 2012, 3 pages, http://electronics.stackexchange.com/questions/32647/what-are-some-methods-to-achieve-constant-led-brightness-over-large-temperature.

"Simple 90V, 25mA, Temperature Compensated, Constant Current, LED Driver IC." Supertex Inc., 2011, 6 pages.

* cited by examiner

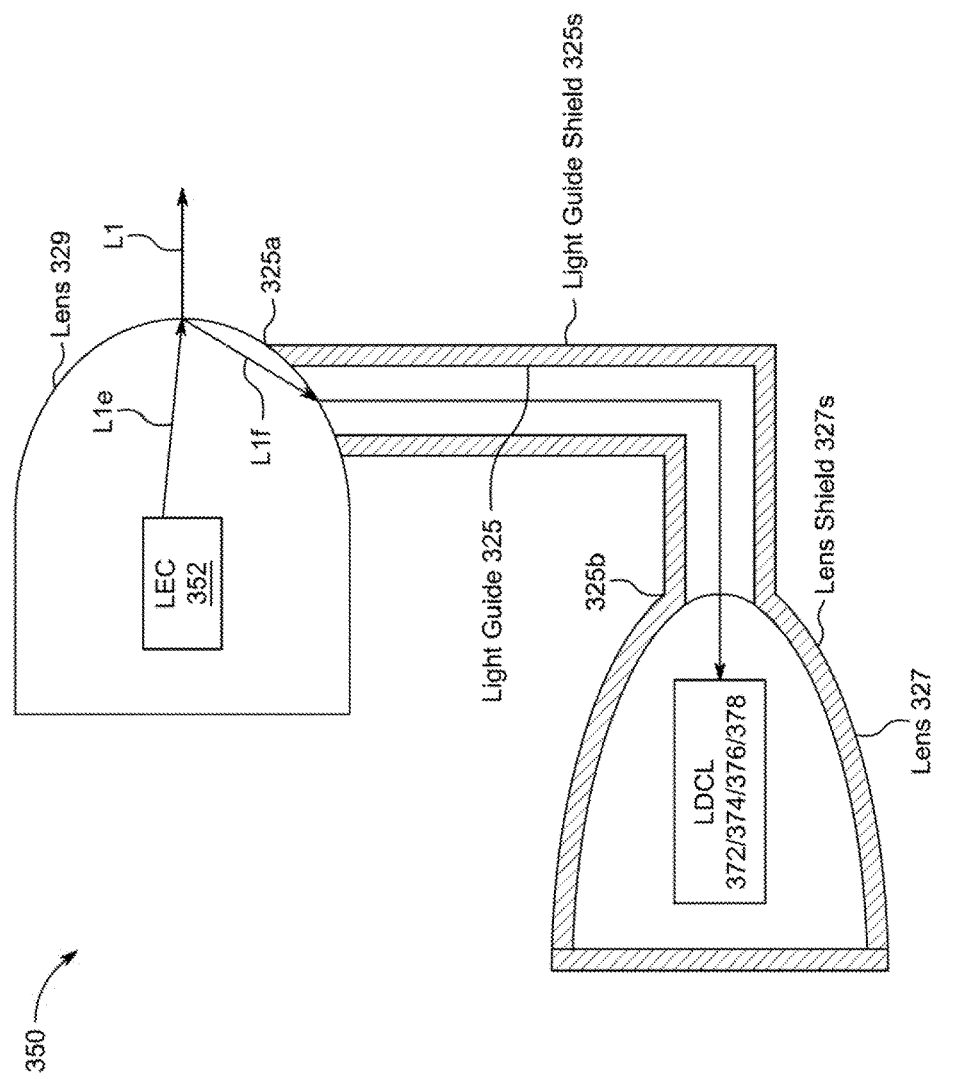

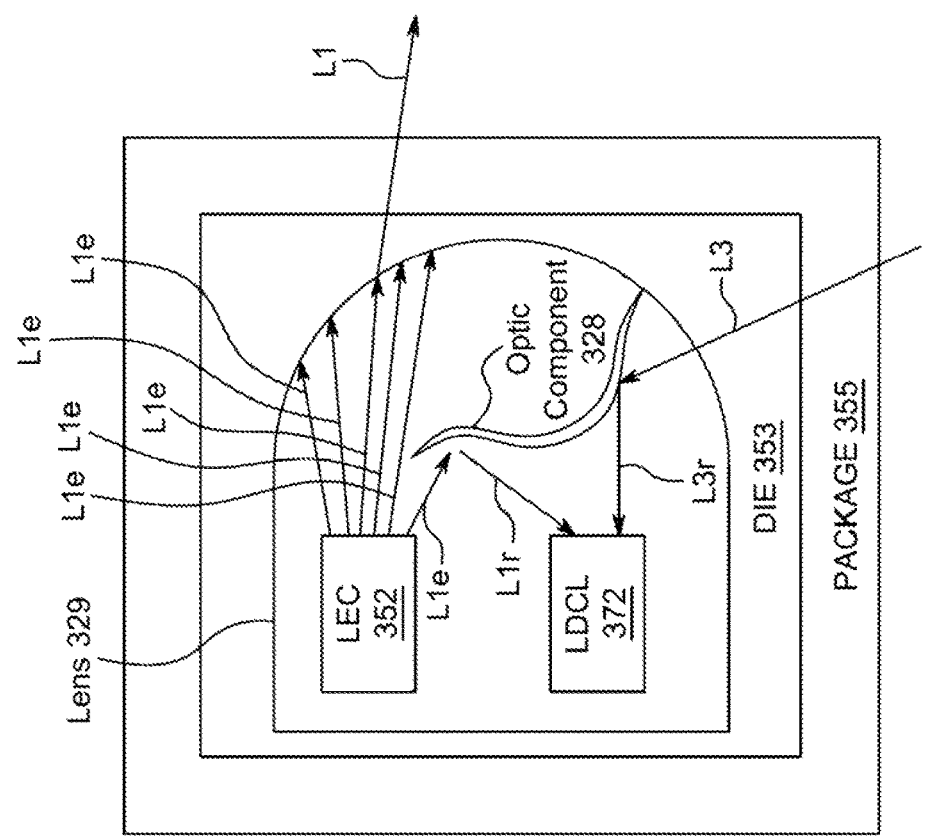

```
┌─────────────────────────────────────────────────────────────────────┐
│  WHILE A LIGHT EMITTING DIODE IS EMITTING LIGHT INTO A CHAMBER SPACE FOR │
│  ENABLING THE DETERMINATION OF A SMOKE CONDITION WITHIN AN ENVIRONMENT  │
│  SPACE, DETECTING THE MAGNITUDE OF A FORWARD VOLTAGE OF THE LIGHT       │
│                         EMITTING DIODE                                  │
│                              602                                        │
└─────────────────────────────────────────────────────────────────────┘
                                  ↓
┌─────────────────────────────────────────────────────────────────────┐
│   CALCULATING THE TEMPERATURE OF THE LIGHT EMITTING DIODE USING THE    │
│  DETECTED MAGNITUDE OF THE FORWARD VOLTAGE OF THE LIGHT EMITTING DIODE │
│                              604                                        │
└─────────────────────────────────────────────────────────────────────┘
                                  ↓
┌─────────────────────────────────────────────────────────────────────┐
│   DETERMINING THE TEMPERATURE OF A PORTION OF THE ENVIRONMENT SPACE   │
│      THAT IS EXTERNAL TO THE CHAMBER SPACE USING THE CALCULATED       │
│               TEMPERATURE OF THE LIGHT EMITTING DIODE                 │
│                              606                                        │
└─────────────────────────────────────────────────────────────────────┘
```

SYSTEMS AND METHODS FOR OPTICALLY COUPLING OPTOELECTRONIC COMPONENTS OF A HAZARD DETECTION SYSTEM TO DETERMINE A SMOKE CONDITION OF AN ENVIRONMENT

FIELD

This patent specification relates to apparatus, systems, methods, and related computer program products for handling temperature variation with optoelectronic components of a hazard detection system. More particularly, this patent specification relates to apparatus, systems, methods, and related computer program products for optically coupling optoelectronic components of a hazard detection system to determine a smoke condition of an environment of the hazard detection system.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Hazard detection systems, such as smoke detectors, carbon monoxide detectors, combination smoke and carbon monoxide detectors, as well as systems for detecting other dangerous conditions, have been used in residential, commercial, and industrial settings for safety considerations. These systems may be exposed to varying temperature conditions, which may be of interest for hazard detection and/or may negatively affect the functionality of certain system components (e.g., optoelectronic components). Accordingly, apparatus, systems, methods, and related computer program products for handling temperature variation with optoelectronic components of a hazard detection system are needed.

BRIEF SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

Apparatus, systems, methods, and related computer program products for handling temperature variation with optoelectronic components of a hazard detection system are provided herein.

In some embodiments, a hazard detection system may include a chamber body defining a chamber space within an enclosure space, a light emitting diode operative to emit light into the chamber space, a light detecting diode operative to detect the light emitted into the chamber space, and a processing subsystem operative to determine a current particular smoke condition within the enclosure space based on the current amount of the light detected by the light detecting diode, determine a current value of a power characteristic of one of the light emitting diode and the light detecting diode, determine the current temperature of the one of the light emitting diode and the light detecting diode based on the determined current value of the power characteristic of the one of the light emitting diode and the light detecting diode, access thermal resistance data indicative of a thermal resistance between a portion of the enclosure space and the one of the light emitting diode and the light detecting diode, and determine the current temperature of the portion of the enclosure space based on the accessed thermal resistance data and the determined current temperature of the one of the light emitting diode and the light detecting diode.

In some other embodiments, a method for operating a hazard detection system may be provided, wherein the hazard detection system includes a chamber body defining a chamber space within an enclosure space, an optoelectronic emitter, an optoelectronic detector, and a processing subsystem. The method includes emitting light from the optoelectronic emitter into the chamber space, detecting at least a portion of the emitted light with the optoelectronic detector, determining, with the processing subsystem, a smoke condition within the enclosure space based on an amount of the emitted light detected by the optoelectronic detector, determining, with the processing subsystem, a value of a power characteristic of one of the optoelectronic emitter during the emitting and the optoelectronic detector during the detecting, determining, with the processing subsystem, the temperature of the one of the optoelectronic emitter and the optoelectronic detector based on the determined value of the power characteristic, accessing, with the processing subsystem, thermal resistance data indicative of a thermal resistance between a portion of the enclosure space and the one of the optoelectronic emitter and the optoelectronic detector, and determining, with the processing subsystem, the temperature of the portion of the enclosure space based on the accessed thermal resistance data and the determined temperature.

In some other embodiments, a method for operating an electronic device may be provided, wherein the electronic device includes a light emitting diode and a chamber body that at least partially defines a chamber space within an environment space. The method may include, while the light emitting diode is emitting light into the chamber space for enabling the determination of a smoke condition within the environment space, detecting the magnitude of a forward voltage of the light emitting diode. The method may also include calculating the temperature of the light emitting diode using the detected magnitude of the forward voltage of the light emitting diode and determining the temperature of a portion of the environment space that is external to the chamber space using the calculated temperature of the light emitting diode.

In some other embodiments, a hazard detection system may include a chamber body defining a chamber space, a light emitting diode operative to emit light into the chamber space, a light detecting diode operative to detect the light emitted into the chamber space, and a processing subsystem operative to determine a current value of a power characteristic of one of the light emitting diode and the light detecting diode, determine the current temperature of the one of the light emitting diode and the light detecting diode based on the determined current value of the power characteristic of the one of the light emitting diode and the light detecting diode, and determine a current particular smoke condition within the chamber space based on the current amount of the light detected by the light detecting diode and the determined current temperature of the one of the light emitting diode and the light detecting diode.

In some other embodiments, a method for operating a hazard detection system may be provided, wherein the hazard detection system includes a chamber body defining a chamber space, an optoelectronic emitter, an optoelectronic detector, and a processing subsystem. The method may include emitting light from the optoelectronic emitter into the chamber space, detecting at least a portion of the emitted light with the optoelectronic detector, determining, with the processing subsystem, a value of a power characteristic of one of the optoelectronic emitter during the emitting and the optoelectronic detector during the detecting, determining, with the processing subsystem, the temperature of the one of the optoelectronic emitter and the optoelectronic detector based on the determined value of the power characteristic of the one of the optoelectronic emitter and the optoelectronic detector, and determining, with the processing subsystem, a smoke condition within the chamber space based on an amount of the emitted light detected by the optoelectronic detector and the determined temperature of the one of the optoelectronic emitter and the optoelectronic detector.

In some other embodiments, a method for operating an electronic device may be provided, wherein the electronic device includes a light emitting diode and a chamber body that at least partially defines a chamber space. While the light emitting diode is emitting light into the chamber space, the method may include detecting the magnitude of a forward voltage of the light emitting diode. The method may also include calculating the temperature of the light emitting diode using the detected magnitude of the forward voltage of the light emitting diode and determining a smoke condition within the chamber space using the calculated temperature of the light emitting diode.

In some other embodiments, a hazard detection system may include a chamber body defining a chamber space, a light emitting diode operative to emit light with an emitted magnitude, a first light detecting diode, an optical coupling structure operative to enable a first portion of the emitted light with a detected magnitude to be detected by the first light detecting diode, enable a second portion of the emitted light to be emitted into the chamber space, and maintain a constant ratio between the value of the emitted magnitude and the value of the detected magnitude despite variation in the value of the emitted magnitude, a second light detecting diode operative to detect the second portion of the emitted light, and a processing subsystem operative to determine the current value of the detected magnitude based on the current value of a power characteristic of the first light detecting diode, compare the determined current value of the detected magnitude with a particular value, dictate the value of a power characteristic of the light emitting diode based on the comparison, and determine a current particular smoke condition within the chamber space based on the current amount of the second portion of the emitted light detected by the second light detecting diode.

In some other embodiments, a method for operating a hazard detection system may be provided, wherein the hazard detection system includes a chamber body defining a chamber space, an optoelectronic emitter, a first optoelectronic detector, a second optoelectronic detector, an optical coupling structure ensuring a light path between the optoelectronic emitter and the first optoelectronic detector, and a processing subsystem. The method may include emitting light from the optoelectronic emitter, detecting a first portion of the emitted light with the first optoelectronic detector via the optical coupling structure, detecting a second portion of the emitted light with the second optoelectronic detector via the chamber space, varying, with the processing subsystem, the value of a power characteristic of the optoelectronic emitter based on the radiance of the first portion of the emitted light detected with the first optoelectronic detector, and determining, with the processing subsystem, a smoke condition within the chamber space based on the radiance of the second portion of the emitted light detected with the second optoelectronic detector.

In some other embodiments, a method for operating an electronic device may be provided, wherein the electronic device includes a chamber body that at least partially defines a chamber space, a light emitting diode, and a photodiode. While the light emitting diode is emitting light for enabling the determination of a smoke condition within the chamber space, the method may include detecting a first portion of the emitted light with the photodiode. The method may also include dictating the amount of current injected into the light emitting diode based on the magnitude of the first portion of the emitted light detected with the photodiode.

In some other embodiments, a hazard detection system may include a chamber body defining a chamber space, a first light subsystem, a second light subsystem, a third light subsystem, and a processing subsystem, wherein the first light subsystem is operative to emit first light into the chamber space during a first period of a cycle, the second light subsystem is operative to detect a first portion of the first light within the chamber space during the first period of the cycle, the third light subsystem is operative to detect a second portion of the first light within the chamber space during the first period of the cycle, the second light subsystem is operative to emit second light into the chamber space during a second period of the cycle, the first light subsystem is operative to detect a first portion of the second light within the chamber space during the second period of the cycle, the third light subsystem is operative to detect a second portion of the second light within the chamber space during the second period of the cycle, and the processing subsystem is operative to determine a characteristic of a hazard particle within the chamber space based on the radiance of each one of the first portion of the first light, the second portion of the first light, the first portion of the second light, and the second portion of the second light.

In some other embodiments, a method for operating a hazard detection system may be provided, wherein the hazard detection system includes a chamber body defining a chamber space, a first optoelectronic subsystem, a second optoelectronic subsystem, a third optoelectronic subsystem, and a processing subsystem. The method may include emitting first light into the chamber space from the first optoelectronic subsystem, detecting a first portion of the first emitted light with the second optoelectronic subsystem, detecting a second portion of the first emitted light with the third optoelectronic subsystem, after the emitting the first light, emitting second light into the chamber space from one of the second optoelectronic subsystem and the third optoelectronic subsystem, detecting a first portion of the second emitted light with the first optoelectronic subsystem, detecting a second portion of the second emitted light with the other one of the second optoelectronic subsystem and the third optoelectronic subsystem, and determining, with the processing subsystem, a characteristic of a hazard particle within the chamber space based on the radiance of each one of the first portion of the first light, the second portion of the first light, the first portion of the second light, and the second portion of the second light.

In some other embodiments, a method may be provided for operating a hazard detection system, wherein the hazard detection system includes a chamber body defining a chamber space, a first optoelectronic subsystem, a second optoelectronic subsystem, and a third optoelectronic subsystem. The method may include emitting first light from the first optoelectronic subsystem into the chamber space, detecting an obscuration portion of the first emitted light with the second optoelectronic subsystem, detecting a backscattered portion of the first emitted light with the third optoelectronic subsystem, after the emitting the first light, emitting second light from the second optoelectronic subsystem into the chamber space, detecting an obscuration portion of the second emitted light with the first optoelectronic subsystem, and detecting a forward scattered portion of the second emitted light with the third optoelectronic subsystem.

In some other embodiments, a method may be provided for operating a hazard detection system, wherein the hazard detection system includes a chamber body defining a chamber space, a first optoelectronic subsystem, a second optoelectronic subsystem, a third optoelectronic subsystem, and a fourth optoelectronic subsystem. The method may include emitting first light from the first optoelectronic subsystem into the chamber space, detecting a backscattered portion of the first emitted light with the second optoelectronic subsystem, detecting a forward scattered portion of the first emitted light with the third optoelectronic subsystem, after the emitting the first light, emitting second light from the fourth optoelectronic subsystem into the chamber space, detecting a forward scattered portion of the second emitted light with the second optoelectronic subsystem, and, detecting a backscattered portion of the second emitted light with the third optoelectronic subsystem.

Various refinements of the features noted above may be used in relation to various aspects of the present disclosure. Further features may also be incorporated in these various aspects as well. These refinements and additional features may be used individually or in any combination. For instance, various features discussed below in relation to one or more of the illustrated embodiments may be incorporated into any of the above-described aspects of the present disclosure alone or in any combination. Unless otherwise stated, features described in the context of one example may be combined or used with features described in the context of one or more other examples. The summary presented above is intended only to familiarize the reader with certain aspects and contexts of embodiments of the present disclosure without limitation to the claimed subject matter.

A further understanding of the nature and advantages of the embodiments discussed herein may be realized by reference to the remaining portions of the specification and the drawings.

BRIEF DESCRIPTION OF THE DRAWINGS

The discussion below makes reference to the following drawings, in which like reference characters may refer to like parts throughout, and in which:

FIGS. 3A-3H show schematic views of exemplary portions of the hazard detection system of FIG. 3, according to some embodiments;

FIGS. 5-13 show illustrative flowcharts of illustrative processes for operating a hazard detection system, according to some embodiments.

DETAILED DESCRIPTION

Figure 1:
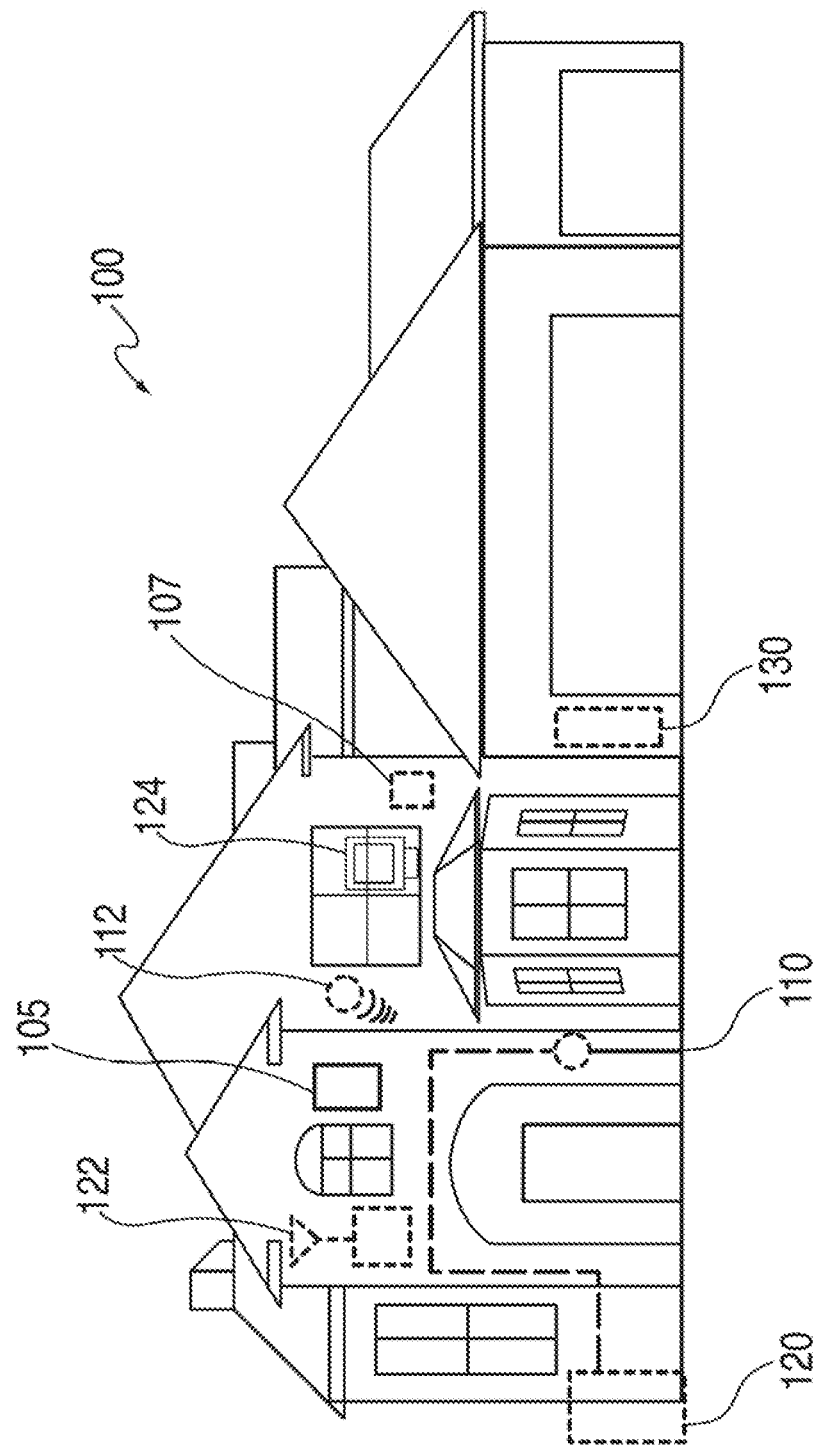
FIG. 1 shows an illustrative diagram of an enclosure with a hazard detection system, according to some embodiments.

In the following detailed description, for purposes of explanation, numerous specific details are set forth to provide a thorough understanding of the various embodiments. Those of ordinary skill in the art will realize that these various embodiments are illustrative only and are not intended to be limiting in any way. Other embodiments will readily suggest themselves to such skilled persons having the benefit of this disclosure.

In addition, for clarity purposes, not all of the routine features of the embodiments described herein are shown or described. One of ordinary skill in the art would readily appreciate that in the development of any such actual embodiment, numerous embodiment-specific decisions may be required to achieve specific design objectives. These design objectives will vary from one embodiment to another and from one developer to another. Moreover, it will be appreciated that such a development effort might be complex and time-consuming but would nevertheless be a routine engineering undertaking for those of ordinary skill in the art having the benefit of this disclosure.

It is to be appreciated that while one or more hazard detection systems may be described further herein in the context of being used in a residential home, such as a single-family residential home, the scope of the present teachings is not so limited. More generally, hazard detection systems may be applicable to a wide variety of enclosures such as, for example, duplexes, townhomes, multi-unit apartment buildings, hotels, retail stores, office buildings, and industrial buildings. It is to be understood that the term enclosure may also be a non-contained environment that may be protected by a hazard detection system of this disclosure, such as an outdoor shopping mall or outdoor patio or any space that may be either partially or completely indoors or outdoors. Further, it is understood that while the terms user, customer, installer, homeowner, occupant, guest, tenant, landlord, repair person, and the like may be used to refer to the person or persons who are interacting with the hazard detector in the context of one or more scenarios described herein, these references are by no means to be considered as limiting the scope of the present teachings with respect to the person or persons who may be performing such actions.

Smoke detectors may generally work according to an ionization technique or a light scattering technique. Conventional ionization techniques may use a radioactive source to ionize air within the smoke chamber. The radioactive source may typically be Americium-241 and can convert air molecules into positive and negative ions. In a conventional radioactive ionization smoke detector, a small amount of radioactive material may be placed between two electrically charged plates. The radiation emitting from the radioactive material may ionize the air between the plates and may cause a current to flow between the plates. When smoke enters the smoke chamber, it may disrupt ionization of the air, thereby reducing the current flow. Particularly, the ions may bond with the smoke or may be displaced by the smoke, thus breaking the current flow between the two plates. When this reduced current flow is detected, an alarm may be activated. In conventional ionization smoke detectors, the radioactive source may serve as the ionization source. Use of radioactive materials, however, may not be desired, and some jurisdictions outlaw their use in commercial products such as smoke detectors.

The light scattering technique may be used in a photoelectric smoke alarm. In a photoelectric smoke alarm, a light source may be aimed into a sensing chamber at an angle away from a sensor. Smoke may enter the chamber, which may scatter light onto a light sensor, thereby triggering an alarm. Embodiments discussed herein may operate in connection with a smoke chamber containing one or at least two optical sources, each operating at a different wavelength (e.g., infrared and blue), that may project light energy into the chamber. One or more sensors can monitor for scattered light when smoke and/or other particles enter the chamber. Multiple optical sources may be used so that different sized particles can be detected, thereby enabling various algorithms to use the data to make more informed decisions when operating the hazard detection system. For example, white/gray smoke may have different mean particle sizes than black smoke. In addition, smoke from fast burning fires may have different mean particle sizes than smoldering fires. Mean particle sizes may also differ based on the material that is burning. In addition, moisture particles may have different mean particles size than smoke particles and dust.

The optical sources may typically be light emitting diodes (LEDs) that may emit light energy when power is applied. For example, a blue LED may emit light energy in the blue electromagnetic spectrum and an infrared (IR) LED may emit light energy in the infrared electromagnetic spectrum. Different LEDs may exhibit different forward voltage drops based on a combination of factors, such as semiconductor physics, output current, temperature, and/or manufacturing variances. For example, an IR LED may have a first voltage drop of about 2.1 volts and a blue LED may have a second voltage drop of about 3.4 volts. The different forward voltage drops may require the supply of different voltages within the system in order to adequately power the LEDs. In addition, in order for the LEDs to produce consistent light output, so that consistent and reliable smoke readings may be taken, each LED may be supplied with a substantially constant current using circuitry according to various embodiments described herein.

A power characteristic of an optoelectronic component (e.g., a forward voltage of a light emitting diode) of the hazard detection system may be used to determine a temperature of an environment of the hazard detection system. A power characteristic of an optoelectronic component of the hazard detection system (e.g., a forward voltage of a light emitting diode) may be used to determine a smoke condition of an environment of the hazard detection system. Optoelectronic components (e.g., a light emitting diode and a photodiode) of the hazard detection system may be optically coupled to determine a smoke condition of an environment of the hazard detection system.

Turning to the figures, FIG. 1 is a diagram illustrating an exemplary enclosure 100 that may include and use a hazard detection system 105, remote hazard detection system 107, thermostat 110, remote thermostat 112, heating, cooling, and ventilation (HVAC) system 120, router 122, computer 124, and/or central panel 130 in accordance with some embodiments (e.g., as a smart home environment). Enclosure 100 can be, for example, a single-family dwelling, a duplex, an apartment within an apartment building, a warehouse, or a commercial structure such as an office or retail store. Hazard detection system 105 can be battery powered, line powered, or line powered with a battery backup. Hazard detection system 105 can include one or more processors, multiple sensors, non-volatile storage, and other circuitry to provide desired safety monitoring and user interface features. Some user interface features may only be available in line powered embodiments due to physical limitations and power constraints. In addition, some features common to both line and battery powered embodiments may be implemented differently. Hazard detection system 105 can include, for example, the following components: low power wireless personal area network (6LoWPAN) circuitry, a system processor, a safety processor, non-volatile memory (e.g., Flash), Wi-Fi circuitry, an ambient light sensor (ALS), a smoke sensor, a carbon monoxide (CO) sensor, a temperature sensor, a humidity sensor, a noise sensor, one or more ultrasonic sensors, a passive infra-red (PIR) sensor, a microphone, a speaker, one or more light emitting diodes (LED's), one or more light detecting diodes (e.g., photodiodes), any other suitable optoelectronics, an alarm buzzer, and the like.

Hazard detection system 105 can monitor environmental conditions associated with enclosure 100 and alarm occupants when an environmental condition exceeds a predetermined threshold. The monitored conditions can include, for example, smoke, heat, humidity, carbon monoxide, radon, methane, and other gasses. In addition to monitoring the safety of the environment, hazard detection system 105 can provide several user interface features not found in conventional alarm systems. These user interface features can include, for example, vocal or other suitable audible alarms, voice setup instructions, cloud communications (e.g., push monitored data to the cloud, or push notifications to a mobile telephone, or receive software updates from the cloud), device-to-device communications (e.g., communicate with other hazard detection systems in the enclosure), visual safety indicators (e.g., display of a green light may indicate that no anomalous conditions are detected and display of a red light may indicate danger), tactile and non-tactile input command processing, and software updates.

Hazard detection system 105 can monitor other conditions that may not necessarily be tied to hazards, per se, but can be configured to perform a security role. In the security role, system 105 may monitor occupancy (e.g., using a motion detector), ambient light, sound, remote conditions provided by remote sensors (e.g., door sensors, window sensors, and/or motion sensors). In some embodiments, system 105 can perform both hazard safety and security roles, and, in other embodiments, system 105 may perform one of a hazard safety role and a security role.

Hazard detection system 105 can implement multi-criteria state machines according to various embodiments to provide advanced hazard detection and advanced user interface features such as pre-alarms. In addition, multi-criteria state machines can manage alarming states and pre-alarming states and can include one or more sensor state machines that can control the alarming states and/or one or more system state machines that control the pre-alarming states. Each state machine can transition among any one of its states based on sensor data values, hush events, and/or transition conditions. The transition conditions can define how a state machine may transition from one state to another, and ultimately, how hazard detection system 105 may operate. Hazard detection system 105 can use a dual processor arrangement to execute the multi-criteria state machines according to various embodiments. The dual processor arrangement may enable hazard detection system 105 to manage the alarming and pre-alarming states in a manner that may use minimal power while simultaneously providing failsafe hazard detection and alarming functionalities. Additional details of the various embodiments of hazard detection system 105 are discussed below.

Enclosure 100 can include any number of hazard detection systems. For example, as shown, hazard detection system 107 may be another hazard detection system, which may be similar to system 105. In one embodiment, both systems 105 and 107 can be battery powered systems. In another embodiment, system 105 may be line powered, and system 107 may be battery powered. Moreover, a hazard detection system can be installed outside of enclosure 100.

Thermostat 110 can be one of several thermostats that may control HVAC system 120. Thermostat 110 can be referred to as the "primary" thermostat because it may be electrically connected to actuate all or part of an HVAC system, by virtue of an electrical connection to HVAC control wires (e.g., W, G, Y, etc.) leading to HVAC system 120. Thermostat 110 can include one or more sensors to gather data from the environment associated with enclosure 100. For example, a sensor may be used to detect occupancy, temperature, light and other environmental conditions within enclosure 100. Remote thermostat 112 can be referred to as an "auxiliary" thermostat because it may not be electrically connected to actuate HVAC system 120, but it too may include one or more sensors to gather data from the environment associated with enclosure 100 and can transmit data to thermostat 110 via a wired or wireless link. For example, thermostat 112 can wirelessly communicate with and cooperates with thermostat 110 for improved control of HVAC system 120. Thermostat 112 can provide additional temperature data indicative of its location within enclosure 100, provide additional occupancy information, and/or provide another user interface for the user (e.g., to adjust a temperature setpoint).

Hazard detection systems 105 and 107 can communicate with thermostat 110 or thermostat 112 via a wired or wireless link. For example, hazard detection system 105 can wirelessly transmit its monitored data (e.g., temperature and occupancy detection data) to thermostat 110 so that it may be provided with additional data to make better informed decisions in controlling HVAC system 120. Moreover, in some embodiments, data may be transmitted from one or more of thermostats 110 and 112 to one or more of hazard detections systems 105 and 107 via a wired or wireless link.

Central panel 130 can be part of a security system or other master control system of enclosure 100. For example, central panel 130 may be a security system that may monitor windows and doors for break-ins, and monitor data provided by motion sensors. In some embodiments, central panel 130 can also communicate with one or more of thermostats 110 and 112 and hazard detection systems 105 and 107. Central panel 130 may perform these communications via wired link, wireless link, or a combination thereof. For example, if smoke is detected by hazard detection system 105, central panel 130 can be alerted to the presence of smoke and may make the appropriate notification, such as displaying an indicator that a particular zone within enclosure 100 is experiencing a hazard condition.

Enclosure 100 may further include a private network accessible wirelessly and/or through wired connections and may also be referred to as a Local Area Network or LAN. Network devices on the private network can include hazard detection systems 105 and 107, thermostats 110 and 112, computer 124, and/or central panel 130. In one embodiment, the private network may be implemented using router 122, which can provide routing, wireless access point functionality, firewall and multiple wired connection ports for connecting to various wired network devices, such as computer 124. Wireless communications between router 122 and networked devices can be performed using an 802.11 protocol or any other suitable protocol. Router 122 can further provide network devices access to a public network, such as the Internet or the Cloud, through a cable-modem, DSL modem and an Internet service provider or provider of other public network services. Public networks like the Internet are sometimes referred to as a Wide-Area Network or WAN.

Access to the Internet, for example, may enable networked devices such as system 105 or thermostat 110 to communicate with a device or server remote to enclosure 100. The remote server or remote device can host an account management program that may manage various networked devices contained within enclosure 100. For example, in the context of hazard detection systems according to embodiments discussed herein, system 105 can periodically upload data to the remote server via router 122. In addition, if a hazard event is detected, the remote server or remote device can be notified of the event after system 105 may communicate the notice via router 122. Similarly, system 105 can receive data (e.g., commands or software updates) from the account management program via router 122.

Hazard detection system 105 can operate in one of several different power consumption modes. Each mode can be characterized by the features performed by system 105 and the configuration of system 105 to consume different amounts of power. Each power consumption mode may correspond to a quantity of power consumed by hazard detection system 105, and the quantity of power consumed can range from a lowest quantity to a highest quantity. One of the power consumption modes may correspond to the lowest quantity of power consumption, and another power consumption mode may correspond to the highest quantity of power consumption, and all other power consumption modes may fall somewhere between the lowest and the highest quantities of power consumption. Examples of power consumption modes can include an Idle mode, a Log Update mode, a Software Update mode, an Alarm mode, a Pre-Alarm mode, a Hush mode, and a Night Light mode. These power consumption modes are merely illustrative and are not meant to be limiting. Additional or fewer power consumption modes may exist. Moreover, any definitional characterization of the different modes described herein is not meant to be all inclusive, but rather, is meant to provide a general context of each mode.

Figure 2:
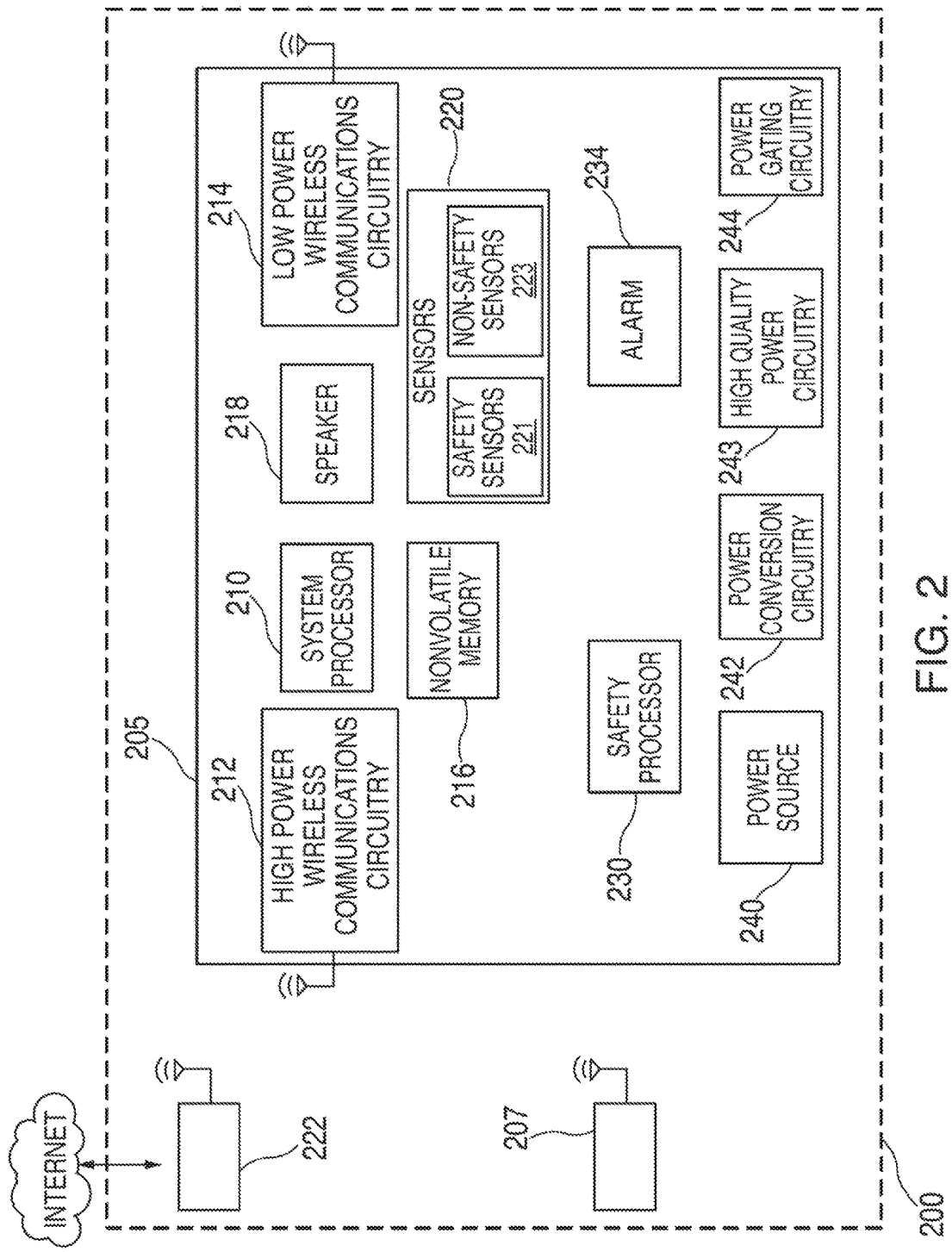
FIG. 2 shows an illustrative block diagram of a hazard detection system being used in an illustrative enclosure, according to some embodiments.

FIG. 2 shows an illustrative block diagram of hazard detection system 205 being used in an illustrative enclosure 200 in accordance with some embodiments. FIG. 2 also shows optional hazard detection system 207 and router 222. Hazard detection systems 205 and 207 can be similar to hazard detection systems 105 and 107 in FIG. 1, enclosure 200 can be similar to enclosure 100 in FIG. 1, and router 222 can be similar to router 122 in FIG. 1. Hazard detection system 205 can include several components, including system processor 210, high-power wireless communications circuitry 212 and antenna, low-power wireless communications circuitry 214 and antenna, non-volatile memory 216, speaker 218, sensors 220, which can include one or more safety sensors 221 and one or more non-safety sensors 223, safety processor 230, alarm 234, power source 240, power conversion circuitry 242, high quality power circuitry 243, and power gating circuitry 244. Hazard detection system 205 may be operative to provide failsafe safety detection features and user interface features using circuit topology and power budgeting methods that may minimize power consumption.

Hazard detection system 205 can use a bifurcated processor circuit topology for handling the features of system 205. Both system processor 210 and safety processor 230 can exist on the same circuit board within system 205, but may perform different tasks. System processor 210 may be a larger more capable processor that can consume more power than safety processor 230. System processor 210 can be operative to process user interface features. For example, processor 210 can direct wireless data traffic on both high and low power wireless communications circuitries 212 and 214, access non-volatile memory 216, communicate with processor 230, and/or cause audio to be emitted from speaker 218. As another example, processor 210 can monitor data acquired by one or more sensors 220 to determine whether any actions need to be taken (e.g., shut off a blaring alarm in response to a user detected action to hush the alarm).

Safety processor 230 can be operative to handle safety related tasks of system 205. Safety processor 230 can poll one or more of sensors 220 and/or activate alarm 234 when one or more of sensors 220 indicate a hazard event is detected. Processor 230 can operate independently of processor 210 and/or can activate alarm 234 regardless of what state processor 210 may be in. For example, if processor 210 is performing an active function (e.g., performing a Wi-Fi update) or is shut down due to power constraints, processor 230 can activate alarm 234 when a hazard event is detected. In some embodiments, software running on processor 230 may be permanently fixed and may never be updated via a software or firmware update after system 205 leaves the factory. In other embodiments, processor 230 may be updated when system 205 is in the field.

Compared to processor 210, processor 230 may be a less power consuming processor. Thus, by using processor 230 in lieu of processor 210 to monitor a subset of sensors 220 may yield a power savings. If processor 210 were to constantly monitor sensors 220, the power savings may not be realized. In addition to the power savings realized by using processor 230 for monitoring the subset of sensors 220, bifurcating the processors may also ensure that the safety monitoring and core alarming features of system 205 may operate regardless of whether processor 210 is functioning. By way of example and not by way of limitation, system processor 210 can include a relatively high-powered processor such as Freescale Semiconductor K24 or K60 Microcontroller, while safety processor 230 may comprise a relatively low-powered processor such as a Freescale Semiconductor KL16 Microcontroller. Overall operation of hazard detection system 205 may entail a judiciously architected cooperation of system processor 210 and safety processor 230, where system processor 210 may perform selected higher-level, advanced functions that may not have been conventionally associated with hazard detection units (e.g., more advanced user interface and communications functions; various computationally-intensive algorithms to sense patterns in user behavior or patterns in ambient conditions; algorithms for governing, for example, the brightness of an LED night light as a function of ambient brightness levels; algorithms for governing, for example, the sound level of an onboard speaker for home intercom functionality; algorithms for governing, for example, the issuance of voice commands to users; algorithms for uploading logged data to a central server; algorithms for establishing network membership; and so forth), and where safety processor 230 may perform the more basic functions that may have been more conventionally associated with hazard detection units (e.g., smoke and CO monitoring, actuation of shrieking/buzzer alarms upon alarm detection, and so forth). By way of example and not by way of limitation, system processor 210 may consume on the order of 18 mW when it is in a relatively high-power active state and performing one or more of its assigned advanced functionalities, whereas safety processor 230 may only consume on the order of 0.05 mW when it is performing its basic monitoring functionalities. However, again by way of example and not by way of limitation, system processor 210 may consume only on the order of 0.005 mW when in a relatively low-power inactive state, and the advanced functions that it may perform may be judiciously selected and timed such that system processor 210 may be in the relatively high power active state only about 0.05% of the time, and may spend the rest of the time in the relatively low-power inactive state. Safety processor 230, while only requiring an average power draw of 0.05 mW when it may be performing its basic monitoring functionalities, may of course be performing its basic monitoring functionalities 100% of the time. According to one or more embodiments, a judiciously architected functional overlay of system processor 210 and safety processor 230 may be designed such that hazard detection system 205 can perform basic monitoring and shriek/buzzer alarming for hazard conditions even in the event that system processor 210 is inactivated or incapacitated, by virtue of the ongoing operation of safety processor 230. Therefore, while system processor 210 may be configured and programmed to provide many different capabilities for making hazard detection unit 205 an appealing, desirable, updatable, easy-to-use, intelligent, network-connected sensing and communications node for enhancing the smart-home environment, its functionalities may be advantageously provided in the sense of an overlay or adjunct to the core safety operations governed by safety processor 230, such that even in the event that there are operational issues or problems with system processor 210 and its advanced functionalities, the underlying safety-related purpose and functionality of hazard detector 205 by virtue of the operation of safety processor 230 may continue on, with or without system processor 210 and its advanced functionalities.

High power wireless communications circuitry 212 can be, for example, a Wi-Fi module capable of communicating according to any of the 802.11 protocols. For example, circuitry 212 may be implemented using Wi-Fi part number BCM43362, available from Broadcom and that may be mounted to a module available from Murata. Depending on an operating mode of system 205, circuitry 212 can operate in a low power "sleep" state or a high power "active" state. For example, when system 205 may be in an Idle mode, circuitry 212 can be in the "sleep" state. When system 205 may be in a non-Idle mode such as a Wi-Fi update mode, software update mode, or alarm mode, circuitry 212 can be in an "active" state. For example, when system 205 may be in an active alarm mode, high power circuitry 212 may communicate with router 222 so that a message can be sent to a remote server or device.

Low power wireless communications circuitry 214 can be a low power Wireless Personal Area Network (6LoWPAN) module or a ZigBee module capable of communicating according to an 802.15.4 protocol. In some embodiments, low power wireless communications circuitry 214 may serve as a node in a fabric network of devices. In another embodiment, circuitry 214 can be part number EM357 or EM3581 system on chip (SoC) available from Silicon Laboratories. In some embodiments, circuitry 214 can include Bluetooth Low Energy circuitry. Depending on the operating mode of system 205, circuitry 214 can operate in a relatively low power "sleep" state or a relatively high power "awake" state. When system 205 is in the Idle mode, Wi-Fi update mode, or software update mode, circuitry 214 can be in the "sleep" state. Circuitry 214 may transition from the sleep state to the awake state in response to receipt of a wake packet (e.g., transmitted by another device) or in response to a state change in one of the state machines running on system 205. When system 205 may be in an Alanii mode, circuitry 214 can transmit data (e.g., fabric messages) so that the low power wireless communications circuitry in system 207 can receive data indicating that system 205 is alarming. Thus, even though it is possible for high power wireless communications circuitry 212 to be used for listening for alarm events, it can be more power efficient to use low power circuitry 214 for this purpose. Power savings may be further realized when several hazard detection systems or other systems having low power circuitry 214 may form an interconnected wireless network (e.g., a fabric network).

Power savings may also be realized because in order for low power circuitry 214 to continually listen for data transmitted from other low power circuitry, circuitry 214 may constantly be operating in a "sleep" state. This state may consume power, and although it may consume more power than high power circuitry 212 operating in a sleep state, the power saved versus having to periodically activate high power circuitry 214 can be substantial. When high power circuitry 212 is in an active state and low power circuitry 214 is in an awake state, high power circuitry 212 can consume substantially more power than low power circuitry 214.

In some embodiments, low power wireless communications circuitry 214 can be characterized by its relatively low power consumption and its ability to wirelessly communicate according to a first protocol characterized by relatively low data rates, and high power wireless communications circuitry 212 can be characterized by its relatively high power consumption and its ability to wirelessly communicate according to a second protocol characterized by relatively high data rates.

In some embodiments, low power wireless communications circuitry 214 may be a mesh network compatible module that may not require a distinguished access point in order to communicate to devices in a network. Mesh network compatibility can include provisions that may enable mesh network compatible modules to keep track of other nearby mesh network compatible modules so that data can be passed through neighboring modules. Mesh network compatibility may be essentially the hallmark of the 802.15.4 protocol. In contrast, high power wireless communications circuitry 212 may not be a mesh network compatible module and may require an access point or router in order to communicate to devices in a network. Thus, if a first device having circuitry 212 wants to communicate data to another device having circuitry 212, the first device may have to communicate with the access point or router, which may then transmit the data to the second device. There may be no device-to-device communication per se using circuitry 212.

Non-volatile memory 216 can be any suitable permanent memory storage such as, for example, NAND Flash, a hard disk drive, NOR, ROM, or phase change memory. In one embodiment, non-volatile memory 216 can store audio clips that can be played back by speaker 218. The audio clips can include installation instructions or warnings in one or more languages. Speaker 218 can be any suitable speaker operable to playback sounds or audio files. Speaker 218 can include an amplifier (not shown).

Sensors 220 can be monitored by system processor 210 and/or safety processor 230, and can include safety sensors 221 and non-safety sensors 223. One or more of sensors 220 may be exclusively monitored by one of system processor 210 and safety processor 230. As defined herein, monitoring a sensor may refer to a processor's ability to acquire data from that monitored sensor. That is, one particular processor may be responsible for acquiring sensor data, and possibly storing it in a sensor log, but once the data is acquired, it can be made available to another processor either in the form of logged data or real-time data. For example, in one embodiment, system processor 210 may monitor one of non-safety sensors 223, but safety processor 230 may not monitor that same non-safety sensor. In another embodiment, safety processor 230 may monitor each of the safety sensors 221, but may provide the acquired sensor data to system processor 210.

Safety sensors 221 can include sensors that may be necessary for ensuring that hazard detection system 205 can monitor its environment for hazardous conditions and/or alert users when hazardous conditions are detected, and all other sensors not necessary for detecting a hazardous condition or not necessary for enabling such detecting in an accurate manner may be non-safety sensors 223. In some embodiments, safety sensors 221 may include only those sensors necessary for detecting a hazardous condition. For example, if the hazardous condition includes smoke and fire, then the safety sensors might only include a smoke sensor, and may or may not also include at least one distinct temperature sensor (e.g., a thermistor) and/or a relative humidity sensor (e.g., a temperature sensor may be a safety sensor along with a smoke sensor for sensing a smoke condition if the temperature sensor is configured to enable the smoke sensor to sense smoke accurately despite varying temperatures). Other sensors, such as non-safety sensors, could be included as part of system 205, but might not be needed to detect smoke or fire. As another example, if the hazardous condition includes carbon monoxide, then the safety sensor might be a carbon monoxide sensor, and no other sensor might be needed to perform this task.

Thus, sensors deemed necessary can vary based on the functionality and features of hazard detection system 205. In one embodiment, hazard detection system 205 can be a combination smoke, fire, and carbon monoxide alarm system. In such an embodiment, detection system 205 can include the following necessary safety sensors 221: a smoke detector, a carbon monoxide (CO) sensor, and/or one or more temperature sensors. Smoke detectors may typically use optical detection, ionization, or air sampling techniques to trigger the smoke condition. Optical scattering and obscuration detection techniques may use light emitting diodes (LEDs) (e.g., infrared (IR) LEDs) and one or more photodiodes. When smoke and/or other matter (e.g., water vapor) enters a smoke chamber, the light emitted by the LED(s) may be scattered, which may enable the photodiode(s) to detect the scattered light. If no smoke or other matter (e.g., water vapor) is in the smoke chamber, then the photodiode(s) may not be able to detect the light being emitted by the LED(s). In some embodiments, multiple LEDs may be incorporated in the smoke sensor. Each LED may emit light energy at a different wavelength than the other LEDs. Ionization techniques may use a radioactive material such as Americium-241 to ionize the air, which may create a measurable current between two detector plates. When smoke particles enter the chamber, they may bind to the ions. The reaction may produce a measurable drop in the conducted current between detector plates; the resulting drop may indicate smoke detection. In some geographic locations (e.g., Europe) traditional Americium-241 ionization smoke detectors may be banned by regulatory agencies in part because of the necessity to dispose of a radioactive material at the end of the smoke detector's life. A smoke detector can also use a non-radioactive ionization technique to detect the presence of smoke and/or other particulate matter. A non-radioactive ionizing detector may use an LED such as an ultraviolet emitting LED with a photocatalyst coating. The photocatalyst may generate ions when light (e.g., UV light) passes through it. When these ions are displaced or neutralized by smoke and/or other matter, the detector may detect a change in current between two plates and may register a smoke event.

A CO sensor can detect the presence of carbon monoxide gas, which, in the home, may typically be generated by open flames, space heaters, water heaters, blocked chimneys, and automobiles. The material used in electrochemical CO sensors may typically have a 5-10 year lifespan. Thus, after a 5-10 year period has expired, the CO sensor should be replaced. A dedicated heat or temperature sensor can be a thermistor, which may be a type of resistor whose resistance may vary based on temperature. Thermistors can include negative temperature coefficient (NTC) type thermistors or positive temperature coefficient (PTC) type thermistors. A relative humidity sensor may be used to distinguish between obscuration caused by smoke and steam or fog. Furthermore, in this embodiment, detection system 205 can include, for example, the following non-safety sensors 223: a humidity sensor, an ambient light sensor, a push-button sensor, a passive infra-red (PIR) sensor, and/or one or more ultrasonic sensors. A temperature and humidity sensor can provide relatively accurate readings of temperature and relative humidity for the purposes of environmental monitoring and HVAC control. An ambient light sensor (ALS) can detect ambient light and the push-button sensor can be a switch, for example, that may detect a user's press of the switch. A PIR sensor can be used for various motion detection features. Ultrasonic sensors can be used to detect the presence of an object. Such sensors can generate high frequency sound waves and may determine which wave(s) are received back by the sensor. Sensors 220 can be mounted to a printed circuit board (e.g., the same board to which processors 210 and 230 may be mounted), a flexible printed circuit board, a housing of system 205, or a combination thereof.

In some embodiments, data acquired from one or more non-safety sensors 223 can be acquired by the same processor that may be used to acquire data from one or more safety sensors 221. For example, safety processor 230 may be operative to monitor both safety and non-safety sensors 221 and 223 for power savings reasons, as discussed above. Although safety processor 230 may not need any of the data acquired from non-safety sensor 223 to perform any hazard monitoring and alerting functions, the non-safety sensor data can be utilized to provide enhanced hazard system 205 functionality. The enhanced functionality can be realized in alarming algorithms. For example, the non-sensor data can be utilized by system processor 210 to implement system state machines that may interface with one or more sensor state machines.

Alarm 234 can be any suitable alarm that may alert users in the vicinity of system 205 of the presence of a hazard condition (e.g., any suitable audible, visual, and/or tactile alarm). Alarm 234 can also be activated during testing scenarios. Alarm 234 can be a piezo-electric buzzer, for example.

Power source 240 can supply power to enable operation of system 205 and can include any suitable source of energy. Embodiments discussed herein can include AC line powered, battery powered, a combination of AC line powered with a battery backup, and externally supplied DC power (e.g., USB supplied power). Embodiments that use AC line power, AC line power with battery backup, or externally supplied DC power may be subject to different power conservation constraints than battery only embodiments. Battery powered embodiments may be designed to manage power consumption of its finite energy supply such that hazard detection system 205 may operate for a minimum period of time. In some embodiments, the minimum period of time can be one (1) year, three (3) years, or seven (7) years. In other embodiments, the minimum period of time can be at least seven (7) years, eight (8) years, nine (9) years, or ten (10) years. Line powered embodiments may not be as constrained because their energy supply may be virtually unlimited. Line powered with battery backup embodiments may employ power conservation methods to prolong the life of the backup battery.

In battery only embodiments, power source 240 may include one or more batteries or a battery pack. The batteries can be constructed from different compositions (e.g., alkaline or lithium iron disulfide) and different end-user configurations (e.g., permanent, user replaceable, or non-user replaceable) can be used. In one embodiment, six cells of Li—$FeS_2$ can be arranged in two stacks of three. Such an arrangement can yield about 27,000 mWh of total available power for system 205.

Power conversion circuitry 242 may include circuitry that may convert power from one level to another. Multiple instances of power conversion circuitry 242 may be used to provide the different power levels needed for the components within system 205. One or more instances of power conversion circuitry 242 can be operative to convert a signal supplied by power source 240 to a different signal. Such instances of power conversion circuitry 242 can exist in the form of buck converters or boost converters. For example, alarm 234 may require a higher operating voltage than high power wireless communications circuitry 212, which may require a higher operating voltage than processor 210, such that all required voltages may be different than the voltage supplied by power source 240. Thus, as can be appreciated in this example, at least three different instances of power conversion circuitry 242 may be required.

High quality power circuitry 243 may be operative to condition a signal supplied from a particular instance of power conversion circuitry 242 (e.g., a buck converter) to another signal. High quality power circuitry 243 may exist in the form of a low-dropout regulator. The low-dropout regulator may be able to provide a higher quality signal than that as may be provided by power conversion circuitry 242. Thus, certain components may be provided with "higher" quality power than other components. For example, certain safety sensors 221, such as smoke detectors and CO sensors, may require a more stable voltage in order to operate properly than digital circuitry within the system processor 210. Power circuitry may be customized to provide specific power signals for each LED being used in the smoke sensor.

Power gating circuitry 244 can be used to selectively couple and de-couple components from a power bus. De-coupling a component from a power bus may ensure that the component does not incur any quiescent current loss, and therefore can extend battery life beyond that which it might be if the component were not so de-coupled from the power bus. Power gating circuitry 244 can be a switch such as, for example, a MOSFET transistor. Even though a component may be de-coupled from a power bus and may not incur any current loss, power gating circuitry 244 itself may consume a small amount of power. This power consumption, however, may be less than the quiescent power loss of the component.

It is understood that although hazard detection system 205 may be described as having two separate processors, system processor 210 and safety processor 230, which may provide certain advantages, including advantages with regard to power consumption as well as with regard to survivability of core safety monitoring and alarming in the event of advanced feature provision issues, it is not outside the scope of the present teachings for one or more of the various embodiments discussed herein to be executed by one processor or by more than two processors.

Figure 3:
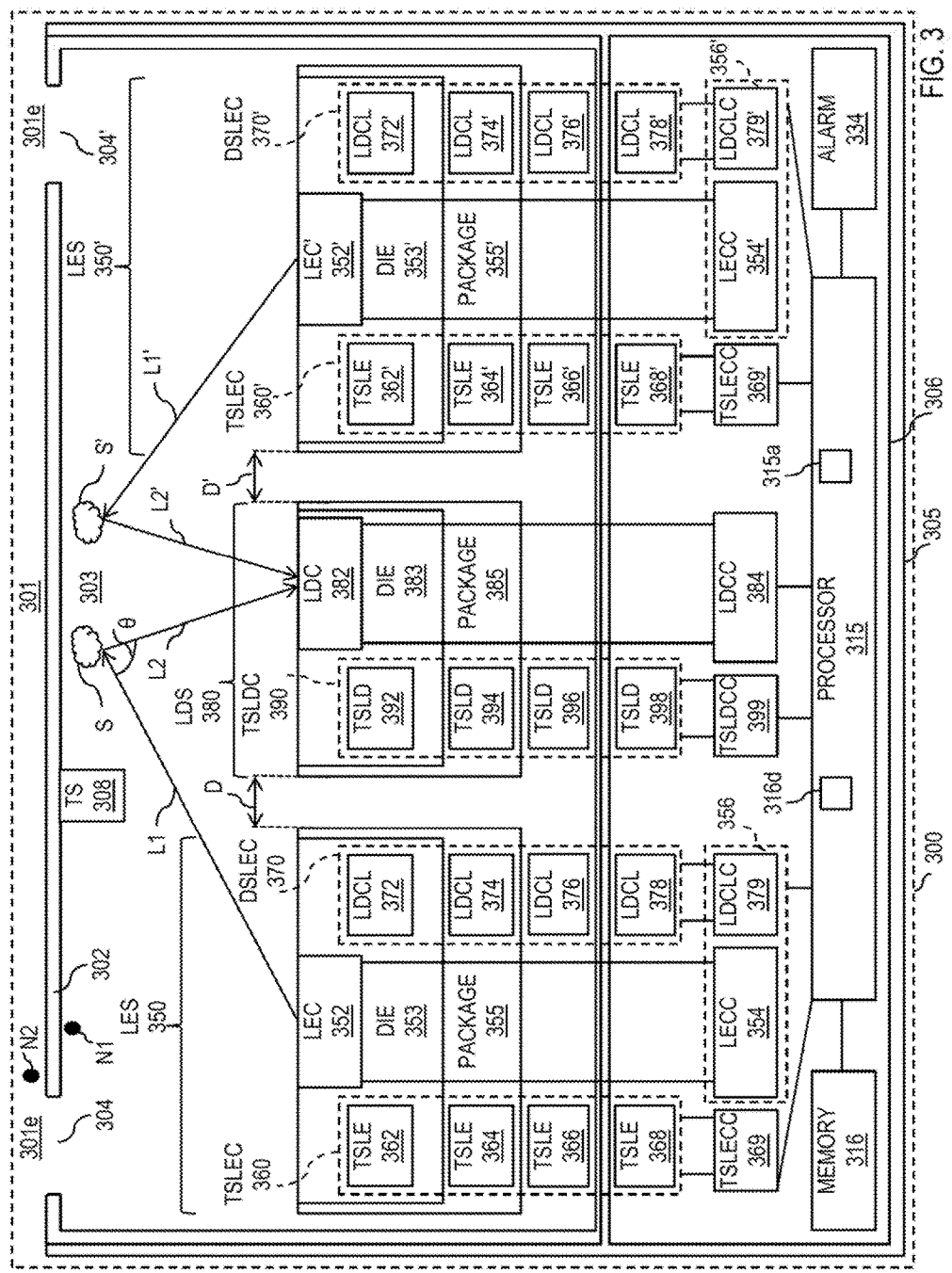
FIG. 3 shows an illustrative block diagram showing various components of a hazard detection system with optoelectronic components for handling temperature variation, according to some embodiments.

FIG. 3 shows a diagram illustrating an exemplary hazard detection system 305, which may be similar to hazard detection system 105 of FIG. 1 and/or hazard detection system 205 of FIG. 2, and which may be used as part of a smart home environment with respect to enclosure 300, which may be similar to enclosure 100 of FIG. 1 and/or enclosure 200 of FIG. 2. In some embodiments, hazard detection system 305 may be a smoke detector that may be configured to detect the presence of smoke within enclosure space 301 of enclosure 300 and then to initiate an alarm to warn an occupant or occupants of enclosure 300 of a potential fire or other danger. In other embodiments, hazard detection system 305 may be a carbon monoxide detector, heat detector, and/or any other suitable hazard detector for space 301. In some particular embodiments, hazard detection system 305 may be a multi-sensing detector that may include a smoke detector, carbon monoxide detector, heat detector, motion detector, and the like for space 301. For convenience in describing the embodiments herein, hazard detection system 305 may be referred to hereinbelow as smoke detector 305, although it should be realized that hazard detection system 305 may include various other devices and that the scope of the present teachings is not necessarily limited to hazard detectors in which smoke is required as one of the anomalies to be detected. Thus, for example, depending on the particular context as would be apparent to a person skilled in the art upon reading the instant disclosure, one or more of the advantageous features and embodiments described herein may be readily applicable to any single or multi-functional hazard sensor, which for example, may detect smoke only, or heat only, or smoke and heat only, or smoke and carbon monoxide and motion only, or pollen and motion only, or noise pollution and pollen only, and so forth.

As shown, hazard detection system 305 may include an internal chamber space 303 that may be defined by an internal chamber body 302 to have any suitable size and/or shape. At least a portion of chamber space 303 may be a portion of enclosure space 301 (e.g., hazard detection system 305 may be at least partially or completely positioned within enclosure space 301). Chamber body 302 may include one or more openings, such as openings 304 and 304', that may be operative to allow at least certain fluid (e.g., air, smoke, etc.) to pass from an external space portion 301e of enclosure space 301 into chamber space 303 (e.g., which may be an internal space portion of enclosure space 301) and/or from chamber space 303 into external space portion 301e of enclosure space 301. Each opening 304 may be provided with any suitable baffles and/or may be sized or otherwise configured in any suitable manner for preventing other fluid from being communicated between chamber space 303 and external space portion 301e of enclosure space 301 (e.g., bugs, debris, etc.). Hazard detection system 305 may be an optical smoke sensing device, a photoelectric smoke sensing device, and/or the like. For example, hazard detection system 305 may be a photoelectric or optoelectronic smoke detector that may include various sensors, which may be similar to one or more sensors 220 of FIG. 2, such as a light emitting subsystem (LES) 350 and a light detecting subsystem (LDS) 380 that together may be utilized to detect the presence of smoke within chamber space 303 that may flow into chamber space 303 from a smoke source within external space portion 301e of enclosure space 301 (e.g., a nearby fire). As shown, light emitting subsystem 350 may include any suitable light emitting component (LEC) 352 (e.g., an optoelectronic emitter or an optoelectronic transmitter, such as a light emitting diode (LED) or the like) that may be operative to emit light L1 into space 303, while light detecting subsystem 380 may include any suitable light detecting component (LDC) 382 (e.g., an optoelectronic detector or an optoelectronic receiver, such as a light detecting diode (e.g., a photodiode), a phototransistor, a photoresistor, any other suitable photodetector, or the like) that may be operative to detect light L2 that may be at least a portion of emitted light L1 as deflected by smoke S (e.g., any suitable particle or particulate of fluid within chamber space 303 to be detected by hazard detection system 305 (e.g., a hazard particle, such as any type of smoke)). An axis of any emitted light from LEC 352 may be offset from an axis of any light detected by LDC 382 by an angle θ of any suitable amount, such as by 30°, so that light L1 emitted LEC 352 may not be readily detected by LDC 382 unless smoke S is within chamber space 303 (e.g., to scatter light emitted by LEC 352 towards LDC 382). Thus, for example, when particles of smoke S exist within space 303, light L1 emitted by a radiation source LEC 352 may be scattered by one or more of such particles, and, if the scattering is sufficient, a radiation detector LDC 382 can detect the scattered light as light L2. If relatively few or no smoke particles exist within space 303 when light L1 is emitted by LEC 352, then light L2 may not be sufficiently scattered to be detected by LDC 382 (e.g., an interior surface of internal chamber body 302 may absorb light L1 or otherwise be operative to prevent any portion of light L1 from directed towards LDC 382 unless by smoke S).

Light emitting subsystem 350 and light detecting subsystem 380 may be electrically coupled to a processor 315, which may be similar to processor 210 and/or processor 230 of FIG. 2, that may be provided on any suitable circuit board 306 and that may be running any suitable processor application 315a (e.g., any suitable firmware or software, etc.) that may be accessed from and/or used in conjunction with any suitable processor data 316d from any suitable memory 316 or other data source (e.g., a memory that may be similar to memory 216 of FIG. 2), such that, upon detecting the presence of smoke S (e.g., upon detecting suitable light L2 at LDC 382), an alarm 334, which may be similar to alarm 234 and/or speaker 218 of FIG. 2, may be triggered and/or such that other information may otherwise be communicated to components mounted on or otherwise electrically coupled with circuit board 306 for warning a user or other suitable entity. Various components may be mounted on circuit board 306. For example, internal chamber body 302 may be coupled with or mounted on circuit board 306 and configured to detect the presence of smoke. In one embodiment, internal chamber body 302 may be mid-mounted relative to circuit board 306 so that fluid may flow into chamber space 303 both from a portion of external space portion 301e of enclosure space 301 above circuit board 306 and from a portion of external space portion 301e of enclosure space 301 below circuit board 306. Processor 315, memory 316, and/or alarm 334 may also be mounted on or otherwise coupled to circuit board 306. Other components, such as a motion sensor, carbon monoxide sensor, and the like (not shown) may likewise be mounted on circuit board 306. Processor 315 may include any suitable processing components, such as one or more microprocessors and/or other processor related components (e.g., one or more analog to digital converters (ADCs), one or more digital to analog converters (DACs), etc.), that may be mounted on circuit board 306 or otherwise provided.

Figure 3A:
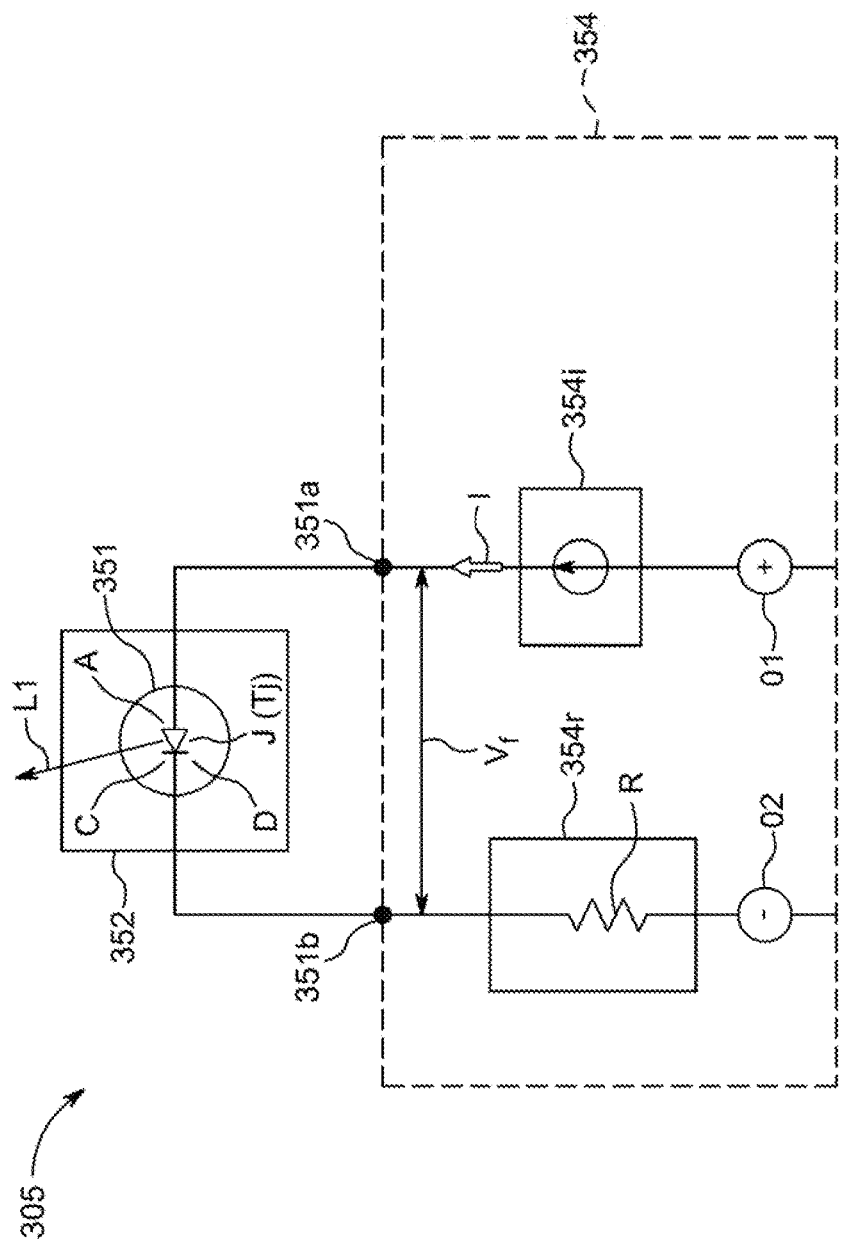

Light emitting subsystem 350 may include at least one light emitting component (LEC) 352. LEC 352 may be any suitable component (e.g., an optoelectronic component) that may be operative to emit light (e.g., light L1) therefrom, including, but not limited to a light emitting diode (LED) or any other suitable light-emitting or light-generating element or light-generating component that may operate with a forward voltage or voltage drop or forward voltage drop that may correlate with a temperature of the component. A power source of hazard detection system 305, which may not be shown in FIG. 3 but which may be similar to power source 240 of FIG. 2, may be configured to provide power to LEC 352 (e.g., via LEC circuitry (LECC) 354) for enabling the generation and emittance of light therefrom. In some embodiments, as shown in FIG. 3A, for example, LEC 352 may include any suitable light emitting element 351 (e.g., any suitable light emitting diode D) with at least two pins or nodes 351a and 351b that may be electrically coupled with LECC 354, which may include a first node O1 and a second node O2. As shown, a current (e.g., current I) may flow through LEC 352 (e.g., as may be enabled by a power supply coupled to nodes O1 and O2 of LECC 354 or as may be enabled by a current source component 354i of LECC 354). Moreover, in some embodiments, as shown in FIG. 3A, for example, LECC 354 may also include any resistance element 354r or combination of resistance elements (e.g., any suitable resistor R), which may be provided (e.g., in series with light emitting element 351) with a particular resistance for enabling an appropriate value for the operating current of LEC 352, such that light (e.g., light L1) may be emitted from a semiconductor junction J of light emitting element 351 (e.g., at the p-n junction of anode A and cathode C of light emitting diode D). A forward voltage $V_f$ of LEC 352 (e.g., of light emitting element 351) may be detected or otherwise measured (e.g., across nodes 351a and 351b) by LECC 354 (e.g., alone or in combination with any suitable processing by processor 315). Such a forward voltage $V_f$ of LEC 352 may correlate with the temperature of light emitting element 351 (e.g., temperature $T_j$ at semiconductor junction J of LED D), as described below in more detail. In some embodiments, LEC 352 may include any suitable light emitting element 351, which may be any suitable light-emitting diode, including, but not limited to, an inorganic light-emitting diode, an organic light-emitting diode, a high brightness light-emitting diode, a micro-light-emitting diode, a nano-light-emitting diode, and the like. In some embodiments, node O2 may be coupled to ground or any other suitable element. While FIG. 3A may show LECC 354 to include a high side current source (e.g., a current source component 354i may be coupled to anode A of LED D), LECC 354 may include a low side current sink (e.g., a current sink may be operative to pull current from light emitting element 351 (e.g., from cathode C of LED D)).

A forward voltage of LEC 352 of may be dependent on or otherwise correlate with the temperature of LEC 352 for a particular current flowing therethrough, such that detection of the forward voltage $V_f$ of LEC 352 may enable determination of the temperature of hazard detection system 305 at LEC 352. Processor 315 may be configured to enable the determination of and/or the use of the temperature of one or more light emitting components (e.g., LEC 352) of hazard detection system 305. For example, processor 315 (e.g., when running application 315a) may be operative to receive or otherwise detect from LECC 354 the current or most recent forward voltage $V_f$ of LEC 352, to access or otherwise determine any suitable forward voltage-temperature correlator data for that LEC 352 as a portion of processor data 316d from memory 316 or from any other suitable data source accessible to hazard detection system 305, and to use such a detected forward voltage $V_f$ in combination with such accessed forward voltage-temperature correlator data to determine the current temperature of that LEC 352. Such operations may be repeated by processor 315 at any suitable rate for continuously monitoring the current forward voltage of LEC 352, for example, by continuously receiving updated forward voltage data from LECC 354 and then using that forward voltage data with suitable correlator data for continuously determining the current temperature of LEC 352. Such a determined current temperature of LEC 352 may be used for one or more various purposes (e.g., to determine the ambient temperature of chamber space 303 and/or of external space portion 301e of enclosure space 301, to compensate for a temperature coefficient of the brightness of light emitted from LEC 352 and/or for a temperature coefficient of the brightness of light detected by any suitable LDC (e.g., LDC 382 and/or an LDC of light emitting subsystem 350), etc.).

Forward voltage data may be detected by and provided to processor 315 via any suitable circuitry or sensing apparatus coupled to LEC 352 (e.g., via nodes 351a and 351b (or otherwise) of LECC 354). Correlator data may be any suitable correlator that may be used to determine the current temperature of LEC 352 based on any value of a detected current forward voltage $V_f$ of LEC 352. For example, such correlator data of processor data 316d may be a look-up table with multiple distinct associations between a particular forward voltage of LEC 352 and a particular temperature, where processor 315 may be enabled to use a received detected forward voltage $V_f$ of LEC 352 to identify a particular appropriate association of the look-up table of the correlator data associated with LEC 352, and where processor 315 may then determine the particular temperature of that identified particular association of the look-up table to be used as the current temperature $T_j$ of LEC 352. As another example, such correlator data of processor data 316d may be a polynomial curve or equation or slope or data element that may approximate the dependence between the forward voltage of LEC 352 and the temperature of LEC 352 at various voltages/temperatures, where processor 315 may be enabled to use a received detected forward voltage $V_f$ of LEC 352 in combination with such a curve or equation or slope associated with LEC 352 to identify the appropriate temperature to be used as the current temperature $T_j$ of LEC 352.

Such correlator data of processor data 316d may be defined by a testing process carried out on LEC 352 prior to or after incorporating LEC 352 in hazard detection system 305 (e.g., a process during which LEC 352 may be positioned in an environment of a known temperature and then during which the forward voltage of LEC 352 may be measured and associated with that known temperature, and during which that sub-process may be repeated one or more times after altering the known or otherwise detectable temperature of the environment). Therefore, such correlator data associated with LEC 352 may include at least two pre-determined data sets of associated detected forward voltage $V_f$ and detected junction temperature $T_j$ of LEC 352, such that processor 315 may calculate an associated correlator slope m of LEC 352 (e.g., in ° Celsius/Volt) and such that, when a current forward voltage $V_f$ of LEC 352 may be detected by processor 315 during use of hazard detection system 305 in enclosure 300, processor 315 may use such a calculated slope m of LEC 352 in conjunction with that current forward voltage $V_f$ to determine the appropriate current junction temperature $T_j$ of LEC 352. Alternatively, such correlator data associated with LEC 352 may include such a slope m, such that, when a current forward voltage $V_f$ of LEC 352 may be detected by processor 315 during use of hazard detection system 305 in enclosure 300, processor 315 may use such a slope m of LEC 352 in conjunction with that current forward voltage $V_f$ to determine the appropriate current junction temperature $T_j$ of LEC 352. Alternatively, such correlator data associated with LEC 352 may include one pre-determined data set of associated detected forward voltage $V_f$ and detected junction temperature $T_j$ of LEC 352 as well as such a slope m of LEC 352, such that processor 315 may determine an appropriate current junction temperature $T_j$ of LEC 352 based on such correlator data and a current forward voltage $V_f$ of LEC 352. For example, the following equation (1) may be used by processor 315 to determine the current temperature of LEC 352:

$$T_{j\text{-}current} = V_{f\text{-}current} * m + (T_{j\text{-}x} - (V_{f\text{-}x} * m)), \quad (1)$$

where $T_{j\text{-}current}$ may be the current temperature of LEC 352 to be determined by processor 315 (e.g., in ° Celsius), where $V_{f\text{-}current}$ may be the current forward voltage of LEC 352 as may be provided to processor 315 by LECC 354 (e.g., via an ADC (not shown)), where $V_{f\text{-}x}$ may be a predetermined forward voltage of LEC 352 at a previous time X, where $T_{j\text{-}x}$ may be a predetermined temperature of LEC 352 at previous time X (e.g., where $T_{j\text{-}x}$ and $V_{f\text{-}x}$ may have been determined during a testing and/or assembly stage of system 305 (e.g., in a factory) and may be a portion of the correlator data of LEC 352 accessible by processor 315), and where in may be the associated correlator slope m of LEC 352 (e.g., in ° Celsius/Volt) of the correlator data of LEC 352 accessible by processor 315. Alternatively, rather than being a portion of the correlator data of LEC 352 accessible by processor 315, slope in may be determined by processor 315 by the following equation (2):

$$m = (T_{j\text{-}x} - T_{j\text{-}y}) / (V_{f\text{-}x} - V_{f\text{-}y}), \quad (2)$$

where $V_{f\text{-}y}$ may be a predetermined forward voltage of LEC 352 at a previous time Y different than time X, where $T_{j\text{-}y}$ may be a predetermined temperature of LEC 352 at previous time Y (e.g., where $T_{j\text{-}y}$ and $V_{f\text{-}y}$ may have been determined during a testing and/or assembly stage of system 305 and may be another portion of the correlator data of LEC 352 accessible by processor 315), where $V_{f\text{-}x}$ may be different than $V_{f\text{-}y}$, and where $T_{j\text{-}x}$ may be different than $T_{j\text{-}y}$. For example, in such embodiments, rather than slope in being predetermined or otherwise known for provisioning as a portion of the correlator data of LEC 352 accessible by processor 315, two distinct sets of previously determined forward voltage-temperature correlator data points for LEC 352 (e.g., $V_{f\text{-}x}$, $T_{j\text{-}x}$; and $V_{f\text{-}y}$, $T_{j\text{-}y}$) may be provided as at least a portion of the correlator data of LEC 352 accessible by processor 315 for use in determining the current temperature of LEC 352.

In some embodiments, in a factory setting or otherwise prior to defining such correlator data for LEC 352, at least a portion of hazard detection system 305 including LEC 352 may be held at a first temperature at a first moment in time (e.g., in a controlled environment of a factory that may be used for assembling and/or testing system 305) and the forward voltage of LEC 352 at that first temperature may be detected and stored with the value of that first temperature as respective values of correlator data for LEC 352 (e.g., correlator data values $V_{f\text{-}x}$ and $T_{j\text{-}x}$ at first moment in time X). Then, after that first moment in time, one or more components of hazard detection system 305 that had been off during the previous determination of values $V_{f\text{-}x}$ and $T_{j\text{-}x}$ of correlator data for LEC 352 may be turned on, whereby such one or more turned on components of system 305 may generate heat for changing the temperature of LEC 352 from that first temperature to a different second temperature at a second moment in time, such that the forward voltage of LEC 352 at that second temperature may be detected and stored with the value of that second temperature as respective values of correlator data for LEC 352 (e.g., correlator data values $V_{f\text{-}y}$ and $T_{j\text{-}y}$ at second moment in time Y). Such components of system 305 may be wireless communications circuitry (e.g., circuitry similar to circuitry 212 and/or circuitry 214 of system 205), such as Wi-Fi and/or Bluetooth circuitry, and/or any other suitable heat-generating components of system 305 that may be operative to change the temperature of LEC 352 when such one or more heat-generating components are activated. This process of collecting different forward voltage and temperature values of LEC 352 may enable any environment of system 305 to capture and define correlator data for LEC 352 even if the environment of system 305 is not able to alter the temperature of LEC 352 on its own, but instead may use the ability of system 305 itself to alter the temperature of LEC 352 by ramping up one or more heat generating components of system 305 for altering the temperature of LEC 352. In some embodiments, the various temperature data points (e.g., $T_{j\text{-}x}$ and $T_{j\text{-}y}$) may be determined using any suitable temperature sensor(s), such as a temperature sensor that may be proximate to LEC 352 during such a process (e.g., a temperature sensor of the assembly and/or manufacturing environment) and/or permanently (e.g., a temperature sensor of system 305 (e.g., a temperature sensor of an LEC temperature sensor subsystem (TSLEC) 360, as described below in more detail)).

Alternatively, rather than using correlator data for LEC 352 that may include one predetermined data set of detected forward voltage and temperature of LEC 352 and a polynomial curve or equation or slope that may approximate the dependence between the forward voltage of LEC 352 and the temperature of LEC 352 at various voltages/temperatures and/or rather than using correlator data for LEC 352 that may include two predetermined data sets of detected forward voltage and temperature of LEC 352 in combination with a detected current forward voltage of LEC 352 so as to determine a current temperature of LEC 352, hazard detection system 305 may be operative to vary the amount of current I flowing through LEC 352 and to detect correspondingly varying amounts of forward voltage of LEC 352 in order to determine the current temperature of LEC 352. For example, as shown in FIG. 3A, the amount of current I that may flow through LEC 352 may be dictated by current source component 354i of LECC 354 and/or by any other suitable manner (e.g., by a power supply coupled to any suitable nodes of LECC 354). As just one example, within a certain duration of time during which the temperature of LEC 352 may not be able to vary by more than a certain minimal amount (e.g., the duration of time between time t2 and time t4 of diagram 400 of FIG. 4), not only may a first magnitude of current I (e.g., a first magnitude current $I_1$) be injected into LEC 352 at a first moment such that the magnitude of the forward voltage of LEC 352 (e.g., a first forward voltage $V_{f1}$) may be detected at that first moment, but also a second magnitude of current I (e.g., a second magnitude current $I_2$) may then be injected into LEC 352 at a second moment such that the magnitude of the forward voltage of LEC 352 (e.g., a second forward voltage $V_{f2}$) may be detected at that second moment, all while the current temperature $T_{j\text{-}current}$ of LEC 352 may remain substantially or completely constant. Through such a process, processor 315 may be operative to determine that current temperature $T_j$ of LEC 352 (i.e., $T_{j\text{-}current}$) without using any particular predetermined correlator data for LEC 352 but instead by using the following equation (3):

$$T_{j\text{-}current} = ((((V_{f1} - V_{f2})/(\text{natural log of}(I_1/I_2)))*q)/(n*k)) + T_{j\text{-}x}, \quad (3)$$

where $V_{f1}$ may be the detected forward voltage of LEC 352 (e.g., as may be made available to processor 315 by LECC 354) when current I of a known magnitude $I_1$ is injected into LEC 352 (e.g., by LECC 354), where $V_{f2}$ may be the detected forward voltage of LEC 352 (e.g., as may be made available to processor 315 by LECC 354) when current I of a known magnitude $I_2$ different from known magnitude $I_1$ is injected into LEC 352 (e.g., by LECC 354), where q may be the known magnitude of charge of an electron (e.g., the elementary charge (i.e., $1.6021766208 \times 10^{-19}$ coulombs)), where n may be an appropriate ideality factor or quality factor or emission coefficient of diode D of element 351 of LEC 352 (e.g. between 1.0 and 2.0), where k may be the Boltzmann constant (i.e., $1.38064852 \times 10^{-23}$ joules per kelvin), and where $T_{j\text{-}x}$ may be a predetermined temperature of LEC 352 at a previous time X (e.g., where $T_{j\text{-}x}$ may have been determined during a testing and/or assembly stage of system 305 (e.g., in a factory) and may be a portion of the correlator data of LEC 352 accessible by processor 315). The minimum timing between the measurement of $V_{f1}$ and $V_{f2}$ may be determined using any suitable variables or characteristics of the system. For example, one, some, or all of the following variables may be weighed to determine the minimum timing, such as (i) the temperature shift that may occur from the first current pulse (e.g., when current $I_1$ is injected), (ii) the rate of change of the ambient temperature, and/or (iii) the rate of change of the temperature on board 306 or elsewhere (e.g., due to system self-heating). As an example, the second measurement (i.e., of $V_{f2}$) may be taken at least five (or any other suitable number of) intervals of a time constant TC after the first measurement is taken (i.e., of $V_{f1}$), such that the temperature of LEC 352 may have settled back close to its original temperature before the first current pulse. Time constant TC may be measured empirically or one or more thermal variables of LEC 352 (e.g., Rja and/or Cj) may be gathered and used to calculate an adequate time constant TC. As an example, time constant TC may be on the order of or less than hundreds of milliseconds. The time constant of the self-heating of circuit board 306 may be at least somewhat controlled (e.g., in the design phase), but may be ensured to be longer than time constant TC, and the rate of change of the ambient temperature may be slow such that it may be ignored or minimally weighted. In some embodiments, current source component 354i of LECC 354 may include a switch that may be operative to be switched between a first position at which a first current source of magnitude $I_1$ is coupled to node 351a of LEC 352 and a second position at which a second current source of magnitude $I_2$ is coupled to node 351a of LEC 352, where such a switch may be controlled by processor 315 in conjunction with processor 315 acquiring different detected magnitudes of the forward voltage of LEC 352 for properly determining the current temperature of LEC 352 (e.g., temperature $T_{j\text{-}current}$ using equation (3)). Alternatively or additionally, processor 315 may be operative to couple different power supplies or different amounts of power to LEC 352 (e.g., to node O1 of LECC 354) for varying the magnitude of the current injected into LEC 352. Alternatively or additionally, circuitry 356 of FIG. 3C may be used for varying the magnitude of the current injected into LEC 352.

Figure 3B:
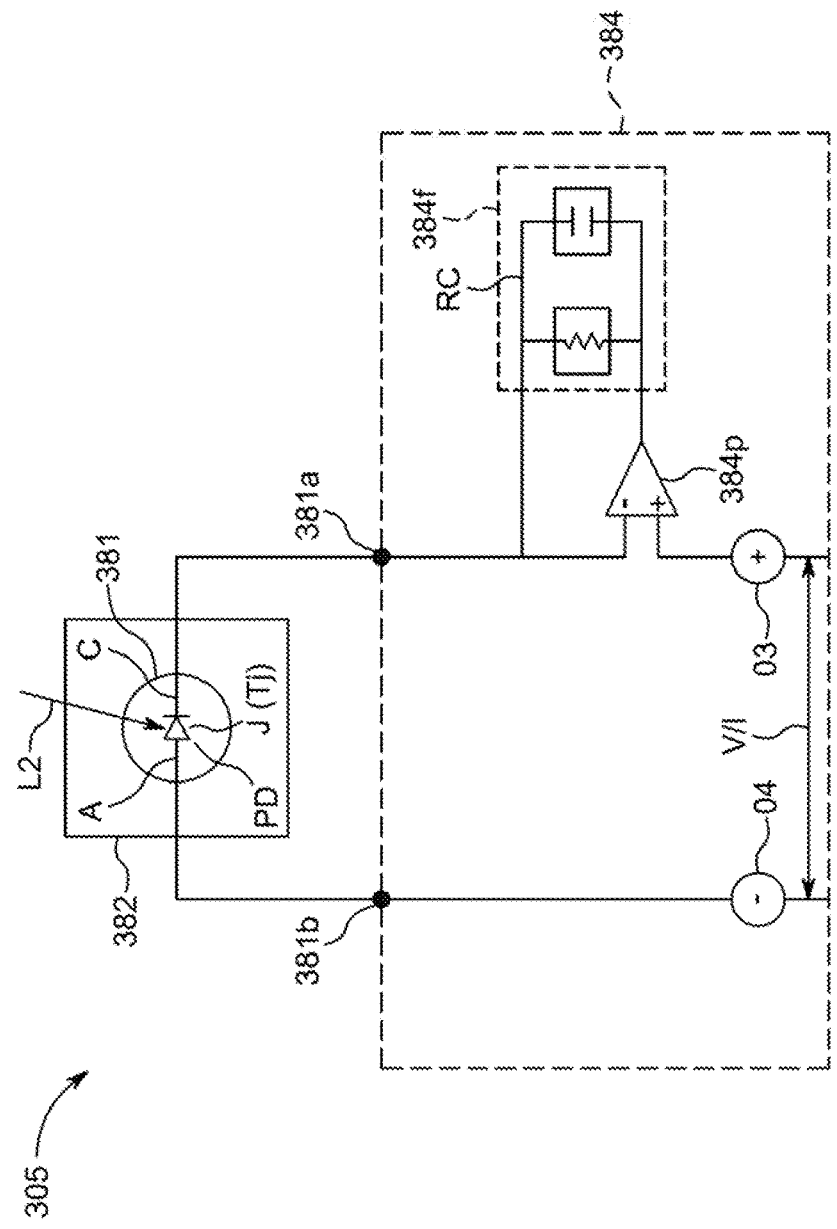

Therefore, the current temperature of LEC 352 (e.g., the current temperature $T_{j\text{-}current}$ of light emitting element 351 (e.g., any suitable light emitting diode D) of LEC 352 of FIG. 3A) may be determined by processor 315 of hazard detection system 305 through using the relationship between a voltage of a diode of LEC 352 and the temperature of that diode of LEC 352 (e.g., through processing both a detected current forward voltage of LEC 352 and any suitable predetermined correlator data of LEC 352 or by processing two detected forward voltages of LEC 352 when two known magnitudes of current are injected into LEC 352 (e.g., within a certain period of time (e.g., without any predetermined correlator data of LEC 352) or otherwise)). Additionally or alternatively, the current temperature of LDC 382 (e.g., the current temperature $T_{j\text{-}current}$ of a light detecting element 381 (e.g., any suitable light detecting diode PD (e.g., a photodiode)) of LDC 382 of FIG. 3B) may be determined by processor 315 of hazard detection system 305 through using the relationship between a voltage or a current of a diode of LDC 382 and the temperature of that diode of LDC 382 (e.g., through processing both a detected current voltage or current of LDC 382 (e.g., using any suitable LDC circuitry (LDCC) 384) and any suitable predetermined correlator data of LDC 382 or by processing two detected voltages or currents of LDC 382 when two known magnitudes of current or voltage are injected into or applied across LDC 382 (e.g., within a certain period of time (e.g., without any predetermined correlator data of LDC 382) or otherwise)). A power source of hazard detection system 305, which may not be shown in FIG. 3 but which may be similar to power source 240 of FIG. 2, may be configured to provide power to LDC 382 (e.g., via LDCC 384) for enabling the detection of light L2. In some embodiments, as shown in FIG. 3B, for example, LDC 382 may include any suitable light detecting element 381 (e.g., any suitable light detecting diode PD (e.g., a photodiode)) with at least two pins or nodes 381a and 381b that may be electrically coupled with LDCC 384, which may include a first node O3 and a second node O4. A voltage of LDC 382 may be applied or measured across nodes O3 and O4. For example, light detecting element 381 may be biased (e.g., reverse biased) with an external voltage V (e.g., a calibration power characteristic value of voltage V of light detecting element 381), during which incoming detected light L2 may increase the current (e.g., reverse current) flowing through light detecting element 381, and such a magnitude of such current may be detected (e.g., by LDCC 384) for determining a current brightness of light L2 (e.g., light detecting element 381 itself may not be generating energy but may be modulating the flow of energy from an external source, where such a mode may be referred to as a photoconductive mode). A magnitude of a current flowing through LDC 382 (e.g., as may be varied by the magnitude of light L2 detected by diode PD of light detecting element 381 of LDC 382 when voltage V is applied across element 381 (e.g., at a semiconductor junction J of light detecting element 381 (e.g., at a junction of anode A and cathode C of light detecting diode PD))) may be detected by LDCC 384 in any suitable manner (e.g., using any suitable circuitry components of LDCC 384), and such a detected magnitude of current may be used by processor 315 (e.g., to determine the temperature $T_{j-current}$ of light detecting diode PD of LDC 382 using any suitable technique (e.g., using one or more of equations (1)-(3)) and/or to determine a smoke condition of system 305). As another example, in the absence of external bias, light detecting element 381 may be operative to convert the energy of light L2 into electric energy by charging the terminals of light detecting element 381 to a voltage, whereby the rate of charge (e.g., as may be detected by LDCC 384) may be proportional to the intensity or brightness of incoming light L2 (e.g., the energy may be harvested and measured by draining the charge through an external high-impedance path (e.g., of LDCC 384), where such a mode may be referred to as a photovoltaic mode). As just one particular embodiment of circuitry 384, as shown in FIG. 3B, circuitry 384 may include a transimpedance amplifier or any other suitable component, which may include an amplifier component 384p, where an inverting input of amplifier component 384p may be coupled to node 381a, a non-inverting input of amplifier component 384p may be coupled to node O3, and the output of amplifier component 384p may be coupled to the inverting input of amplifier component 384p and to cathode C of light detecting element 381 via a filter component 384f, which may include a resistor-capacitor circuit RC. A voltage V (e.g., a constant voltage) may be applied to node O3 and a current through light detecting element 381 may be detected or a voltage of circuitry 384 may be detected that may be proportional to the current through light detecting element 381. For example, such a current or voltage may be detected when no light is being detected by light detecting element 381 (e.g., between times t1 and t2 described below) to determine the temperature of LDC 382 (e.g., using an equation similar to equation (1)).

Such determination of the current temperature of LEC 352 and/or of the current temperature of LDC 382 may be utilized by hazard detection system 305 in one or more various ways for effectively handling temperature variation within hazard detection system 305. For example, in some embodiments, such a determination of the current temperature of LEC 352 and/or of the current temperature of LDC 382 without the use of any distinct temperature sensor (e.g., one or more thermistors) in internal chamber space 303 may provide one or more of a number of benefits. For example, determining the current temperature of LEC 352 and/or the current temperature of LDC 382 without the use of an independent temperature sensor (e.g., temperature sensor (TS) 308 of FIG. 3) in internal chamber space 303 may reduce the bill of materials cost of system 305, may enable the size and/or shape of internal chamber space 303 to be smaller and/or different, and/or may obviate the need for a distinct temperature sensor within a flow path of smoke S within chamber space 303 that may be prone to breaking and/or to disrupting the flow of smoke 5, while still enabling the detection of a temperature of a location within chamber space 303.

While the current temperature $T_{current}$ of LEC 352 may be determined through using a first temperature coefficient of a diode of LEC 352 (e.g., a relationship between a forward voltage $V_f$ and a temperature $T_j$ of LED D of LEC 352) rather than through using a dedicated temperature sensor, it is to be understood that any suitable dedicated temperature sensor (e.g., a thermistor) may instead or additionally be used to determine the current temperature of LEC 352. For example, as shown in FIG. 3, hazard detection system 305 may include an LEC temperature sensor subsystem (TSLEC) 360 (e.g., as a portion of light emitting subsystem 350) that may include at least one dedicated LEC temperature sensor (TSLE) (e.g., at least one thermistor or any other suitable temperature sensing component) for detecting the temperature of LEC 352. As shown, TSLEC 360 may include at least one of TSLE 362 (e.g., a thermistor or diode or any other suitable temperature sensing component that may be thermally coupled to LEC 352 and that may be provided on the same die 353 as LEC 352 (e.g., at least partially within space 303)), TSLE 364 (e.g., a thermistor or diode or any other suitable temperature sensing component that may be thermally coupled to LEC 352 and provided (e.g., bonded) on the same chip carrier or package 355 as die 353 of LEC 352 (e.g., at least partially within space 303) but not on die 353), TSLE 366 (e.g., a thermistor or diode or any other suitable temperature sensing component that may be thermally coupled to LEC 352 and that may be provided at least partially within chamber space 303 but not on package 355 of LEC 352), and/or TSLE 368 (e.g., a thermistor or diode or any other suitable temperature sensing component that may be thermally coupled to LEC 352 but provided outside of chamber space 303 (e.g., on board 306)). Any node(s) of one, some, or all TSLEs of TSLEC 360 may be electrically coupled to any suitable TSLE circuitry (TSLECC) 369 that may be operative to enable the detection of the temperature of such one or more TSLE(s) by processor 315. Additionally or alternatively, while the current temperature of LDC 382 may be determined through using a first temperature coefficient of a diode of LDC 382 (e.g., a relationship between a voltage or current and a temperature $T_j$ of photodiode PD of LDC 382) rather than through using a dedicated temperature sensor, it is to be understood that any suitable dedicated temperature sensor (e.g., a thermistor) may instead or additionally be used to determine the current temperature of LDC 382. For example, as shown in FIG. 3, hazard detection system 305 may include an LDC temperature sensor subsystem (TSLDC) 390 (e.g., as a portion of light detecting subsystem 380) that may include at least one dedicated LDC temperature sensor (TSLD) (e.g., at least one thermistor or any other suitable temperature sensing component) for detecting the temperature of LDC 382. As shown, TSLDC 390 may include at least one of TSLD 392 (e.g., a thermistor or any other suitable temperature sensing component that may be thermally coupled to LDC 382 and that may be provided on the same die 383 as LDC 382 (e.g., at least partially within space 303)), TSLD 394 (e.g., a thermistor or any other suitable temperature sensing component that may be thermally coupled to LDC 382 and that may be provided on the same chip carrier or package 385 as die 383 of LDC 382 (e.g., at least partially within space 303) but not on die 383), TSLD 396 (e.g., a thermistor or any other suitable temperature sensing component that may be thermally coupled to LDC 382 and that may be provided at least partially within chamber space 303 but not on package 385 of LDC 382), and/or TSLD 398 (e.g., a thermistor or any other suitable temperature sensing component that may be thermally coupled to LDC 382 but provided outside of chamber space 303 (e.g., on board 306)). Any node(s) of one, some, or all TSLDs of TSLDC 390 may be electrically coupled to any suitable TSLD circuitry (TSLDCC) 399 that may be operative to enable the detection of the temperature of such one or more TSLD(s) by processor 315. Any TSLE of TSLEC 360 and/or any TSLD of TSLDC 390 may be any suitable temperature sensor (e.g., a thermistor, thermocouple, thermometer, silicon bandgap temperature sensor, bimetal sensor, etc.) for detecting the temperature of LEC 352 or LDC 382, respectively. Thermistors can include negative temperature coefficient (NTC) type thermistors and/or positive temperature coefficient (PTC) type thermistors.

Detection of a temperature of any suitable location within chamber space 303 (e.g., at the location of LEC 352 and/or the location of LDC 382 within or proximal space 303) using any suitable techniques (e.g., by using a relationship between a voltage and temperature of a diode of LEC 352 and/or LDC 382 and/or by using one or more dedicated temperature sensors thermally coupled to or adjacent LEC 352 and/or LDC 382) may be utilized for determining the temperature of any smoke S within chamber space 303 and/or for determining the temperature of external space portion 301e of enclosure space 301 that may be distinct from chamber space 303 but that may be thermally coupled with chamber space 303 (e.g., due to opening(s) 304, whereby the temperature of fluid within space 303 may have the same or a similar or related temperature to fluid outside of space 303 within external space portion 301e of space 301 adjacent or near an opening 304, and whereby LEC 352 and/or LDC 382 may be well thermally coupled with space 303 for emitting light into and/or detecting light within space 303). Any suitable thermal resistance data and/or thermal conductance data (e.g., a portion of processor data 316d) that may be predetermined with respect to the temperature of LEC 352 and/or LDC 382 and the temperature of any other suitable location (e.g., any location of system 305 or of enclosure 300) such that the temperature of that other location (e.g., location N1 within chamber space 303 and/or location N2 within external space portion 301e of enclosure space 301 but not chamber space 303) may be determined using that thermal resistance/conductance data (e.g., any suitable thermal resistance/conductance data, such as air flow data, a linear model, thermal coupling constant(s), etc. (e.g., as may be determined during calibration of system 305)) and the detected temperature of LEC 352 and/or the detected temperature of LDC 382 (e.g., either the detected temperature of LEC 352 or the detected temperature of LDC 382 may be used in combination with any thermal resistance/conductance data to determine the temperature of one or more suitable locations of space 301, or both the detected temperature of LEC 352 and the detected temperature of LDC 382 may be used in combination with any thermal resistance data to determine the temperature of one or more suitable locations of space 301). In some embodiments, no thermal resistance data may be used or the thermal resistance data may be equal to zero when the temperature of LEC 352 and/or the temperature of LDC 382 may be used as the ambient temperature to be determined (e.g., as LEC 352 and/or LDC 382 may be well thermally coupled to the location of the ambient temperature due to the flow of fluid through space 303). Alternatively, thermal resistance data may be any suitable data that may be operative to determine an ambient temperature by processing the temperature of LEC 352 and/or the temperature of LDC 382 in combination with any other suitable data or in any suitable manner. For example, the thermal resistance data may be determined empirically, such as at least partially during calibration and using one or more temperature sensors in the ambient environment. A coefficient matrix (e.g., a time-varying matrix of values and coefficients) as may be determined empirically or in simulation may be used (e.g., with a time lag coefficient for one or more components that may have its temperature determined). Airflow through chamber 303 may be determined by comparing the difference in temperature (e.g., temperature gradient) between the determined temperatures of different components at different locations within chamber 303 (e.g., the difference between the temperature of LEC 352 and the temperature of LDC 382), either over time or at a particular moment, and may determine air flow accordingly.

Any suitable determination of the current temperature of LEC 352 and/or of the current temperature of LDC 382 may alternatively or additionally be utilized by hazard detection system 305 to compensate for a temperature coefficient of LEC 352 and/or of LDC 382, respectively, for enabling hazard detection system 305 to more accurately detect hazard conditions despite variations in temperature within hazard detection system 305 (e.g., within chamber space 303). For example, the temperature coefficient (TCLEC) of the brightness of light L1 emitted from LEC 352 when a certain current (e.g., current I of FIG. 3A) is injected into LEC 352 may be any suitable amount (e.g., about −0.8%/° Celsius) and, if such a temperature coefficient does not vary by a particular amount with temperature, then the following linear approximation equation (4) may be used to determine the current brightness of emitted light L1:

$$B_{LEC\_current} = B_{LEC\_x} * (1 + (\alpha * T_{LEC\_current}) - (\alpha * T_{LEC\_x})), \quad (4)$$

where $B_{LEC\_current}$ may be the current brightness of light L1 emitted from LEC 352 when a particular current I is injected into LEC 352 while the current temperature of LEC 352 is $T_{LEC\_current}$, where $\alpha$ is the brightness temperature coefficient TCLEC of LEC 352 (e.g., for that particular current), and where $B_{LEC\_x}$ is the predetermined brightness of light L1 emitted from LEC 352 when the same particular current I is injected into LEC 352 while the temperature of LEC 352 is $T_{LEC\_x}$. Such values for $B_{LEC\_x}$, $T_{LEC\_x}$, the particular current I, and $\alpha$ may be predetermined (e.g., during calibration or testing of system 305) and may be made available to processor 315 (e.g., as a portion of processor data 316d associated with the temperature coefficient of LEC 352, for example, as a calibration brightness detected at a calibration temperature using a calibration current for a determined brightness temperature coefficient of an LED of LEC 352). For example, $\alpha$ may be any suitable value, such as −0.8%/° Celsius, and may vary between different LECs (e.g., between different LEDs). The value for the current temperature $T_{LEC\_current}$ of LEC 352 may be determined in any suitable manner, such as by using a local temperature sensor of TSLEC 360 or a relationship between the forward voltage of LEC 352 and its temperature (e.g., a temperature coefficient of the voltage of an LED of LEC 352, as described above), such that processor 315 may be operative to use equation (4) to determine $B_{LEC\_current}$ (i.e., to determine the actual brightness of light L1 emitted from LEC 352 at a particular determined current temperature $T_{LEC\_current}$ of LEC 352 when a particular current I is injected into LEC 352). Alternatively, a look-up table for LEC 352 may be provided (e.g., as at least a portion of processor data 316d) that may be used by processor 315 to determine $B_{LEC\_current}$ of light L1 for a detected $T_{LEC\_current}$ of LEC 352 and a particular current I of LEC 352.

As another example, the temperature coefficient (TCLDC) of the output level of the brightness of light L2 detected by LDC 382 when a certain voltage is applied across LDC 382 may be any suitable amount (e.g., about +0.1%/° Celsius) and, if such a temperature coefficient does not vary by a particular amount with temperature, then the following linear approximation equation (5) may be used to determine the current brightness of emitted light L1:

$$B_{LDC\_current} = B_{LDC\_x} * (1 + (\gamma * T_{LDC\_current}) - (\gamma * T_{LDC\_x})), \quad (5)$$

where $B_{LDC\_current}$ may be the current output level of the brightness of light L2 detected by LDC 382 when a particular voltage is applied across LDC 382 while the current temperature of LDC 382 is $T_{LDC\_current}$, where γ is the brightness temperature coefficient TCLDC of LDC 382, where $B_{LDC\_x}$ is the predetermined output level of the brightness of light L2 detected by LDC 382 when the same voltage is applied across LDC 382 while the temperature of LDC 382 is $T_{LDC\_x}$. Such values for $B_{LDC\_x}$, $T_{LDC\_x}$, the particular voltage supplied to LDC 382, and γ may be predetermined (e.g., during calibration or testing of system 305) and may be made available to processor 315 (e.g., as a portion of processor data 316d associated with the temperature coefficient of LDC 382). For example, γ may be any suitable value, such as 0.1%/° Celsius. and may vary between different LDCs (e.g., between different photodiodes). The value for the current temperature $T_{LDC\_current}$ of LDC 382 may be determined in any suitable manner, such as by using a local temperature sensor of TSLDC 390 or a relationship between the voltage or current of LDC 382 and its temperature (e.g., a temperature coefficient of the voltage or current of a photodiode of LDC 382, as described above) or $T_{LDC\_current}$ of LDC 382 may be assumed to be the same as $T_{LEC\_current}$ of LEC 352 or the same as $T_{LDCL\_current}$ of any LDCL of DSLEC 370 or the same as any other current temperature of any other component within space 303 that may be determined in any suitable manner, such that processor 315 may be operative to use equation (5) to determine $B_{LDC\ current}$ (i.e., to determine the actual brightness of light L2 detected by LDC 382 at a particular determined current temperature of LDC 382 when a particular voltage is applied to LDC 382). Alternatively, a look-up table for LDC 382 may be provided (e.g., as at least a portion of processor data 316d) that may be used by processor 315 to determine $B_{LDC\_current}$ for a detected $T_{LDC\_current}$ of LDC 352 and a particular voltage of LDC 382.

Therefore, determination of the current temperature $T_{LEC\_current}$ of LEC 352 may be utilized by processor 315 to determine the actual brightness $B_{LEC\_current}$ of light L1 emitted by LEC 352 despite any variation in the current temperature of LEC 352 by compensating for that current temperature using appropriate correction temperature coefficient data (e.g., TCLEC) and/or determination of the current temperature $T_{LDC\_current}$ of LDC 382 may be utilized by processor 315 to determine the actual brightness $B_{LDC\_current}$ of light L2 detected by LDC 382 despite any variation in the current temperature of LDC 382 by compensating for that current temperature using appropriate correction temperature coefficient data (e.g., TCLDC). Look-up tables with specific associations between LEC temperature and LEC emitted light brightness and/or with specific associations between LDC temperature and LDC detected light brightness may be accessible by processor 315 (e.g., if the brightness temperature coefficient of LEC 352 and/or of LDC 382 does vary by a particular amount with temperature such that a linear approximation equation may not be used). Such determination of the actual brightness $B_{LEC\_current}$ of light L1 emitted by LEC 352 and the actual brightness $B_{LDC\_current}$ of light L2 detected by LDC 382 may be necessary for processor 315 to accurately determine the amount of smoke S within chamber space 303 that is deflecting at least a portion of light L1 to LDC 382 as light L2. Any suitable brightness temperature coefficient data associated with LEC 352 and/or with LDC 382 may be accessed by processor 315 (e.g., as a portion of processor data 316d) for determining the actual brightness of light L1 for a detected current temperature of LEC 352 and/or for determining the actual brightness of light L2 for a detected current temperature of LDC 382, and any suitable smoke density processing may be used by processor 315 in combination with such actual brightness information to determine the current density of smoke S within chamber space 303 (e.g., a signal value representing a physical quantity of smoke within chamber space 303 detected by the photoelectric sensing of system 305), and any suitable alarm threshold data (e.g., as another portion of processor data 316d) may be utilized by processor 315 for determining in conjunction with the determined smoke density whether or not any suitable alarm may be initiated or terminated (e.g., using alarm 334).

Hazard detection system 305 may be calibrated according to a specific set of reference values. For example, during calibration, a particular calibration temperature (e.g., $T_x$ or $T_{LEC\_x}$ or $T_{LDC\_x}$) may be maintained within space 303 (e.g., at subsystem 350 and at subsystem 380) and particular calibration power characteristic(s) may be used for the operation of subsystems 350 and 380 (e.g., a particular current I may be injected into LEC 352 for enabling its operation and/or a particular voltage may be utilized by LDC 382 for enabling its operation), such that a consistent brightness of light L1 (e.g., a particular calibration brightness characteristic) may be emitted by LEC 352 while different magnitudes of brightness of light L2 may be detected at LDC 382 when different known amounts of smoke S are within space 303. Such magnitudes of detected brightness L2 or associated LDC values (e.g., voltage value(s) output by LDCC 384), which may be referred to as $LDSO_{detected}$, may be associated with respective known amounts of smoke S or respective alarm states associated with such known amounts of smoke S in any suitable data structure accessible to system 305 (e.g., as a portion of data 316d) during such calibration of system 305. In some embodiments, for a particular smoke condition, $LDSO_{detected}$ may be equal to $LDSO_{light} - LDSO_{dark}$, where $LDSO_{light}$ may be an output of light detecting subsystem 380 when LEC 352 is not emitting any light L1 during the particular smoke condition, and where $LDSO_{dark}$ may be an output of light detecting subsystem 380 when LEC 352 is emitting light L1 during the particular smoke condition, each of which may be determined while the particular calibration power characteristic(s) are used (e.g., while a particular current I is injected into LEC 352 to emit light L1 and/or while a particular voltage is applied to LDC 382 to enable measurement of a magnitude of current generated by LDC 382 when certain light L2 is detected (e.g., at LDCC 384)). Such a data structure of data 316d associating detected output(s) $LDSO_{detected}$ of light detecting subsystem 380 with particular known smoke conditions (e.g., a table of light-smoke correlation data) may be used by system 305 (e.g., by processor 315) during use of system 305 in the field for identifying a particular current smoke condition based on a detected current particular output $LDSO_{detected}$ of light detecting subsystem 380. If the temperature within space 303 did not change from the particular calibration temperature throughout the use of system 305, then determination of a particular smoke condition might be achieved by simply using a detected output $LDSO_{detected}$ of light detecting subsystem 380 in combination with that light-smoke correlation data. However, variation of temperature from the particular calibration temperature does occur during different use cases of system 305 and such temperature variation may affect one or more components of system 305 and, thus, may affect the sensitivity of system 305 to detect different smoke conditions. Therefore, the effect of temperature variation from the particular calibration temperature on one or more components of system 305 ought to be taken into account when determining a current smoke condition.

Any suitable data detection may be enabled and carried out by system 305 to determine a current smoke condition while effectively accounting for temperature-variation. For example, the following equation (6) may be used to determine a temperature-compensated output of light detecting subsystem 380 that may be effectively used by processor 315 in combination with previously determined light-smoke correlation data for determining a current smoke condition:

$$LDSO_{TC}=LDSO_{detected}-TE_{LEC}-TE_{LDC}-TE_{other}, \quad (6)$$

where $LDSO_{TC}$ may be a temperature-compensated output value of light detecting subsystem 380 for a particular smoke detection cycle of system 305 that may be used by processor 315 (e.g., rather than a non-compensated output value $LDSO_{detected}$) in combination with previously determined light-smoke correlation data for determining a current smoke condition of the particular cycle, where $LDSO_{detected}$ may be a detected output of light detecting subsystem 380 during the particular cycle that has not been compensated for any temperature variance from the particular calibration temperature of system 305, where $TE_{LEC}$ may be an effect of a current temperature of LEC 352 during the particular cycle on the determination of the current smoke condition of the particular cycle, where $TE_{LDC}$ may be an effect of a current temperature of LDC 382 during the particular cycle on the determination of the current smoke condition of the particular cycle, and where $TE_{other}$ may be an effect of a current temperature of any other component(s) of system 305 during the particular cycle on the determination of the current smoke condition of the particular cycle (e.g., a component of a subsystem 370, a component of a subsystem 350', and/or the like).

In some embodiments, $LDSO_{detected}$ for a particular cycle may be determined using the following equation:

$$LDSO_{detected}=LDSO_{light}-LDSO_{dark}, \quad (7)$$

where $LDSO_{light}$ may be an output of light detecting subsystem 380 when LEC 352 is not emitting any light L1 during a portion of the particular cycle, and where $LDSO_{dark}$ may be an output of light detecting subsystem 380 when LEC 352 is emitting light L1 during a portion of the particular cycle. For example, in order to detect the presence of smoke, a process may poll light detecting subsystem 380 (e.g., LDCC 384) on a periodic basis (e.g., every cycle) and obtain a "light" reading and a "dark" reading (e.g., every cycle) to calculate a sensor value for that cycle. The "light" reading may represent a raw analog-to-digital (ADC) reading obtained from light detecting subsystem 380 when its associated light source (e.g., LDC 352 of light emitting subsystem 350) is turned ON. The "dark" reading may represent a raw analog-to-digital (ADC) reading obtained from light detecting subsystem 380 when its associated light source (e.g., LDC 352 of light emitting subsystem 350) is turned OFF. The sensor value for the cycle may be calculated by subtracting the "dark" reading from the "light" reading.

$TE_{LEC}$ may be calculated using the following equation:

$$TE_{LEC}=K_{LEC}*(T_{LEC\_current}-T_{LEC\_x}), \quad (8)$$

where $K_{LEC}$ may be any suitable brightness temperature coefficient data associated with LEC 352 (e.g., temperature gain coefficient or brightness temperature coefficient TCLEC α of LEC 352), where $T_{LEC\_current}$ may be a current temperature of LEC 352 during the particular cycle, and where $T_{LEC\_x}$ may be the calibration temperature of LEC 352. Such values for $K_{LEC}$ and $T_{LEC\_x}$ may be predetermined (e.g., during calibration or testing of system 305) and may be made available to processor 315 (e.g., as a portion of processor data 316d associated with the temperature coefficient of LEC 352), while the current temperature $T_{LEC\_current}$ of LEC 352 during the particular cycle may be determined in any suitable manner (e.g., using one or more of equations (1)-(3) or any suitable TSLE(s) of TSLEC 360).

Similarly, in some embodiments, $TE_{LDC}$ may be calculated using the following equation:

$$TE_{LDC}=K_{LDC}*(T_{LDC\_current}-T_{LDC\_x}), \quad (9)$$

where $K_{LDC}$ may be any suitable brightness temperature coefficient data associated with LDC 382 (e.g., temperature gain coefficient or brightness temperature coefficient TCLDC γ of LDC 382), where $T_{LDC\_current}$ may be a current temperature of LDC 382 during the particular cycle, and where $T_{LDC\_x}$ may be the calibration temperature of LDC 382. Such values for $K_{LDC}$ and $T_{LDC\_x}$ may be predetermined (e.g., during calibration or testing of system 305) and may be made available to processor 315 (e.g., as a portion of processor data 316d associated with the temperature coefficient of LDC 382), while the current temperature $T_{LDC\_current}$ of LDC 382 during the particular cycle may be determined in any suitable manner (e.g., using one or more of equations (1)-(3) or any suitable TSLE(s) of TSLDC 390).

Additionally or alternatively, in some embodiments, $TE_{other}$ may be calculated using the following equation:

$$TE_{other}=K_{other}*(T_{other\_current}-T_{other\_x}), \quad (10)$$

where $K_{other}$ may be any suitable temperature gain coefficient or brightness temperature coefficient data associated with any other component of system 305, where $T_{other\_current}$ may be a current temperature of that other component during the particular cycle, and where $T_{other\_x}$ may be the calibration temperature of that other component. Such values for $K_{other}$ and $T_{other\_x}$ may be predetermined (e.g., during calibration or testing of system 305) and may be made available to processor 315 (e.g., as a portion of processor data 316d associated with the temperature coefficient of that other component), while the current temperature $T_{other\_current}$ of that other component during the particular cycle may be determined in any suitable manner (e.g., using one or more of equations (1)-(3) or any suitable temperature sensors proximate or thermally coupled to that other component). Such another component may be, for example, a LEC of another light emitting subsystem (e.g., LEC 352' of light emitting subsystem 350'), an LDC that may be optically coupled to LEC 352 (e.g., any LDCL component of subsystem 370), and/or any other suitable component that may have an effect on the detection of a smoke condition when its temperature varies from its calibration temperature. For example, equation (6) may include zero instances of $TE_{other}$ when no other components besides LDC 352 and LDC 382 are to be factored into a temperature compensated output $LDSO_{TC}$ for a particular cycle, a single instance of $TE_{other}$ when only one other component besides LDC 352 and LDC 382 is to be factored into a temperature compensated output $LDSO_{TC}$ for a particular cycle, or multiple distinct instances of $TE_{other}$ when multiple distinct components besides LDC 352 and LDC 382 are to be factored into a temperature compensated output $LDSO_{TC}$ for a particular cycle. Each one of the calibration temperatures of equation (6), such as $T_{LDC\_x}$ of LEC 352 and $T_{LDC\_x}$ of LEC 352, may be the same temperature or may differ from component to component.

Therefore, by calculating temperature-compensated output value $LDSO_{TC}$ of light detecting subsystem 380 for a particular smoke detection cycle of system 305 that takes into account the effect of one, some, or each of the various temperature-affected components of system (e.g., by subtracting or otherwise removing such effects from a non-compensated output value $LDSO_{detected}$), processor 315 may be enabled to use a more accurate output value of light detecting subsystem 380 in combination with previously determined light-smoke correlation data for more accurately determining a current smoke condition of the particular cycle. This may enable ultimate precision and/or sensitivity of smoke condition detection by system 305 despite temperature variation during its use. For example, $LDSO_{TC}$ may be used rather than $LDSO_{detected}$ for a particular cycle in order to identify an associated smoke condition (e.g., by processor 315 in combination with previously determined light-smoke correlation data of data 316d). In some embodiments, a particular $LDSO_{TC}$ may be used in combination with both the previously determined light-smoke correlation data of data 316d and a current detected temperature of system 305 (e.g., a current detected temperature of LEC 352 or a calculated temperature of location N1 or location N2), such that not only may a current temperature of one or more components of system 305 be detected and used to calculate $LDSO_{TC}$ from $LDSO_{detected}$, but then a current temperature of any suitable portion of space 301 as may be calculated in any suitable manner may also be used in combination with $LDSO_{TC}$ and previously determined light-smoke correlation data of data 316d to identify a particular smoke condition or otherwise (e.g., to provide a heat detection value or ambient temperature value for any suitable purpose). Any suitable processing or equation(s) or look-up tables or otherwise may be utilized to determine a smoke condition in combination with $LDSO_{TC}$ and/or with a current detected temperature of system 305 (e.g., a current detected temperature of LEC 352 and/or a calculated temperature of location N1 or location N2) and/or with data from any other sensors of the system (e.g., a humidity sensor). Such an identified smoke condition may then be used (e.g., by processor 315) to determine whether or not to sound an alarm (e.g., alarm 334) or enter into a different state (e.g., a pre-alarm state), such as by comparing the identified smoke condition to a threshold.

Figure 4:
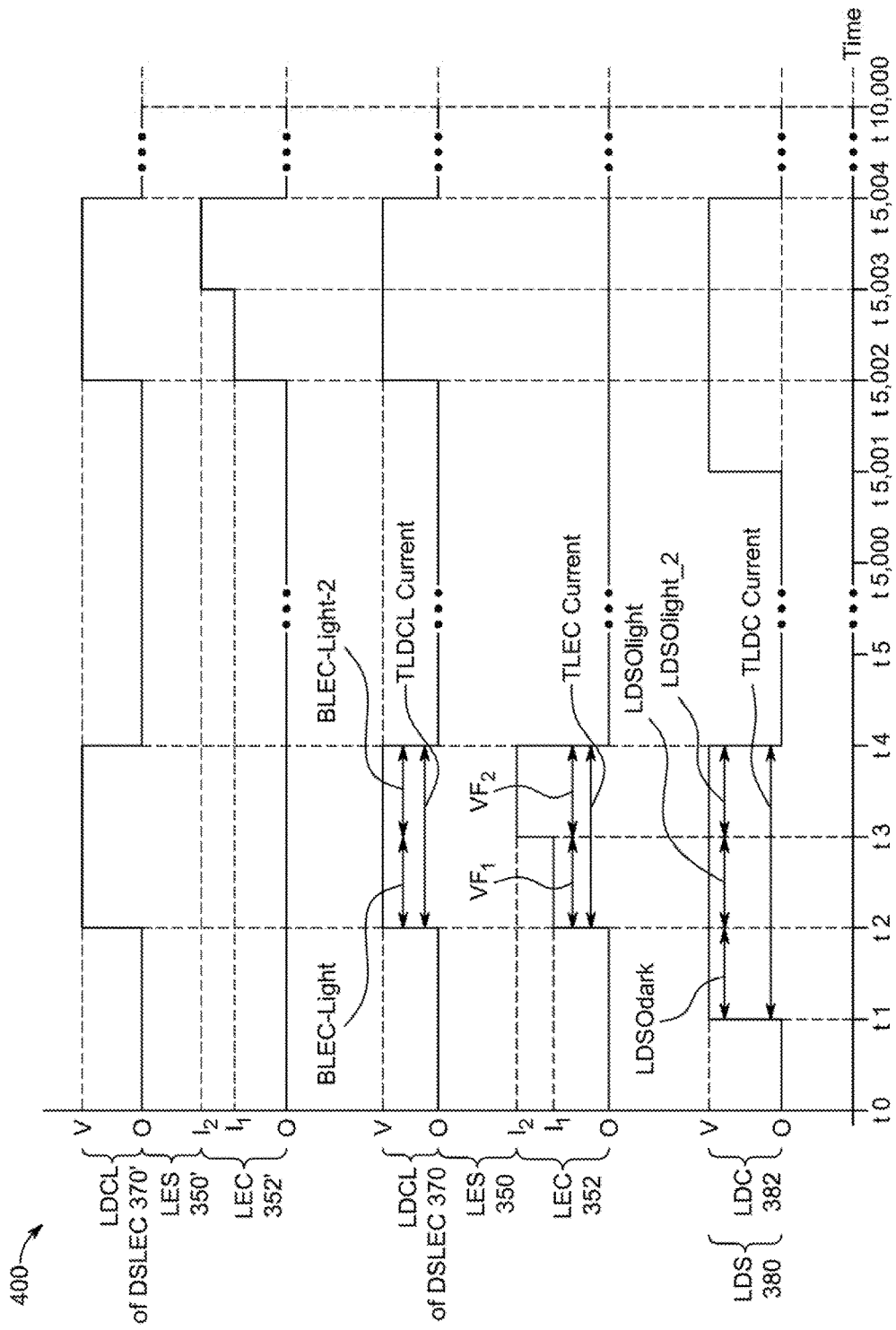
FIG. 4 shows an illustrative timing diagram, according to some embodiments.

FIG. 4 shows an illustrative timing diagram 400 for determining certain values (e.g., for determining certain components of equation (6), such as $LDSO_{light}$ and $LDSO_{dark}$ of $LDSO_{detected}$ and/or $T_{LDC\_current}$ of $TE_{LDC}$ and/or $T_{LEC\_current}$ of $TE_{LEC}$) in order to detect a smoke condition with system 305 (e.g., to solve for $LDSO_{TC}$ of equation (6)). For example, as shown, diagram 400 may depict a single particular cycle that may span between a time t0 and a time t10000, where the duration of time between t0 and t10000 may be any suitable duration, such as 10 seconds (e.g., such that a duration between any two successive time elements, such as t0 and t1, may be 1 millisecond). For a majority of the cycle, LDC 382 may not be powered on or otherwise enabled to detect light (e.g., to save power). For example, as shown, a 0 magnitude voltage may be applied to LDC 382 between time t0 and time t1 as well as between time t4 and time t10000. However, between time t1 and time t4, a voltage of magnitude V (e.g., the calibration power of LDC 382) may be applied to LDC 382 (e.g., for 3 milliseconds of a 10 second cycle (e.g., 0.03% of the cycle)). During a first portion of the time when LDC 382 is enabled, such as between time t1 and time t2, LDC 382 may be enabled while LEC 352 is not emitting light (e.g., when no current is injected into LEC 352 or LEC 352 is otherwise disabled), such that $LDSO_{dark}$ may be detected during that span. During a second portion of the time when LDC 382 is enabled, such as between time t2 and time t3, LDC 382 may be enabled while LEC 352 is emitting light (e.g., when a current of magnitude $I_1$ (e.g., the calibration power of LEC 352) is injected into LEC 352), such that $LDSO_{light}$ may be detected during that span. During one or more of the first portion and/or the second portion of the time when LDC 382 is enabled (e.g., between time t1 and time t2 and/or between time t2 and time t3), the current temperature $T_{LDC\_current}$ of LDC 382 for the current cycle may be determined (e.g., using one or more of equations (1) and (2) or using any suitable TSLD of subsystem 390). Additionally or alternatively, during the portion of the time when LEC 352 is enabled (e.g., between time t2 and time t3), the current temperature $T_{LEC\_current}$ of LEC 352 for the current cycle may be determined (e.g., using one or more of equations (1) and (2) or using any suitable TSLE of subsystem 360). Additionally or alternatively, during a portion of the time when LDC 382 is not enabled (e.g., between time t4 and time 5001), the current temperature $T_{LEC\_current}$ of LEC 352 for the current cycle may be determined (e.g., using one or more of equations (1) and (2) or using any suitable TSLE of subsystem 360), where LEC 352 may have a current injected therethrough to enable the determination of $T_{LEC\_current}$, yet such an injected current may be significantly less than $I_1$ or $I_2$ as the brightness of light L1 may not be needed to be detected by LDC 382 for hazard detection purposes, thereby saving some power.

However, if the technique of equation (3) is to be used to determine one or more of $T_{LDC\_current}$ of LDC 382 for the current cycle and $T_{LEC\_current}$ of LEC 352 for the current cycle, then not only may the time period between time t2 and time t3 be used to detect a first characteristic of one or both of LDC 382 and LEC 352 (e.g., to detect a first forward voltage $V_{f1}$ of LEC 352 when a first current of magnitude $I_1$ is injected into LEC 352), but a time period between time t3 and time t4 may be used to detect a second characteristic of one or both of LDC 382 and LEC 352 (e.g., to detect a second forward voltage $V_{f2}$ of LEC 352 when a second current of magnitude $I_2$ may be injected into LEC 352 and/or to detect $LDSO_{light-2}$ of LDC 382 during that span). As mentioned, during a certain duration of time during which the temperature of LEC 352 may not be able to vary by more than a certain minimal amount (e.g., the duration of time between time t2 and time t4 of diagram 400), not only may a first magnitude of current I (e.g., a first magnitude current $I_1$) be injected into LEC 352 at a first duration between time t2 and time t3 such that the magnitude of the forward voltage of LEC 352 (e.g., a first forward voltage $V_{f1}$) may be detected at that first duration, but also a second magnitude of current I (e.g., a second magnitude current $I_2$) may then be injected into LEC 352 at a second duration between time t3 and time t4 such that the magnitude of the forward voltage of LEC 352 (e.g., a second forward voltage $V_{f2}$) may be detected at that second duration, all while the current temperature $T_{LEC\_current}$ of LEC 352 may remain substantially or completely constant. Alternatively, such a process may be done during any suitable time period where such temperatures may change. Through such a process, processor 315 may be operative to determine current temperature $T_{LEC\_current}$ of LEC 352 (e.g., using equation (3)) with or without using any particular predetermined correlator data of LEC 352 or any TSLEs of subsystem 360. Alternatively or additionally, during such a variation of injected current into LEC 352, not only may a first magnitude of current be detected by LDC 382 at a first duration between time t2 and time t3 such that the magnitude of the bias of LDC 382 may be detected at that first duration (e.g., $LDSO_{light}$), but also a second magnitude of current may be detected by LDC 382 at a second duration between time t3 and time t4 such that the magnitude of the bias of LDC 382 may be detected at that second duration (e.g., $LDSO_{light\_2}$), all while the current temperature $T_{LDC\_current}$ of LDC 382 may remain substantially or completely constant. Through such a process, processor 315 may be operative to determine current temperature $T_{LDC\_current}$ of LDC 382 (e.g., using equation (3)) without using any particular predetermined correlator data of LDC 382 or any TSLDs of subsystem 390. As a particular example, the following two equations (3a) and (3b) may be used to solve for $T_{LDC\_current}$ of LDC 382:

$$I_{LDC\_light} = K_L * (B_{LEC\_light} * F_{chamber}) + K_{LDC} * (T_{LDC\_current} - T_{LDC\_x}) + I_{LDC\_dark}; \quad (3a)$$

and $$I_{LDC\_light\_2} = K_L * (B_{LEC\_light\_2} * F_{chamber}) + K_{LDC} * (T_{LDC\_current} - T_{LDC\_x}) + I_{LDC\_dark}, \quad (3b)$$

where $I_{LDC\_dark}$ may be the amount of current detected to be flowing through LDC 382 between time t1 and time t2 when no light is being emitted into space 303, $I_{LDC\_light}$ may be the amount of current detected to be flowing through LDC 382 between time t2 and time t3 when current $I_1$ is being injected into LEC 352, $I_{LDC\_light\_2}$ may be the amount of current detected to be flowing through LDC 382 between time t3 and time t4 when current $I_2$ is being injected into LEC 352, $K_L$ may be any suitable light sensitivity coefficient data associated with LDC 382 (e.g., light sensitivity coefficient data as Amperes per brightness unit (e.g., lux)), $B_{LEC\_light}$ may be the brightness of light L1 emitted from LEC 352 between time t2 and time t3 when current $I_1$ is being injected into LEC 352 (e.g., as may be determined by circuitry 356 or otherwise), $B_{LEC\_light\_2}$ may be the brightness of light L1 emitted from LEC 352 between time t3 and time t4 when current $I_2$ is being injected into LEC 352 (e.g., as may be determined by circuitry 356 or otherwise), $F_{chamber}$ may be indicative of the effect of space 303 on the brightness of light L1 to form the brightness of light L2, where $F_{chamber}$ may be assumed to be constant between time t2 and time t4 and/or may be removed from the calculation of $T_{LDC\_current}$ through the use of both of equations (3a) and (3b), $K_{LDC}$ may be any suitable brightness temperature coefficient data associated with LDC 382 (e.g., temperature gain coefficient or brightness temperature coefficient TCLDC γ of LDC 382), and $T_{LDC\_x}$ may be the calibration temperature of LDC 382, where such values for $K_L$, $K_{LDC}$, and $T_{LDC\_x}$ may be predetermined (e.g., during calibration or testing of system 305) and may be made available to processor 315 (e.g., as a portion of processor data 316d). After time t4, such as between time t4 and time t10000, no current may be injected into LED 352 such that no light L1 may be emitted therefrom (e.g., to save power).

An effect of temperature variation on LEC 352 (e.g., $TE_{LEC}$) may be ignored when functionality may be provided to maintain the brightness of light L1 emitted from LEC 352 at a particular magnitude despite temperature variation, which may enable $TE_{LEC}$ to be removed as a component from equation (6) when solving for $LDSO_{TC}$, such that $T_{LEC\_current}$ of LEC 352 may not need to be determined at each cycle. For example, rather than injecting a constant current I (e.g., a calibration power characteristic) when LEC 352 is enabled for emitting light L1 (e.g., current $I_1$ between times t2 and t3), whereby brightness of light L1 may vary as the temperature of LEC 352 varies, any suitable functionality may be provided to system 305 for attempting to maintain a current brightness of light L1 despite any temperature variations of LEC 352 (e.g., at a brightness equal to that of light L1 when the calibration power characteristic is applied to LEC 352 at a calibration temperature $T_{LEC\_x}$). In some embodiments, processor 315 (e.g., in conjunction with any suitable data 316d and LECC 354) may be operative to determine the current temperature $T_{LEC\_current}$ of LEC 352 and identify the proper amount of current to inject into LEC 352 to maintain the brightness of light L1 at a particular magnitude (e.g., a calibration brightness magnitude used during calibration of system 305). For example, data 316d may include any suitable correlator data for enabling processor 315 to identify an appropriate current to inject into LEC 352 for enabling LEC 352 to emit light L1 with a particular magnitude of brightness based on a particular detected current temperature $T_{LEC\ current}$ of LEC 352.

In addition to or as an alternative to processor 315 using correlator data between a detected temperature of LEC 352 and to-be-injected current for enabling emission of light L1 with a particular brightness, any suitable component(s) may be provided to maintain a particular brightness of light L1 emitted by enabled LEC 352 despite any temperature variations of LEC 352. For example, as shown in FIG. 3, hazard detection system 305 may include an LEC light detecting subsystem (DSLEC) 370 (e.g., as a portion of light emitting subsystem 350) that may include at least one dedicated LEC local light detecting component (LDCL) (e.g., at least one light detecting component including any suitable light detecting diode PD (e.g., a photodiode) that may be similar to LDC 382 of FIG. 3B). An LDCL of DSLEC 370 may be optically coupled to LEC 352 for detecting the brightness of light L1 emitted from LEC 352 without any interference due to variable conditions, such as the existence of smoke S within space 303 beyond subsystem 350, and such detected brightness may be used by any suitable circuitry (e.g., circuitry 356) to maintain a particular magnitude of the brightness of light L1 emitted from LEC 352 (e.g., despite any temperature variation at LEC 352), such as by adjusting the magnitude of the current injected into LEC 352 based on the brightness detected by DSLEC 370. As shown, DSLEC 370 may include at least one of LDCL 372 (e.g., a photodiode or any other suitable light sensing component that may be optically coupled to LEC 352 and that may be provided on the same die 353 as LEC 352 (e.g., at least partially within space 303)), LDCL 374 (e.g., a photodiode or any other suitable light sensing component that may be optically coupled to LEC 352 and provided on the same chip carrier or package 355 as die 353 of LEC 352 (e.g., at least partially within space 303) but not on die 353), LDCL 376 (e.g., a photodiode or any other suitable light sensing component that may be optically coupled to LEC 352 and that may be provided at least partially within chamber space 303 but not on package 355 of LEC 352), and/or LDCL 378 (e.g., a photodiode or any other suitable light sensing component that may be optically coupled to LEC 352 but provided outside of chamber space 303 (e.g., on board 306)). Any node(s) of one, some, or all LDCLs of DSLEC 370 may be electrically coupled to any suitable LDCL circuitry (LD-CLC) 379, which may be operative to enable the detection of the magnitude of the brightness of light sensed by such one or more LDCL(s) by processor 315. In some embodiments, LDCLC 379 may be similar to LDCC 384 of FIG. 3B.

Figure 3C:
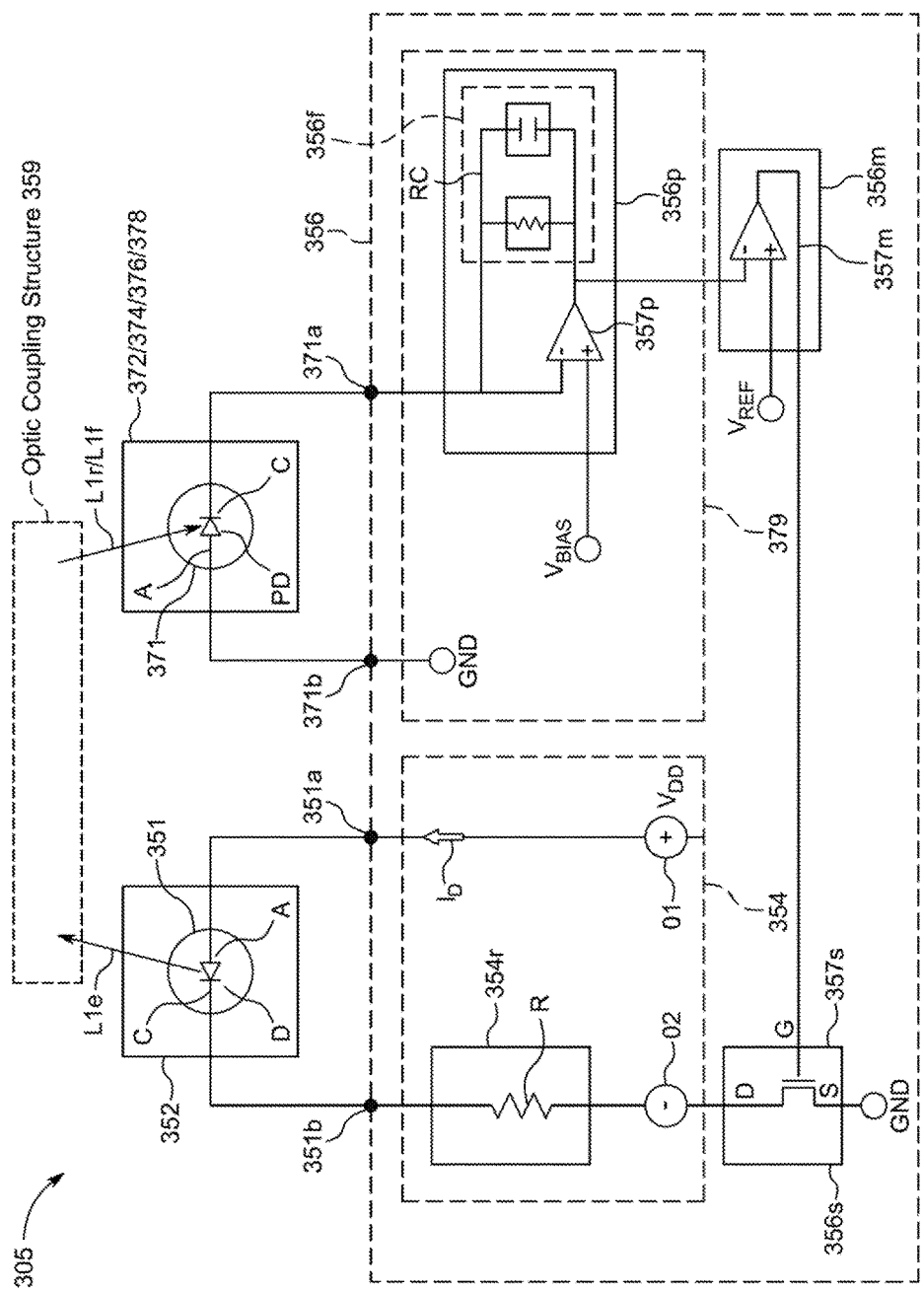
Figure 3D:
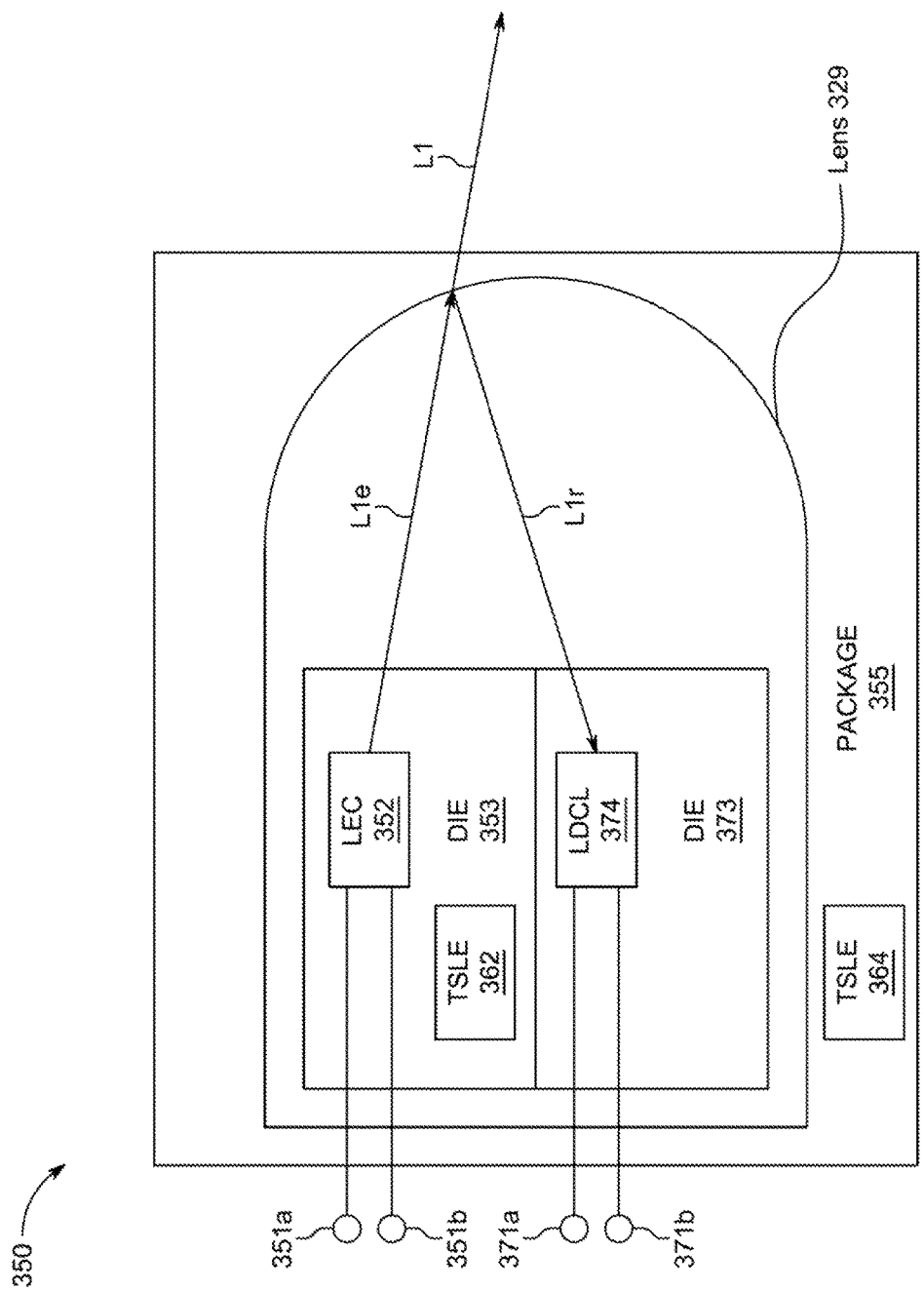

Any suitable LDCL of DSLEC 370 may be optically coupled to LEC 352 in any suitable manner for ensuring that the brightness of light actually emitted by LEC 352 may be detected by that LDCL without any interference due to variable conditions, such as existence of smoke S within space 303. For example, as shown in FIG. 3D, LDCL 374 may be provided on a die 373, and die 373 of LDCL 374 and die 353 of LEC 352 may be provided within the same package 355 (e.g., such as a T1 package, T1 ¾ package, and/or surface mount package). Pins 351a and 351b of light emitting element 351 of LEC 352 as well as pins 371a and 371b of a light detecting element (e.g., a photodiode) of LDCL 374 may be made available for use by any suitable components external to package 355 (e.g., circuitry 356). Dies 373 and 353 may be positioned against on another within package 355 or may be spaced any suitable distance within package 355. As shown, a lens 329 or any other suitable enclosure may be provided for shielding LEC 352 from debris, which may be operative to prevent any smoke (e.g., smoke particles S) from entering into lens 329 for damaging LEC 352. In some embodiments, as shown, at least a portion of die 373 and/or at least a portion of LDCL 374 may be provided within lens 329 (e.g., within an internal space defined by lens 329) along with at least a portion of LEC 352, such that LDCL 374 may also be protected from any debris external to lens 329. At least a portion of light L1e emitted from LEC 352 may be reflected by and retained within lens 329 and sensed by LDCL 374 as reflected light L1r, while another portion of light L1e emitted from LEC 352 may be emitted out from lens 329 and into space 303 as light L1 for sensing by LDC 382. Therefore, in such embodiments, a portion of light emitted from LEC 352 may always be detected by LDCL 374 in the same manner without any interference due to variable conditions external to lens 329 (e.g., existence of smoke), such that the brightness of such detected light L1r may be substantially identical to or directly proportional to the brightness of light L1e and/or of light L1. For example, such a configuration may ensure that the ratio of the brightness of light L1r to the brightness of light L1e is constant despite any variation in the brightness of light L1e and/or that the ratio of the brightness of light L1r to the brightness of light L1 is constant despite any variation in the brightness of light L1e. In some embodiments, a reflective material may be provided along an interior surface of a portion of lens 329 for reflecting light L1r towards the LDCL while the interior surface of other portions of lens 329 may not reflect light but may transmit light through lens 329. Alternatively, die 373 and LDCL 374 may be positioned directly behind LEC 352 and a dedicated path through the back of LEC 352 may be operative to enable some portion of light L1e to be detected by an LDCL positioned along that dedicated path (e.g., a path formed through black epoxy that may otherwise be provided along the backside of LEC 352 (e.g., along the back of LED D) to prevent light from escaping from the backside). By collocating LEC 352 and LDCL 374 on the same package 355, a current temperature of LEC 352 that may be detected using any suitable technique or TSLE of TSLEC 360 (e.g., TSLE 362 of die 353 or TSLE 364 of package 355) may be used as (e.g., assumed to be substantially identical to) a current temperature of LDCL 374, and/or a current temperature of LDCL 374 may be used as a current temperature of LEC 352.

As shown in FIGS. 3 and 3F, single die 353 may include both LEC 352 and LDCL 372. By collocating LEC 352 and LDCL 372 on the same die 353, a current temperature of LEC 352 that may be detected using any suitable technique or ISLE of TSLEC 360 (e.g., TSLE 362 of die 353) may be used as (e.g., assumed to be substantially identical to) a current temperature of LDCL 372, and/or a current temperature of LDCL 372 may be used as a current temperature of LEC 352. In some embodiments, as shown, an optic component 328 may be provided within and distinct from lens 329 or as a unique portion of lens 329, where optic component 328 may be operative to reflect a portion of light L1e as light L1r to LDCL 372. For example, such a configuration may ensure that the ratio of the brightness of light L1r to the brightness of light L1e is constant despite any variation in the brightness of light L1e and/or that the ratio of the brightness of light L1r to the brightness of light L1 is constant despite any variation in the brightness of light L1e. Optic component 328 may be a reflector or any other suitable component of any suitable shape. Moreover, as shown, optic component 328 may be operative to reflect at least a portion L3r of light L3 to LDCL 372, where light L3 may be any suitable light from any suitable remote light source that may pass through lens 329.

Any suitable light pipe may be provided for optically coupling a portion of light emitted from LEC 352 to one or more LDCLs of DSLEC 370 of system 305. For example, as shown in FIG. 3E, a light guide 325 may be provided for routing light portion L1f of light L1e emitted from LEC 352 to any one of LDCLs 372, 374, 376, and 378 of DSLE 370 such that light portion L1f may be detected by the light detecting element (e.g., a photodiode) of that LDCL. As shown, light guide 325 may include a path for light L1f between a first end 325a of light guide 325 and a second end 325b of light guide 325. For example, first end 325a of light guide 325 may be optically coupled to a portion of lens 329 for receiving light L1f, such that conditions external to lens 329 and light guide 325 may not affect the brightness of light L1f. Second end 325b of light guide 325 may be optically coupled to any suitable portion of an LDCL or to a portion of a lens 327 or any other suitable enclosure may be provided for shielding the LDCL from debris, which may be operative to prevent any smoke (e.g., smoke particles S) from entering into lens 327 for damaging the LDCL. Light guide 325 may be made of any suitable materials and may have any suitable dimensions and/or any suitable geometry for optically coupling a portion of light emitted from LEC 352 with an LDCL of DSLEC 370, such that light guide 325 may enable LEC 352 and the LDCL to be separated by any suitable distance and with diodes having any suitable relative orientations. For example, light guide 325 may be configured to extend between LEC 352 within space 303 and LDCL 378 outside of space 303 and/or between LEC 352 in first package 355 and an LDCL in a different second package. Light guide 325 may be a light guide pipe, a fiber optic fiber, an acrylic tube, or any other suitable light guide that may be operative to pass light L1f from end 325a to end 325b without any external variables affecting such passage of light (e.g., any smoke, temperature, light, or the like external to light guide 325). Any suitable material or element(s) may be provided along one or more surfaces of light guide 325 and/or of lens 327 to prevent external variables from affecting light passing along light guide 325. For example, a lens shield 327s may be provided alone one or more surfaces of lens 327 for shielding variables external to lens 327 from affecting the passage of light between guide 325 and an LDCL, and/or a light guide shield 325s may be provided alone one or more surfaces of light guide 325 for shielding variables external to light guide 325 from affecting the passage of light along guide 325, where either or both of such shields may be made from any suitable materials, such as black acrylonitrile butadiene styrene (ABS) for shielding external light. Therefore, in such embodiments, a portion of light emitted from LEC 352 may always be detected by an LDCL via light guide 325 in the same manner without any interference due to variable conditions external to guide 325 (e.g., existence of smoke), such that the brightness of such detected light L1f may be substantially identical to or directly proportional to the brightness of light L1e and/or of light L1. For example, such a configuration may ensure that the ratio of the brightness of light L1f to the brightness of light L1e is constant despite any variation in the brightness of light L1e and/or that the ratio of the brightness of light L1f to the brightness of light L1 is constant despite any variation in the brightness of light L1e.

Any suitable correlator data between the brightness of light L1e or L1 and the brightness of light L1f or the brightness of light L1r detected by an LDCL (e.g., as $B_{LDC\_current}$) may be determined (e.g., during calibration of system 305) and may be utilized (e.g., as a portion of data 316d by processor 315) to determine or otherwise calculate or estimate the current brightness $B_{LEC\_current}$ of light L1. In some embodiments, processor 315 (e.g., in conjunction with any suitable data 316d and circuitry 356) may be operative to use the current brightness $B_{LEC\_current}$ of light L1 (e.g., as determined using any suitable LDCL of DSLEC 370) to identify the proper amount of current to inject into LEC 352 to maintain or return the brightness of light L1 to a particular magnitude (e.g., a calibration brightness magnitude used during calibration of system 305). For example, data 316d may include any suitable correlator data for enabling processor 315 to identify an appropriate current to inject into LEC 352 for enabling LEC 352 to emit light L1 with a particular magnitude of brightness based on a particular determined current brightness $B_{LEC\_current}$ of LEC 352 (e.g., as a digital feedback loop or otherwise). Additionally or alternatively, the particular determined current brightness $B_{LEC\_current}$ of LEC 352 may be processed in conjunction with $LDSO_{detected}$ to determine a current smoke condition (e.g., with or without factoring in a current temperature effect on LEC 352 and/or LDC 382, etc.). For example, the particular determined current brightness $B_{LEC\_current}$ of LEC 352 may be used to index to particular data in a predetermined table for identifying a smoke condition in conjunction with $LDSO_{detected}$. Any hardware, software, or combination of hardware and software may be utilized in combination with the particular determined current brightness $B_{LEC\_current}$ of LEC 352 to determine the current smoke condition.

In addition to or as an alternative to processor 315 using correlator data between a determined current brightness of light L1 of LEC 352 and a magnitude of to-be-injected current for enabling emission of light L1 with a particular brightness, any suitable component(s) may be provided to enable light L1 emitted by enabled LEC 352 to be held at a particular brightness despite any temperature variations of LEC 352. For example, as shown in FIGS. 3 and 3C, hazard detection system 305 may include a subsystem or circuitry 356, which may include at least a portion of LECC 354 and/or at least a portion of LDCLC 379, where circuitry 356 may be operative to use the current brightness $B_{LEC\_current}$ of light L1 (e.g., as determined using any suitable LDCL of DSLEC 370) for causing LEC 352 to emit light L1 with a particular brightness (e.g., a calibration brightness magnitude). Circuitry 356 may be a servo mechanism that may be operative to uses error-sensing negative feedback to correct the performance of LEC 352 (e.g., to maintain the brightness of light L1 at a particular brightness when LEC 352 is enabled despite variance in the temperature of LEC 352). For example, as shown in FIG. 3C, circuitry 356 (e.g., analog feedback circuitry) may be electrically coupled to one or both of pins 351a and 351b of light emitting element 351 (e.g., LED D) of LEC 352 as well as electrically coupled to one or both of pins 371a and 371b of light detecting element 371 (e.g., photodiode PD) of any one of LDCLs 372, 374, 376, and 378 of DSLEC 370 of subsystem 350, where that LDCL and LEC 352 may be optically coupled via any suitable optical coupling structure 359 in any suitable manner (e.g., an opto-isolator, such as an LED-photodiode opto-isolator, and/or any optical coupling structure as described with respect to one or more of FIGS. 3, 3D, and 3E (e.g., lens 329 and/or light guide 325 and/or lens 327 and/or optic component 328)), such that circuitry 356 may be operative to servo the magnitude of the current In injected into light emitting element 351 of LEC 352 to maintain a constant value of the brightness of the light (e.g., light L1r or light L1f) sensed by light detecting element 371 of the LDCL and, thus, to maintain a constant brightness of light L1 (e.g., despite any variance in the temperature of LEC 352).

As just one particular embodiment of circuitry 356, as shown in FIG. 3C, circuitry 356 may include LDCLC 379, LECC 354, and any other suitable components, such as a variable resistance component 356s and a first amplifier component 356m. Variable resistance component 356s may be electrically coupled to node O2 of LECC 354 or otherwise to the cathode C of light emitting element 351 of LEC 352 and to a cathode C of light detecting element 371 of the LDCL via one or more other components of circuitry 356, such as a first amplifier component 356m and a second amplifier component 356p, which may provide a negative feedback amplifier. As shown, variable resistance component 356s may include any suitable variable resistance circuitry, such as a field effect transistor (FET) 357s, where a drain of FET 357s may be coupled to node O2 of LECC 354 or otherwise to the cathode C of light emitting element 351 of LEC 352 (e.g., via element 354r), a source of FET 357s may be coupled to ground or any other suitable element, and a gate if FET 357s may be coupled to an output of first amplifier component 356m (e.g., to an output of an operational amplifier 357m of first amplifier component 356m). As also shown, a non-inverting input of operational amplifier 357m of first amplifier component 356m may be coupled to any suitable power source (e.g., to a voltage source of $V_{REF}$), while an inverting input of operational amplifier 357m of first amplifier component 356m may be coupled to any suitable portion of second amplifier component 356p (e.g., to an output of an operational amplifier 357p of second amplifier component 356p), while a non-inverting input of operational amplifier 357p of second amplifier component 356p may be coupled to any suitable power source (e.g., to a voltage source of $V_{BIAS}$), and while an inverting input of operational amplifier 357p of second amplifier component 356p may be coupled to the output of operational amplifier 357p of second amplifier component 356p via a filter component 356f, which may include a resistor-capacitor circuit RC, and to cathode C of light detecting element 371 of the LDCL. The output of operational amplifier 357m of first amplifier component 356m may be operative to be applied to variable resistance component 356s (e.g., to the gate of FET 357s) for adjusting the amount of current $I_D$ that may be drawn through light emitting element 351 of LEC 352, which may adjust the brightness of light L1 emitted by LEC 352, while the output of operational amplifier 357m of first amplifier component 356m may be varied based on the brightness of light detected by light detecting component 351 of the LDCL. The value of $V_{BIAS}$ may be selected to set the magnitude of the brightness of light L1 desired to be emitted by LEC 352, while the value of $V_{REF}$ may be selected to set the magnitude of current desired to be drawn through LEC 352. Therefore, circuitry 356 may be operative to provide an analog feedback circuit (e.g., with at least one suitable feedback loop (e.g., as a closed-loop servo'd subsystem)) that may maintain consistent brightness of light L1 emitted by LEC 352 over varying temperatures of LEC 352 through using an LDCL that may be optically coupled to LEC 352.

When an LDCL of DSLEC 370 may be optically coupled to LEC 352 and used to maintain the brightness of light L1 emitted by LEC 352 at a particular magnitude (e.g., in coordination with circuitry 356 or otherwise), then an effect of temperature variation on LEC 352 (e.g., $TE_{LEC}$) may be ignored or at least reduced to that of the effect of temperature variation on the optically coupled LDCL (e.g., $TE_{LDC}$). For example, when the brightness of light L1 is maintained at a particular magnitude despite temperature variation of LEC 352 through using an optically coupled LDCL, $TE_{LEC}$ may be removed as a component from equation (6) when solving for $LDSO_{TC}$, such that $T_{LEC\_current}$ of LEC 352 may not need to be determined at each cycle. Instead, $LDSO_{TC}$ may be solved for using the following equation (6a):

$$LDSO_{TC} = LDSO_{detected} - TE_{LDC} - TE_{LDCL}, \quad (6a)$$

where $LDSO_{TC}$ may be a temperature-compensated output value of light detecting subsystem 380 for a particular smoke detection cycle of system 30, where $LDSO_{detected}$ may be a detected output of light detecting subsystem 380 during the particular cycle that has not been compensated for any temperature variance from the particular calibration temperature of system 305, where $TE_{LDC}$ may be an effect of a current temperature of LDC 382 during the particular cycle on the determination of the current smoke condition of the particular cycle, and where $TE_{LDCL}$ may be an effect of a current temperature of the LDCL during the particular cycle on the determination of the current smoke condition of the particular cycle, where that LDCL may be optically coupled to LEC 352 and used to maintain the brightness of emitted light L1 of LEC 352 during the particular cycle. Such a $TE_{LDCL}$ may be calculated using the following equation:

$$TE_{LDCL} = K_{LDCL} * (T_{LDCL\_current} - T_{LDCL\_x}), \quad (11)$$

where $K_{LDCL}$ may be any suitable temperature gain coefficient or brightness temperature coefficient data associated with that LDCL, where $T_{LDCL\_current}$ may be a current temperature of that LDCL during the particular cycle, and where $T_{LDCL\_x}$ may be the calibration temperature of that LDCL. Such values for $K_{LDCL}$ and $T_{LDCL\_x}$ may be predetermined (e.g., during calibration or testing of system 305) and may be made available to processor 315 (e.g., as a portion of processor data 316d associated with the temperature coefficient of that LDCL), while the current temperature $T_{LDCL\_current}$ of that LDCL during the particular cycle may be determined in any suitable manner (e.g., using one or more of equations (1)-(3) or any suitable temperature sensors proximate or thermally coupled to that LDCL). For example, the current temperature $T_{LDCL\_current}$ of the LDCL of FIG. 3C may be determined using a detected current temperature $T_{LEC\_current}$ of LEC 352 (e.g., if LEC 352 and the LDCL are collocated such that their temperatures may be assumed to be substantially the same) and/or using any suitable TSLE of subsystem 350 that may be proximate the LDCL and/or using one or more temperature detection techniques (e.g., equations (1)-(3)) with respect to the diode of the LDCL itself. As mentioned, the value of $K_{LDCL}$ or the brightness temperature coefficient of any suitable light sensing element may be significantly less than the value of $K_{LEC}$ or the brightness temperature coefficient of any suitable light emitting element (e.g., 0.1%/° Celsius as compared to −0.8%/° Celsius), such that using an optically coupled LDCL to remove the temperature variation effect of LEC 352 while adding a temperature variation effect of that LDCL may result in a much more accurate reading of $LDSO_{TC}$ even if $TE_{LDCL}$ is not taken into account as compared to a determination of $LDSO_{TC}$ if no optically coupled LDCL is used and if $TE_{LDCL}$ is not taken into account. As shown in timing diagram 400 of FIG. 4, if an LDCL of DSLEC 370 is optically coupled to LEC 352 and used for maintaining a constant brightness of light L1, then that LDCL may be enabled at least between times t2 and t3 (if not also between times t3 and t4) when LEC 352 may be enabled (e.g., by applying a voltage V across the light detecting element 371 of the LDCL), during which $T_{LDCL\_current}$ may be determined using any suitable technique (e.g., similar to the determination of $T_{LDC\_current}$).

Chamber space 303 of internal chamber body 302 may include other subsystems in addition to at least a portion of light emitting subsystem 350 and at least a portion of light detecting subsystem 380. For example, as shown in FIG. 3, at least a portion of an additional light emitting subsystem 350' of hazard detection system 305 may be positioned within chamber space 303, where additional light emitting subsystem 350' may include one or more similarly labelled components of light emitting subsystem 350, such as LEC 352' that may be operative to emit light L1' for reflecting off smoke S' as light L2' towards LDC 382, die 353', package 355', LECC 354', circuitry 356', TSLEC 360' that may include one or more of TSLE 362', TSLE 364', TSLE 366', and TSLE 368', TSLECC 369', DSLEC 370' that may include one or more of LDCL 372', LDCL 374', LDCL 376', and LDCL 378', and LDCLC 379'. LES 350' may be operative to function similarly to LES 350 with respect to LDS 380, such that smoke S' may reflect at least a portion of light L1' emitted from LES 350' towards LDC 382 as light L2' such that smoke S' may be detected by system 305. As shown in FIG. 3, for example, LES 350' may be positioned below or adjacent or proximate to opening 304', while LES 350 may be positioned closer to opening 304 than to opening 304', such that LES 350 and LDS 380 may be operative to detect smoke closer to opening 304 (e.g., smoke S) while LES 350' and LDS 380 may be operative to detect smoke closer to opening 304' (e.g., smoke S'). Alternatively or additionally, LES 350 and LES 350' may each be operative to work with LDS 380 for detecting any smoke within space 303. In some embodiments, although not shown, a second LDS similar to LDS 380 may be provided by system 305 for detecting light emitted from LES 350' as LDS 380 may detect light emitted from LES 350. As shown in FIG. 3, for example, LES 350 may be positioned within space 303 at least a distance D from LDS 380 (e.g., LEC 352 may be positioned at least a distance D from LDC 382), while LES 350' may be positioned within space 303 at least a distance D' from LDS 380 (e.g., LEC 352' may be positioned at least a distance D' from LDC 382).

In some embodiments, the wavelength(s) of light that may be emitted by LEC 352' of LES 350' may be the same as the wavelength(s) of light that may be emitted by LEC 352 of LES 350. Alternatively, in some embodiments, the wavelength(s) of light that may be emitted by LEC 352' of LES 350' may be different than the wavelength(s) of light that may be emitted by LEC 352 of LES 350. For example, light L1 emitted by LEC 352 of LES 350 may be infrared light (e.g., light emitting element 351 of LEC 352 may be an infrared (IR) LED that may emit light energy in the infrared electromagnetic spectrum) while light L1' emitted by LEC 352' of LES 350' may be blue light (e.g., a light emitting element of LEC 352' may be a blue LED that may emit light energy in the blue electromagnetic spectrum), where the different types of light may each be detected by LDC 382 of LDS 380 or by different LDCs of LDS 380 or by the same or different LDCs of different LDSs or LESs of system 305. Different types of light may be scattered by different types of particles in different ways or by the same particle in different ways within space 303, such that different sized particles (e.g., smoke S and smoke S') can be detected by system 305, thereby enabling various algorithms to use the data to make more informed decisions when operating the hazard detection system. For example, white/gray smoke may have different mean particle sizes than black smoke. In addition, moisture particles may have different mean particles size than smoke particles and dust. In addition, smoke from fast burning fires may have different mean particle sizes than smoldering fires. Mean particle sizes may also differ based on the material that is burning. It is to be understood that any suitable type(s) of light, including visible radiation and/or invisible radiation of any suitable wavelength, may be emitted by LEC 352 of LES 350 and/or by LEC 352' of LES 350' and/or detected by any LDCL of DSLEC 370 of LES 350 and/or by any LDCL of DSLEC 370' of LES 350' and/or by LDC 382 of LDS 380. It is to be understood that any reference to brightness and/or a magnitude or amount or quantity thereof (e.g., with respect to light or radiation L1 emitted by LEC 352 and/or with respect to light or radiation L2 detected by LDC 382) may be a reference to irradiance, radiance, radiant flux, illuminance, luminance, luminous flux, and/or the like and/or a magnitude or amount or quantity thereof (e.g., with respect to light or radiation L1 emitted by LEC 352 and/or with respect to light or radiation L2 detected by LDC 382).

LES 350 and LES 350' may have different functional characteristics, different calibration power characteristic values, different calibration brightness values, different calibration temperature values, different associated correlator data, different temperature coefficient data, and/or the like, which may be associated with different portions of data 316d, and/or LDS 380 and circuitry and processing (e.g., on board 306) may be operative to function differently with respect to LES 350 than with respect to LES 350'. However, LES 350 and LES 350' may be configured to operate in similar manners. As shown in FIG. 4, for example, when both LES 350 and LES 350' may be used with LDS 380, LES 350 and LDS 380 may be operative to function during a first portion of the cycle of diagram 400 (e.g., between times t1 and t4), while LES 350' and LDS 380 may be operative to function during a second portion of the cycle of diagram 400 that may be different than the first portion of the cycle (e.g., between times t5001 and t5004). The operation of LDC 382 of LDS 380 between times t5001 and t5004 with respect to LES 350' may be similar to the operation of LDC 382 of LDS 380 between times t1 and t4 with respect to LES 350, the operation of LEC 352' of LES 350' between times t5001 and t5004 with respect to LDC 382 of LDS 380 may be similar to the operation of LEC 352 of LES 350 between times t1 and t4 with respect to LDC 382 of LDS 380, and/or the operation of an LDCL of DSLEC 370' of LES 350' between times t5001 and t5004 with respect to LEC 352' of LES 350' and LDC 382 of LDS 380 may be similar to the operation of an LDCL of DSLEC 370 of LES 350 between times t1 and t4 with respect to LEC 352 of LES 350 and LDC 382 of LDS 380.

Figure 3G:
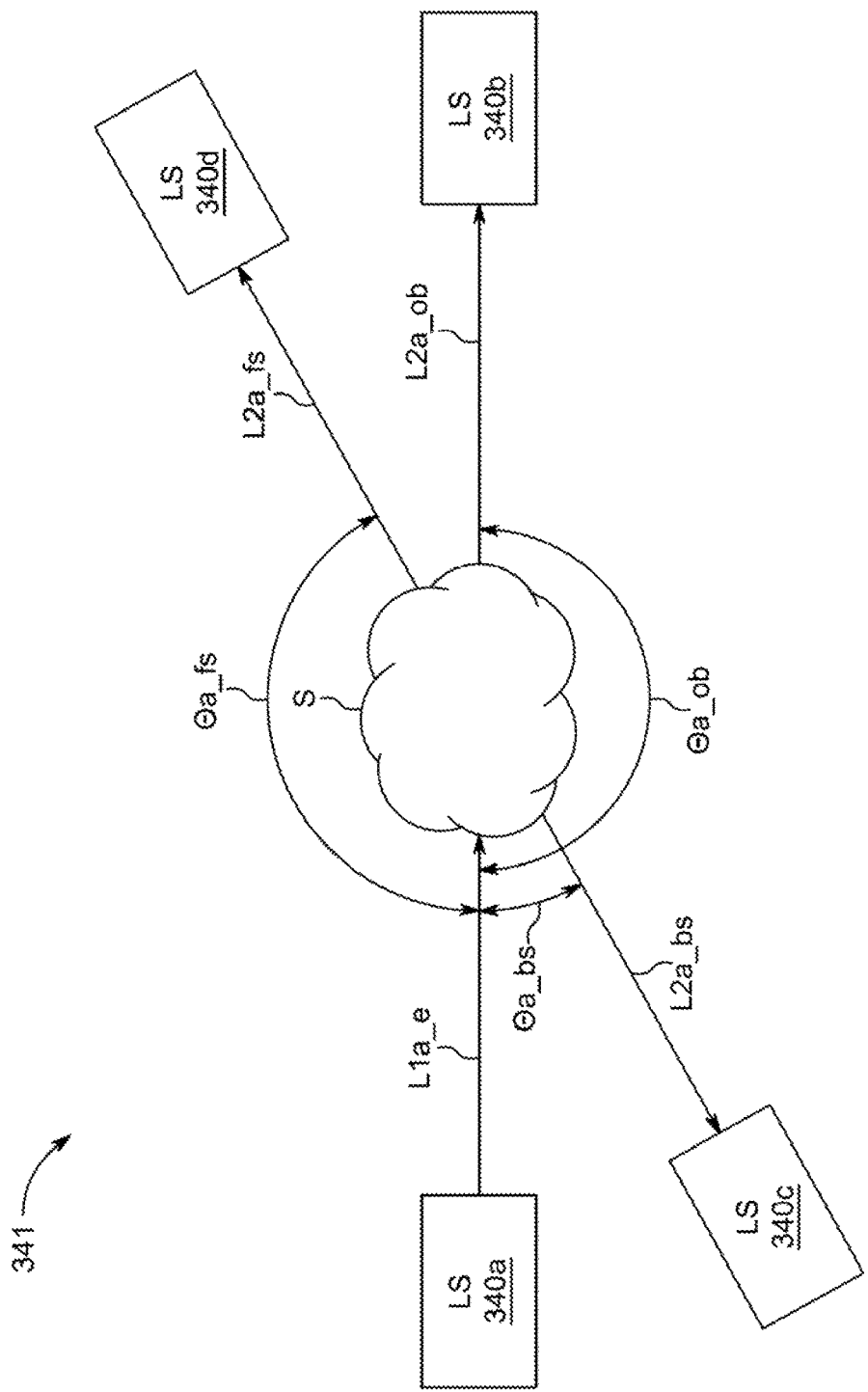
Figure 3H:
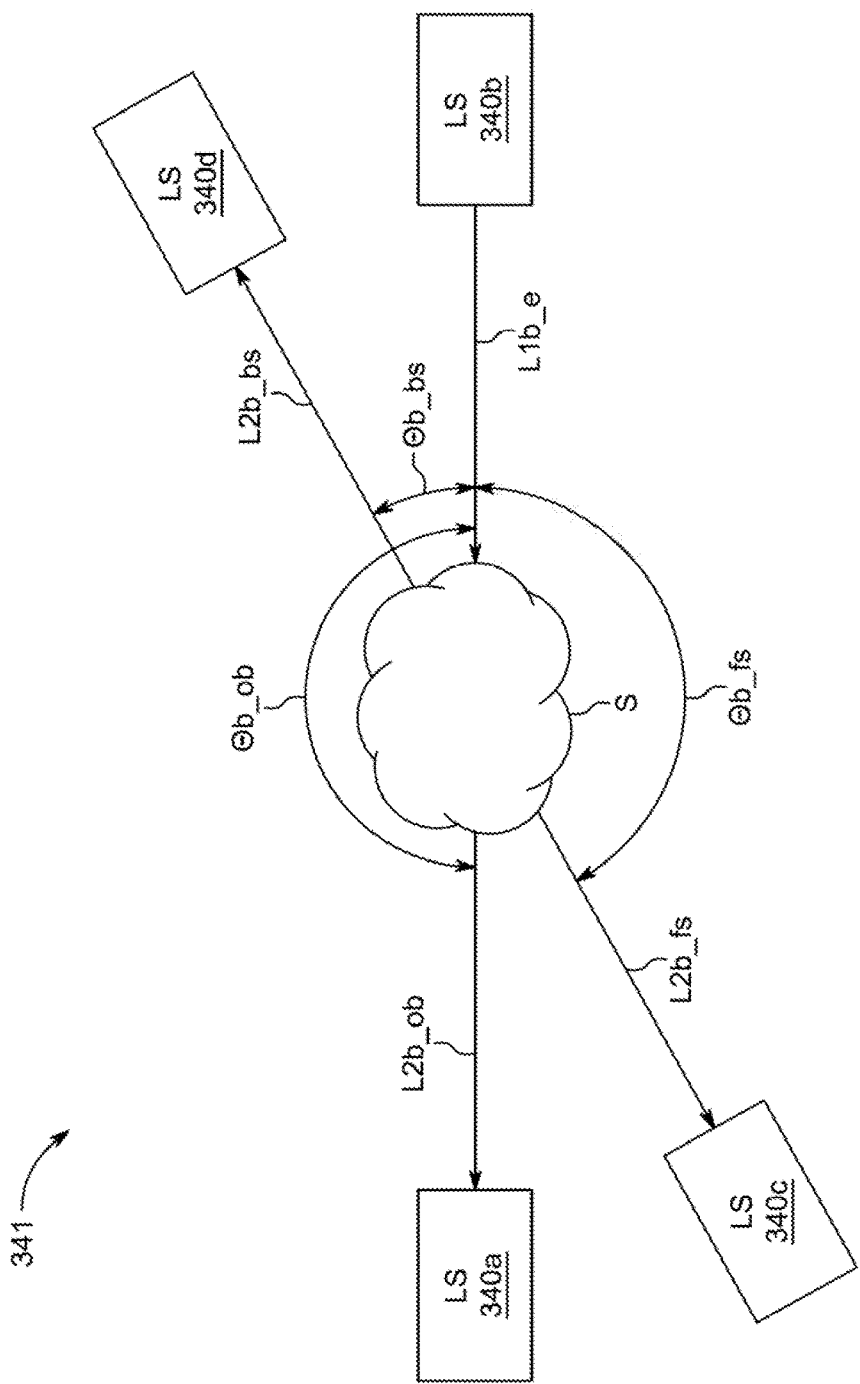

Any suitable number of light subsystems (LS) of any suitable type (e.g., light emitting subsystem(s) similar to LES 350 and/or light detecting subsystem(s) similar to LDS 380) may be positioned at least partially within space 303 in any suitable configuration for detecting hazard conditions. For example, as shown in FIGS. 3G and 3H, a configuration 341 of four light subsystems 340a-340d may be provided at least partially within space 303 and may be operated for effectively detecting hazard conditions. At a first moment of configuration 341, as shown in FIG. 3G, LS 340a may be operative to emit light L1a_e into space 303, where LS 340a may be any suitable subsystem operative to emit light into space 303, such as LES 350 emitting light L1 or LES 350' emitting light L1'. Moreover, at such a first moment of configuration 341 of FIG. 3G, LS 340b may be operative to detect light L2a_ob that may be at least a portion of emitted light L1a_e as deflected or diffracted or not obscured by smoke S (e.g., any suitable particle or particulate of fluid within chamber space 303 to be detected by hazard detection system 305). An axis of light L1a_e emitted from LS 340a may be offset from an axis of any light L2a_ob detected by LS 340b by an angle θa_ob of any suitable magnitude, such as by 180° where the two axes may be linear with one another so that detected light L2a_ob of emitted light L1a_e may be the portion of emitted light L1a_e not obscured by smoke S or passed through smoke S (e.g., detected light L2a_ob may be referred to herein as an obscuration light portion of emitted light L1a_e). Additionally or alternatively, at such a first moment of configuration 341 of FIG. 3G, LS 340c may be operative to detect light L2a_bs that may be at least a portion of emitted light L1a_e as deflected or diffracted or reflected or backscattered by smoke S. An axis of light L1a_e emitted from LS 340a may be offset from an axis of any light L2a_bs detected by LS 340c by an angle θa_bs of any suitable magnitude, such as between 1° and 89° or between 5° and 65° or about 40° so that detected light L2a_bs of emitted light L1a_e may be a portion of emitted light L1a_e backscattered by smoke S (e.g., detected light L2a_bs may be referred to herein as a backscattered light portion of emitted light L1a_e). Additionally or alternatively, at such a first moment of configuration 341 of FIG. 3G, LS 340d may be operative to detect light L2a_fs that may be at least a portion of emitted light L1a_e as deflected or diffracted or reflected or forward scattered by smoke S. An axis of light L1a_e emitted from LS 340a may be offset from an axis of any light L2a_fs detected by LS 340d by an angle θa_fs of any suitable magnitude, such as between 91° and 179° or between 95° and 155° or about 140° so that detected light L2a_fs of emitted light L1a_e may be a portion of emitted light L1a_e forward scattered by smoke S (e.g., detected light L2a_fs may be referred to herein as a forward scattered light portion of emitted light L1a_e). One, some, or all of LS 340b, LS 340c, and LS 340d may be any suitable subsystem operative to detect light within space 303, such as LDS 380 detecting light L2 or LES 350 detecting light L3 (see, e.g., FIG. 3F).

While only one of LS 340b, LS 340c, and LS 340d may be used to detect a portion of light L1a_e emitted from LS 340a, any two or all three of LS 340b, LS 340c, and LS 340d and/or any other suitable number of light subsystems may be used to detect different respective portions of light L1a_e emitted from LS 340a in order to provide additional data that may be used by system 305 (e.g., processor 315) to determine a current hazard condition within space 303. For example, smoke particles of different sizes may provide different ratios of forward scattered light to backscattered light when positioned at least partially along the axis of light L1a_e emitted by LS 340a (e.g., smaller particles may have a larger ratio of backward scatter to forward scatter than may larger particles). By comparing the magnitude (e.g., the brightness, radiance, etc.) of two or more of obscuration light portion L2a_ob, backscattered light portion L2a_bs, and forward scattered light portion L2a_fs with emitted light L1a_e and any suitable correlator data or calibration data (e.g., data 316d) may enable system 305 to determine more effectively certain characteristics about the current hazard condition within space 303 (e.g., the size of smoke S), thereby enabling various algorithms to use the data to make more informed decisions when operating the hazard detection system.

Moreover, as mentioned with respect to LES 350 and LES 350', different types of light may be scattered by different types of particles (e.g., smoke generated by burning wood versus smoke generated by burning metal) in different ways or by the same particle in different ways within space 303, such that different sized particles (e.g., smoke S and smoke S') can be detected by system 305, thereby further enabling various algorithms to use the data to make more informed decisions when operating the hazard detection system. Therefore, in some embodiments, at least two different light sources may be utilized by configuration 341. For example, at a second moment of configuration 341, as shown in FIG. 3H, that may occur before and/or after the first moment of FIG. 3G, LS 340b may be operative to emit light L1b_e into space 303, where LS 340b may be any suitable subsystem operative to emit light into space 303, such as LES 350 emitting light L1 or LES 350' emitting light L1'. Moreover, at such a second moment of configuration 341 of FIG. 3H, LS 340a may be operative to detect light L2b_ob that may be at least a portion of emitted light L1b_e as deflected or diffracted or not obscured by smoke S. An axis of light L1b_e emitted from LS 340b may be offset from an axis of any light L2b_ob detected by LS 340a by an angle θb_ob of any suitable magnitude, such as by 180° where the two axes may be linear with one another so that detected light L2b_ob of emitted light L1b_e may be the portion of emitted light L1b_e not obscured by smoke S or passed through smoke S (e.g., detected light L2b_ob may be referred to herein as an obscuration light portion of emitted light L1b_e). Additionally or alternatively, at such a second moment of configuration 341 of FIG. 3H, LS 340d may be operative to detect light L2b_bs that may be at least a portion of emitted light L1b_e as deflected or diffracted or reflected or backscattered by smoke S. An axis of light L1b_e emitted from LS 340b may be offset from an axis of any light L2b_bs detected by LS 340d by an angle θb_bs of any suitable magnitude, such as between 1° and 89° or between 5° and 65° or about 40° (e.g., angle θb_bs may be the same as angle θa_bs when angle θa_ob and angle θb_ob are 180°) so that detected light L2b_bs of emitted light L1b_e may be a portion of emitted light L1b_e backscattered by smoke S (e.g., detected light L2b_bs may be referred to herein as a backscattered light portion of emitted light L1b_e). Additionally or alternatively, at such a second moment of configuration 341 of FIG. 3H, LS 340c may be operative to detect light L2b_fs that may be at least a portion of emitted light L1b_e as deflected or diffracted or reflected or forward scattered by smoke S. An axis of light L1b_e emitted from LS 340b may be offset from an axis of any light L2b_fs detected by LS 340c by an angle θb_fs of any suitable magnitude, such as between 91° and 179° or between 95° and 155° or about 140° (e.g., angle θb_fs may be the same as angle θa_fs when angle θa_ob and angle θb_ob are 180°) so that detected light L2b_fs of emitted light L1b_e may be a portion of emitted light L1b_e forward scattered by smoke S (e.g., detected light L2b_fs may be referred to herein as a forward scattered light portion of emitted light L1b_e).

Therefore, where configuration 341 may enable LS 340a to emit light L1a_e at a first moment and detect light L2b_ob at a second moment, and may enable LS 340b to emit light L1b_e at the second moment and detect light L2a_ob at the first moment, each one of LS 340a and LS 340b may be any suitable subsystem operative to emit and detect light, such as LES 350 emitting light L1 with LEC 352 and detecting light L3 with an LDCL (see, e.g., FIG. 3F) or LES 350 may be operative to switch circuitry coupled to LEC 352 for alternately using a single optoelectronic component as a light emitting component and a light detecting component (e.g., by configuring LECC 354 to alternate between the circuitry of FIG. 3A for using light component 351 as an LED and the circuitry of FIG. 3B for using light component 351 as a photodiode), while each one of LS 340c and 340d may be any suitable subsystem operative to detect light within space 303, such as LDS 380 detecting light L2 or LES 350 detecting light L3. For example, as shown in FIG. 4, when LS 340a may be LES 350 and LS 340b may be LES 350' and LS 340c may be LDS 380, the first moment of configuration 341 of FIG. 3G may be at least partially between times t2 and t4 where LEC 352 of LS 340a may emit light L1a_e and an LDCL of DSLEC 370' of LS 340b may be enabled to detect light L2a_ob and LDC 382 of LS 340c may be enabled to detect light L2a_bs, and the second moment of configuration 341 of FIG. 3H may be at least partially between times t5002 and t5004 where LEC 35T of LS 340b may emit light L1b_e and an LDCL of DSLEC 370 of LS 340a may be enabled to detect light L2b_ob and LDC 382 of LS 340c may be enabled to detect light L2b_fs, all of which may occur within a single particular cycle that may be repeated. Although not shown, configuration 341 may be operative to enable each one of LS 340a-340d to emit light into space 303 at a different moment within a single repeatable cycle while the other ones of LS 340a-340d may detect different portions of such emitted light, where each one of LS 340a-340d may be a light subsystem operative to switch between emitting light into chamber 303 and detecting light emitted into chamber 303 by each of the other ones of LS 340a-340d (e.g., LS 340a may detect a backscattered portion of light emitted from LS 340c, LS 340b may detect a forward scattered portion of light emitted from LS 340c, and LS 340d may detect an obscuration portion of light emitted from LS 340c, while LS 340b may detect a backscattered portion of light emitted from LS 340d, LS 340a may detect a forward scattered portion of light emitted from LS 340d, and LS 340c may detect an obscuration portion of light emitted from LS 340d). Each one of LS 340a-340d may have different functional characteristics, different calibration power characteristic values, different calibration brightness values, different calibration temperature values, different associated correlator data, different temperature coefficient data, and/or the like, which may be associated with different portions of data 316d, and/or any light detecting subsystem of configuration 341 and circuitry and processing (e.g., on board 306) may be operative to function differently with respect to light being emitted by different light emitting subsystems of configuration 341.

When configuration 341 includes multiple light emitting subsystems, each light emitting subsystem may be operative to emit the same type of light (e.g., the same wavelength of light with the same brightness) or, any one of multiple light emitting subsystems may emit a different type of light than any other one of the multiple light emitting subsystems. For example, emitted light L1a_e and emitted light L1b_e may differ in any suitable way or ways, such as by wavelength, brightness, and the like. For example, light L1a_e emitted by LS 340a may be infrared light while light L1b_e emitted by LS 340b may be blue light, where the different types of light may each be detected by one or more light detecting subsystems of configuration (e.g., LS 340c may be operative to detect not only infrared light emitted by LS 340a but also blue light emitted by LS 340b (e.g., a single LDCL or LDC of LS 340c may be operative to detect different wavelengths of light or multiple LDCLs or LDCs of LS 340c may be provided to detect a respective wavelength)). As different types of light may be scattered by different types of particles (e.g., different types of smoke particles with different compositions (e.g., matter and/or color), such as smoke from burning wood versus smoke from burning metal) in different ways or by the same particle in different ways within space 303, configuration 341 with multiple light emitting subsystems and multiple light detecting subsystems may be operative to capture additional data that may be used by system 305 (e.g., processor 315) to determine a current hazard condition within space 303. For example, a particular type of smoke particle may deflect and/or obscurate emitted light of a first wavelength in a first manner and may deflect and/or obscurate emitted light of a second wavelength in a second manner (e.g., smaller particles may more deflect light of a shorter wavelength than light of a longer wavelength). By comparing the magnitude (e.g., the brightness, radiance, etc.) of two or more of obscuration light portion L2a_ob, backscattered light portion L2a_bs, and forward scattered light portion L2a_fs of emitted light L1a_e with the magnitude of two or more of obscuration light portion L2b_ob, backscattered light portion L2b_bs, and forward scattered light portion L2b_fs of emitted light L1b_e within a single cycle or within multiple cycles within a limited period of time along with any suitable correlator data or calibration data (e.g., data 316d), system 305 may be operative to determine more effectively certain characteristics about the current hazard condition within space 303 (e.g., the size and/or the color and/or the material composition (e.g., type) of smoke S), thereby enabling various algorithms to use the data to make more informed decisions when operating the hazard detection system.

Additionally or alternatively, although not shown, chamber space 303 of internal chamber body 302 may include other components in addition to smoke detecting components, such as an additional light emitting component and/or an additional light detecting component (e.g., ultra-violet light, spectroscopy, and/or the like) that may be used within chamber space 303 to detect the presence of pollen, a quality of the air, humidity, and the like. Such additional light emitting components and/or additional light detecting components could be used to help distinguish between smoke and a false alarm. In some embodiments, such additional light emitting components and/or additional light detecting components could be used as a particle counter or pollen counter to give an indication of general air quality. Information about the pollen count may be provided to an occupant or occupants of the home or structure, or recorded on a central database, to help individuals be aware of possible allergy issues. In other embodiments, the additional components within chamber space 303 may be used to determine if enclosure 300 is relatively humid, which may cause hazard detection system 305 to falsely trigger an alarm. If hazard detection system 305 determines that the humidity is relatively high, the sensitivity of the smoke detecting components may be reduced so as to reduce the occurrence of false alarms. In this manner, hazard detection system 305 may function as a multi-sensing unit. In other embodiments, additional components may be positioned at locations within hazard detection system 305 other than within chamber space 303.

Additional details of specific hazard detectors can be found, for example, in commonly assigned, co-pending U.S. Patent Application Publication No. 2015-0260581, filed on May 28, 2015, entitled "Selectable Lens Button For A Smart Home Device and Method Therefor," the disclosure of which is incorporated by reference herein its entirety.

Although system 305 has been described as a hazard detection system (e.g., for smoke by using light emitting subsystem 350 in combination with light detecting subsystem 380), it is to be understood that the concepts described herein may be utilized for system 305 as any suitable detection system, such as a proximity detection system or a nondispersive infrared (NDIR) sensing system or a display backlight brightness sensing system or any other suitable system that may use a light emitting subsystem in combination with a light detecting subsystem. A processing subsystem of system 305 may be any suitable components of system 305 that may receive, detect, manipulate, analyze, and/or otherwise use any information from one or more of LEC 352, TSLEC 360, DSLEC 370, LEC 352', TSLEC 360', DSLEC 370', LDC 382, and/or TSLDC 390, such as one, some, or all of LECC 354, circuitry 356, TSLECC 369, LDCLC 379, LECC 354', circuitry 356', TSLECC 369', LDCLC 379', LDCC 384, TSLDCC 399, processor 315, processor application 315a, processor data 316d, and memory 316 alone or in any combination.

Figure 5:
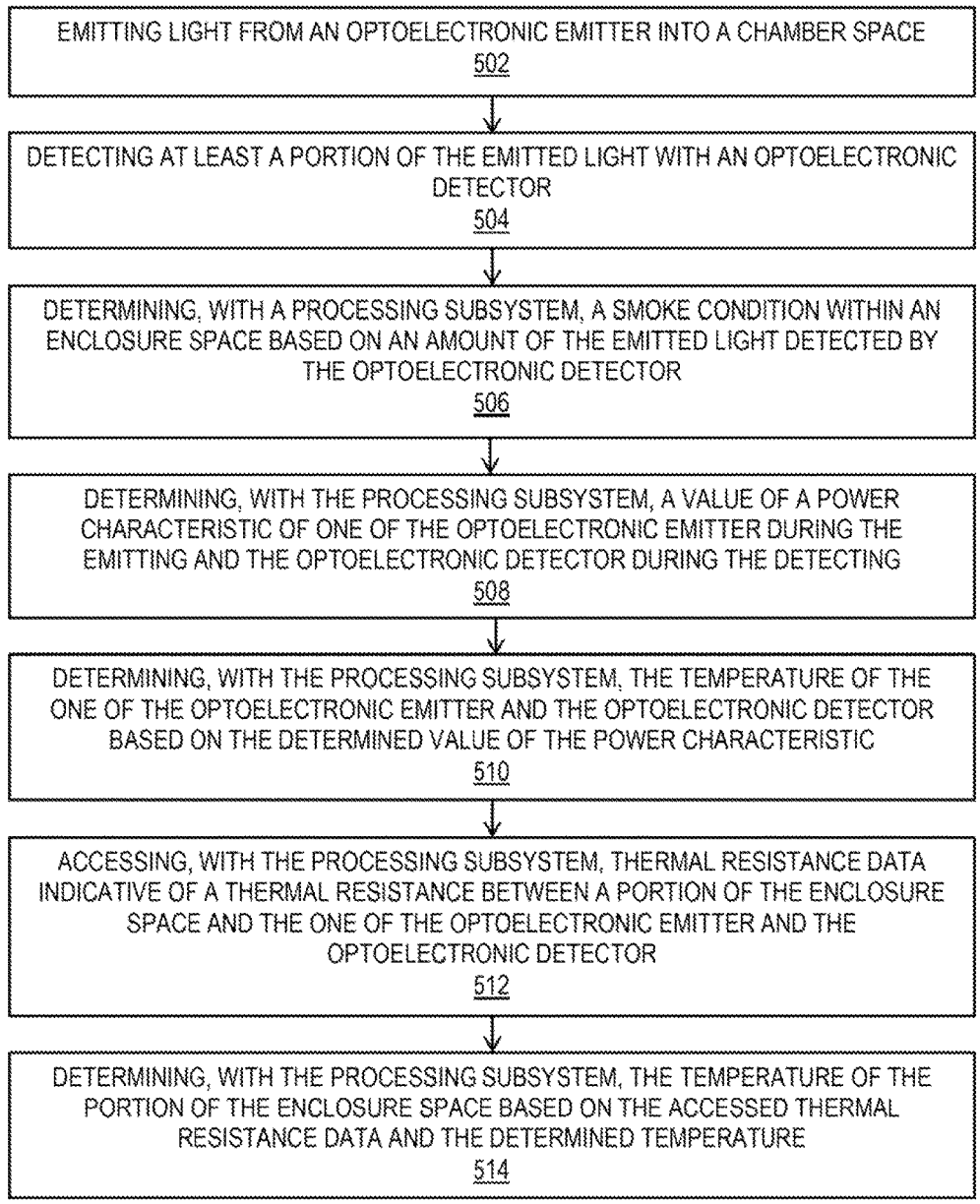

FIG. 5 is a flowchart of an illustrative process 500 for operating a hazard detection system that includes a chamber body defining a chamber space within an enclosure space, an optoelectronic emitter, an optoelectronic detector, and a processing subsystem. At step 502, process 500 may include emitting light from the optoelectronic emitter into the chamber space (e.g., LEC 352 may emit light L1 into space 303). At step 504, process 500 may include detecting at least a portion of the emitted light with the optoelectronic detector (e.g., LDC 382 may detect light L2). At step 506, process 500 may include determining, with the processing subsystem, a smoke condition within the enclosure space based on an amount of the emitted light detected by the optoelectronic detector (e.g., LDCC 384 and processor 315 and data 316d may be operative to determine a smoke condition within space 303 based on an amount of light L2 detected by LDC 382). At step 508, process 500 may include determining, with the processing subsystem, a value of a power characteristic of one of the optoelectronic emitter during the emitting and the optoelectronic detector during the detecting (e.g., LECC 354 and processor 315 may be operative to determine a forward voltage of light emitting element 351 of LEC 352). At step 510, process 500 may include determining, with the processing subsystem, the temperature of the one of the optoelectronic emitter and the optoelectronic detector based on the determined value of the power characteristic (e.g., processor 315 and data 316d may be operative to determine the temperature of LEC 352 based on the determined forward voltage of light emitting element 351). At step 512, process 500 may include accessing, with the processing subsystem, thermal resistance data indicative of a thermal resistance between a portion of the enclosure space and the one of the optoelectronic emitter and the optoelectronic detector (e.g., processor 315 and data 316d may be operative to access thermal resistance data indicative of a thermal resistance between LEC 352 and location N1 or N2 of space 301). At step 514, process 500 may include determining, with the processing subsystem, the temperature of the portion of the enclosure space based on the accessed thermal resistance data and the determined temperature (e.g., processor 315 may be operative to determine the temperature of location N1 or N2 based on the detected temperature of LEC 352 and the accessed thermal resistance between LEC 352 and location N1 or N2).

It is understood that the steps shown in process 500 of FIG. 5 are merely illustrative and that existing steps may be modified or omitted, additional steps may be added, and the order of certain steps may be altered.

FIG. 6 is a flowchart of an illustrative process 600 for operating an electronic device that includes a light emitting diode and a chamber body that at least partially defines a chamber space within an environment space. At step 602, process 600 may include detecting the magnitude of a forward voltage of the light emitting diode while the light emitting diode is emitting light into the chamber space for enabling the determination of a smoke condition within the environment space (e.g., while LED D of LEC 352 may be emitting light L1 into space 303 for enabling the determination of a smoke condition within space 301, LECC 354 and/or processor 315 may be operative to detect the magnitude of a forward voltage of LED D). At step 604, process 600 may include calculating the temperature of the light emitting diode using the detected magnitude of the forward voltage of the light emitting diode (e.g., processor 315 and data 316d may be operative to calculate the temperature $T_j$ of LED D using the detected magnitude of the forward voltage of LED D). At step 606, process 600 may include determining the temperature of a portion of the environment space that is external to the chamber space using the calculated temperature of the light emitting diode (e.g., processor 315 and data 316d may be operative to calculate the temperature of location N1 or N2 of space 301 using the calculated temperature $T_j$ of LED D).

It is understood that the steps shown in process 600 of FIG. 6 are merely illustrative and that existing steps may be modified or omitted, additional steps may be added, and the order of certain steps may be altered.

Figure 7:
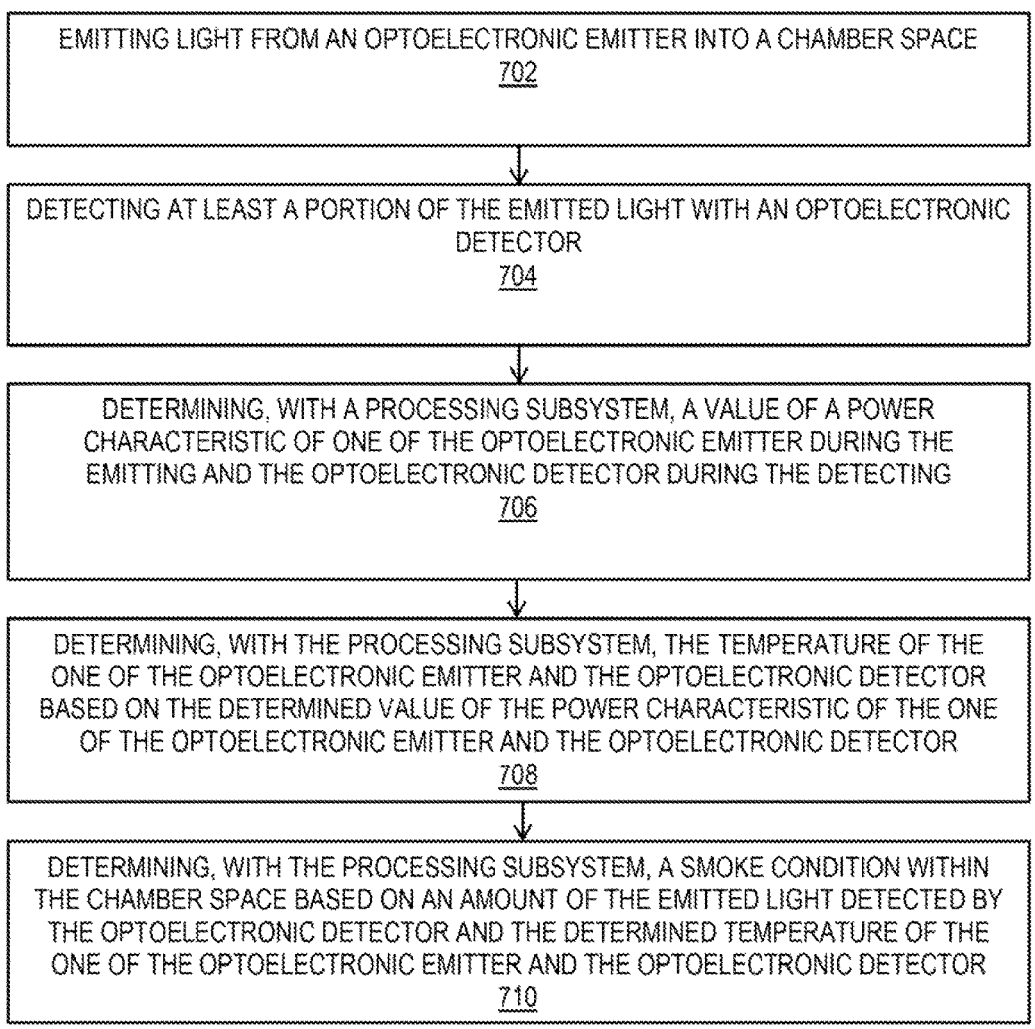

FIG. 7 is a flowchart of an illustrative process 700 for operating a hazard detection system that includes a chamber body defining a chamber space, an optoelectronic emitter, an optoelectronic detector, and a processing subsystem. At step 702, process 700 may include emitting light from the optoelectronic emitter into the chamber space (e.g., LEC 352 may be operative to emit light L1 into space 303). At step 704, process 700 may include detecting at least a portion of the emitted light with the optoelectronic detector (e.g., LDC 382 may be operative to detect light L2). At step 706, process 700 may include determining, with the processing subsystem, a value of a power characteristic of one of the optoelectronic emitter during the emitting and the optoelectronic detector during the detecting (e.g., LECC 354 and/or processor 315 may be operative to determine the value of the forward voltage of element 351 of LEC 352 while LEC 352 is emitting light L1 into space 303). At step 708, process 700 may include determining, with the processing subsystem, the temperature of the one of the optoelectronic emitter and the optoelectronic detector based on the determined value of the power characteristic of the one of the optoelectronic emitter and the optoelectronic detector (e.g., processor 315 and data 316d may be operative to determine the temperature of LEC 352 based on the determined value of the forward voltage of element 351 of LEC 352). At step 710, process 700 may include determining, with the processing subsystem, a smoke condition within the chamber space based on an amount of the emitted light detected by the optoelectronic detector and the determined temperature of the one of the optoelectronic emitter and the optoelectronic detector (e.g., LDCC 384 and processor 315 and data 316d may be operative to determine a smoke condition within space 303 based on an amount of light L2 detected by LDC 382 and the determined temperature of LEC 352).

It is understood that the steps shown in process 700 of FIG. 7 are merely illustrative and that existing steps may be modified or omitted, additional steps may be added, and the order of certain steps may be altered.

Figure 8:
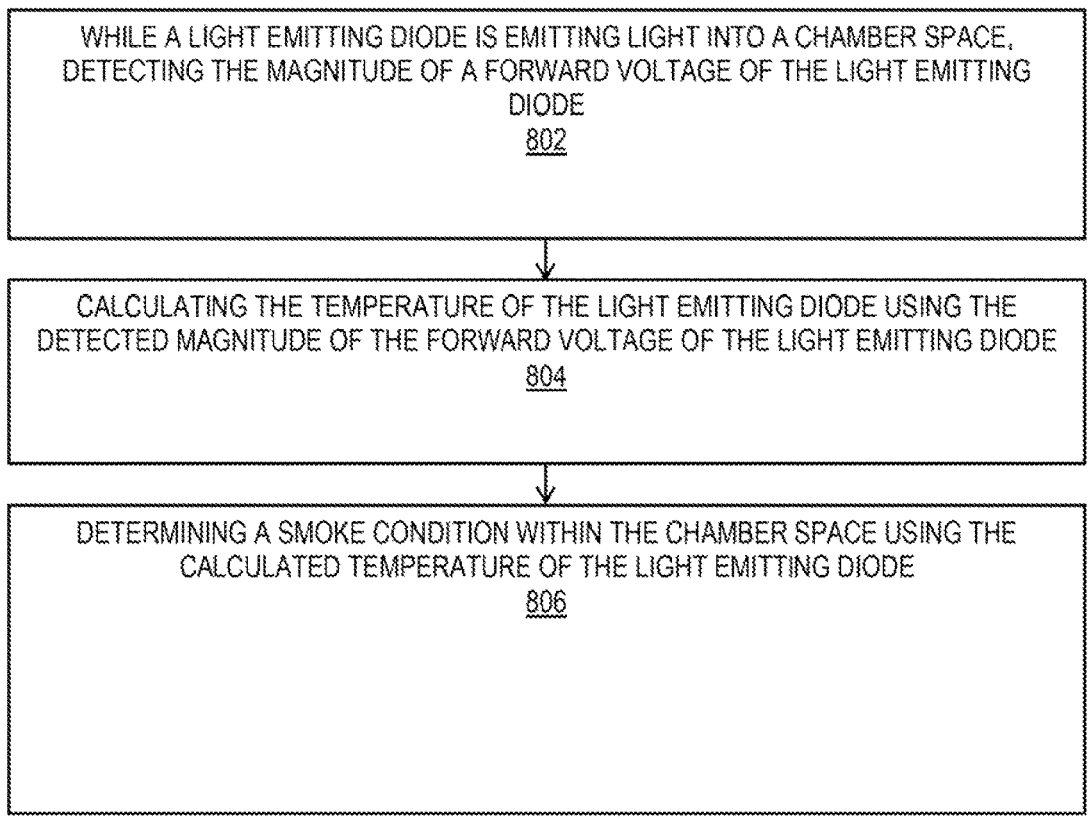

FIG. 8 is a flowchart of an illustrative process 800 for operating an electronic device that includes a light emitting diode and a chamber body that at least partially defines a chamber space. At step 802, process 800 may include detecting the magnitude of a forward voltage of the light emitting diode while the light emitting diode is emitting light into the chamber space (e.g., while LED D of LEC 352 may be emitting light L1 into space 303, LECC 354 and/or processor 315 may be operative to detect the magnitude of a forward voltage of LED D). At step 804, process 800 may include calculating the temperature of the light emitting diode using the detected magnitude of the forward voltage of the light emitting diode (e.g., processor 315 and data 316d may be operative to calculate the temperature $T_j$ of LED D using the detected magnitude of the forward voltage of LED D). At step 806, process 800 may include determining a smoke condition within the chamber space using the calculated temperature of the light emitting diode (e.g., LDCC 384 and processor 315 and data 316d may be operative to determine a smoke condition within space 303 using the calculated temperature $T_j$ of LED D).

It is understood that the steps shown in process 800 of FIG. 8 are merely illustrative and that existing steps may be modified or omitted, additional steps may be added, and the order of certain steps may be altered.

Figure 9:
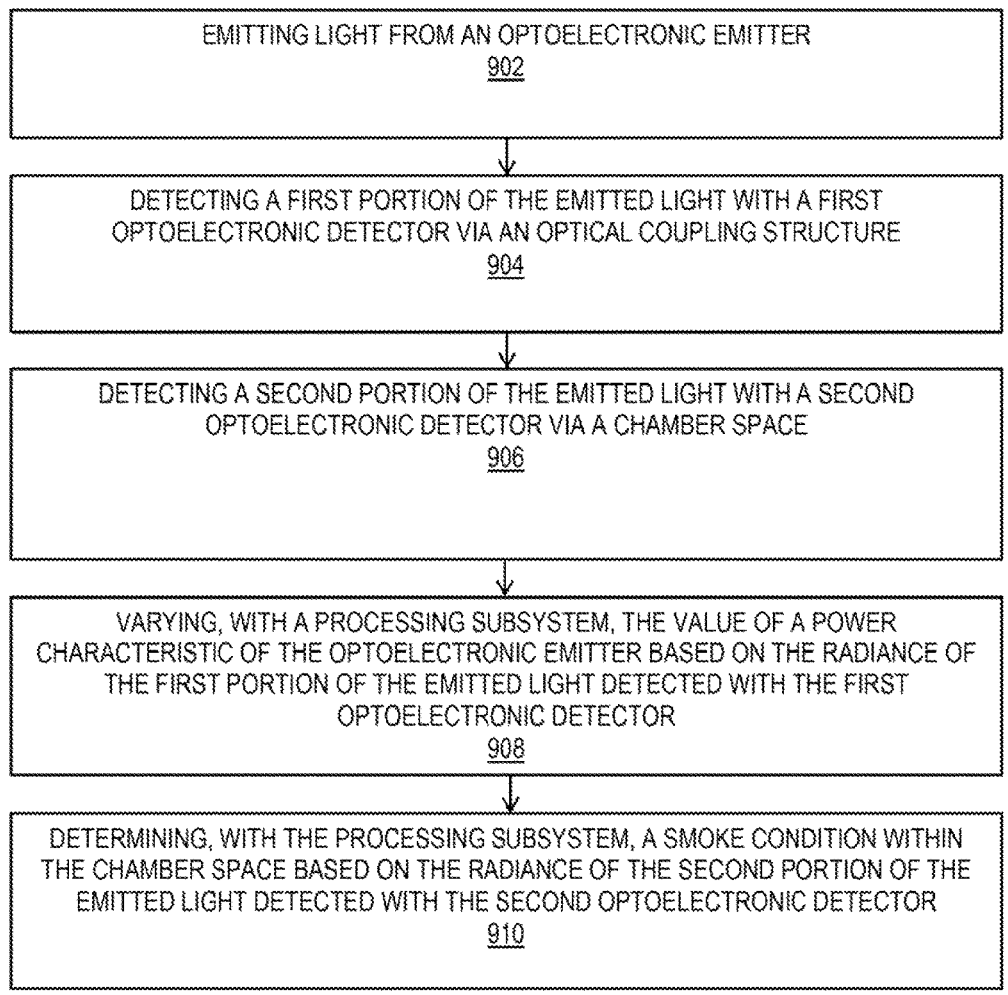

FIG. 9 is a flowchart of an illustrative process 900 for operating a hazard detection system that includes a chamber body defining a chamber space, an optoelectronic emitter, a first optoelectronic detector, a second optoelectronic detector, an optical coupling structure ensuring a light path between the optoelectronic emitter and the first optoelectronic detector, and a processing subsystem. At step 902, process 900 may include emitting light from the optoelectronic emitter (e.g., LEC 352 may be operative to emit light L1e). At step 904, process 900 may include detecting a first portion of the emitted light with the first optoelectronic detector via the optical coupling structure (e.g., LDCL 372 may be operative to detect light L1r or L1f of light L1e via optic coupling structure 359). At step 906, process 900 may include detecting a second portion of the emitted light with the second optoelectronic detector via the chamber space (e.g., LDC 382 may be operative to detect light L2 of light L1 of light L1e via space 303). At step 908, process 900 may include varying, with the processing subsystem, the value of a power characteristic of the optoelectronic emitter based on the radiance of the first portion of the emitted light detected with the first optoelectronic detector (e.g., processor 315 and/or data 316d and/or circuitry 356 may be operative to vary the magnitude of current injected into LEC 352 based on the radiance of light L1r or L1f of light L1e detected with LDCL 372). At step 910, process 900 may include determining, with the processing subsystem, a smoke condition within the chamber space based on the radiance of the second portion of the emitted light detected with the second optoelectronic detector (e.g., processor 315 and/or data 316d and/or circuitry 356 and/or LDCC 384 may be operative to determine a smoke condition within space 303 based on the radiance of light L2 detected with LDC 382).

It is understood that the steps shown in process 900 of FIG. 9 are merely illustrative and that existing steps may be modified or omitted, additional steps may be added, and the order of certain steps may be altered.

Figure 10:
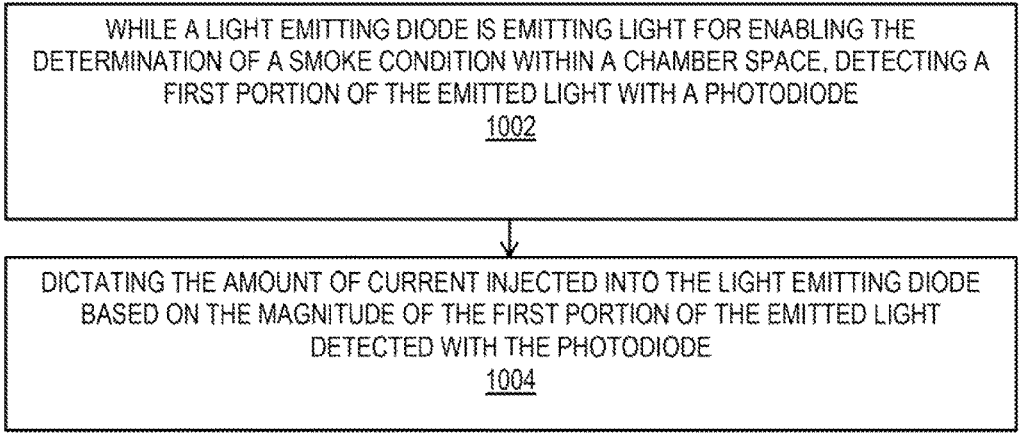

FIG. 10 is a flowchart of an illustrative process 1000 for operating an electronic device that includes a chamber body that at least partially defines a chamber space, a light emitting diode, and a photodiode. At step 1002, process 1000 may include detecting with the photodiode a first portion of light emitted by the light emitting diode while the light emitting diode is emitting the light for enabling the determination of a smoke condition within the chamber space (e.g., while LED D of LEC 352 may be emitting light L1e for enabling the determination of a smoke condition within space 303, a photodiode of LDCL 372 may be operative to detect light L1r or L1f of light L1e). At step 1004, process 1000 may include dictating the amount of current injected into the light emitting diode based on the magnitude of the first portion of the emitted light detected with the photodiode (e.g., processor 315 and/or data 316d and/or circuitry 356 may be operative to dictate the amount of current injected into LED D of LEC 352 based on the magnitude of light L1r or L1f detected by LDCL 372).

It is understood that the steps shown in process 1000 of FIG. 10 are merely illustrative and that existing steps may be modified or omitted, additional steps may be added, and the order of certain steps may be altered.

Figure 11:
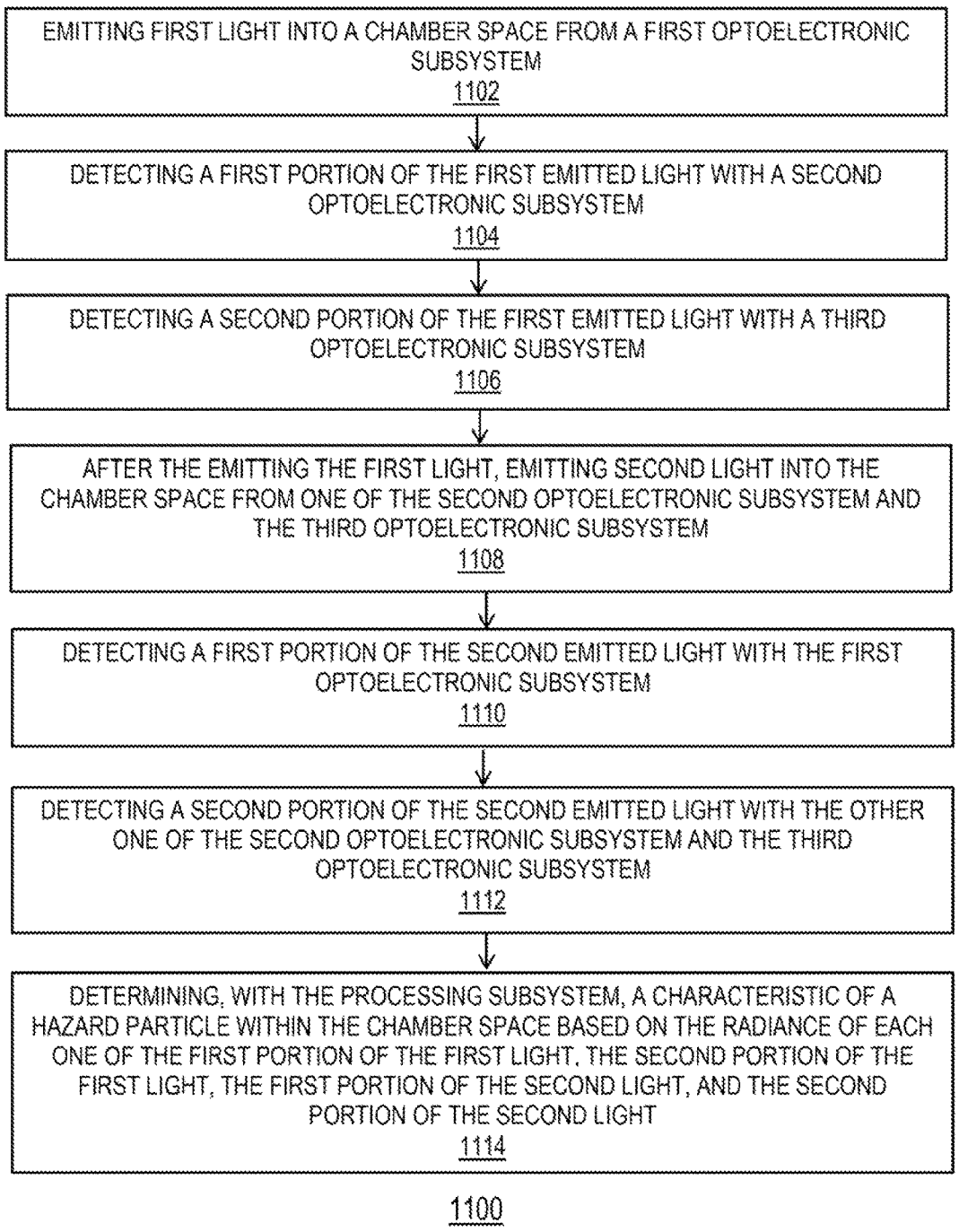

FIG. 11 is a flowchart of an illustrative process 1100 for operating an electronic device that includes a chamber body that at least partially defines a chamber space, a first optoelectronic subsystem, a second optoelectronic subsystem, a third optoelectronic subsystem, and a processing subsystem. At step 1102, process 1100 may include emitting first light into the chamber space from the first optoelectronic subsystem (e.g., light L1a_e may be emitted into space 303 from LS 340a). At step 1104, process 1100 may include detecting a first portion of the first emitted light with the second optoelectronic subsystem (e.g., light L2a_ob of light L1a_e may be detected by LS 340b). At step 1106, process 1100 may include detecting a second portion of the first emitted light with the third optoelectronic subsystem (e.g., light L2a_fs of light L1a_e may be detected by LS 340d). At step 1108, after the emitting of step 1102, process 1100 may include emitting second light into the chamber space from one of the second optoelectronic subsystem and the third optoelectronic subsystem (e.g., light L1b_e may be emitted into space 303 from LS 340b). At step 1110, process 1100 may include detecting a first portion of the second emitted light with the first optoelectronic subsystem (e.g., light L2b_ob of light L1b_e may be detected by LS 340a). At step 1112, process 1100 may include detecting a second portion of the second emitted light with the other one of the second optoelectronic subsystem and the third optoelectronic subsystem (e.g., light L2b_bs of light L1b_e may be detected by LS 340d). At step 1114, process 1100 may include determining, with the processing subsystem, a characteristic of a hazard particle within the chamber space based on the radiance of each one of the first portion of the first light detected at step 1104, the second portion of the first light detected at step 1106, the first portion of the second light detected at step 1110, and the second portion of the second light detected at step 1112 (e.g., processor 315 and data 316d may be operative to compare the magnitude (e.g., the brightness, radiance, etc.) of two or more of obscuration light portion L2a_ob, backscattered light portion L2a_bs, and forward scattered light portion L2a_fs of emitted light L1a_e with the magnitude of two or more of obscuration light portion L2b_ob, backscattered light portion L2b_bs, and forward scattered light portion L2b_fs of emitted light L1b_e to determine certain characteristics about the current hazard condition within space 303 (e.g., the size and/or the color and/or the material composition (e.g., type) of smoke particle S)).

It is understood that the steps shown in process 1100 of FIG. 11 are merely illustrative and that existing steps may be modified or omitted, additional steps may be added, and the order of certain steps may be altered.

Figure 12:
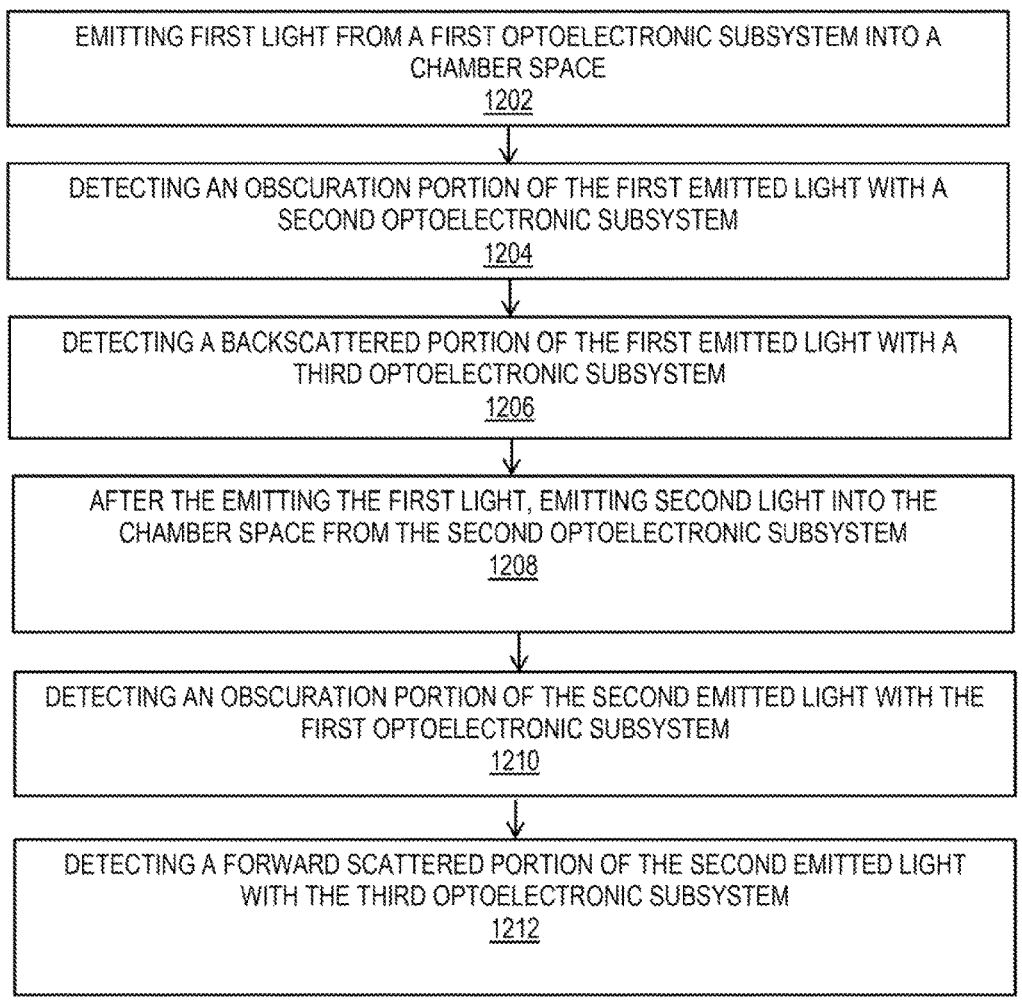

FIG. 12 is a flowchart of an illustrative process 1200 for operating an electronic device that includes a chamber body that at least partially defines a chamber space, a first optoelectronic subsystem, a second optoelectronic subsystem, and a third optoelectronic subsystem. At step 1202, process 1200 may include emitting first light into the chamber space from the first optoelectronic subsystem (e.g., light L1a_e may be emitted into space 303 from LS 340a). At step 1204, process 1200 may include detecting an obscuration portion of the first emitted light with the second optoelectronic subsystem (e.g., light L2a_ob of light L1a_e may be detected by LS 340b). At step 1206, process 1200 may include detecting a backscattered portion of the first emitted light with the third optoelectronic subsystem (e.g., light L2a_bs of light L1a_e may be detected by LS 340c). At step 1208, after the emitting of step 1202, process 1200 may include emitting second light into the chamber space from the second optoelectronic subsystem (e.g., light L1b_e may be emitted into space 303 from LS 340b). At step 1210, process 1200 may include detecting an obscuration portion of the second emitted light with the first optoelectronic subsystem (e.g., light L2b_ob of light L1b_e may be detected by LS 340a). At step 1212, process 1200 may include detecting a forward scattered portion of the second emitted light with the third optoelectronic subsystem (e.g., light L2b_fs of light L1b_e may be detected by LS 340c).

It is understood that the steps shown in process 1200 of FIG. 12 are merely illustrative and that existing steps may be modified or omitted, additional steps may be added, and the order of certain steps may be altered.

Figure 13:
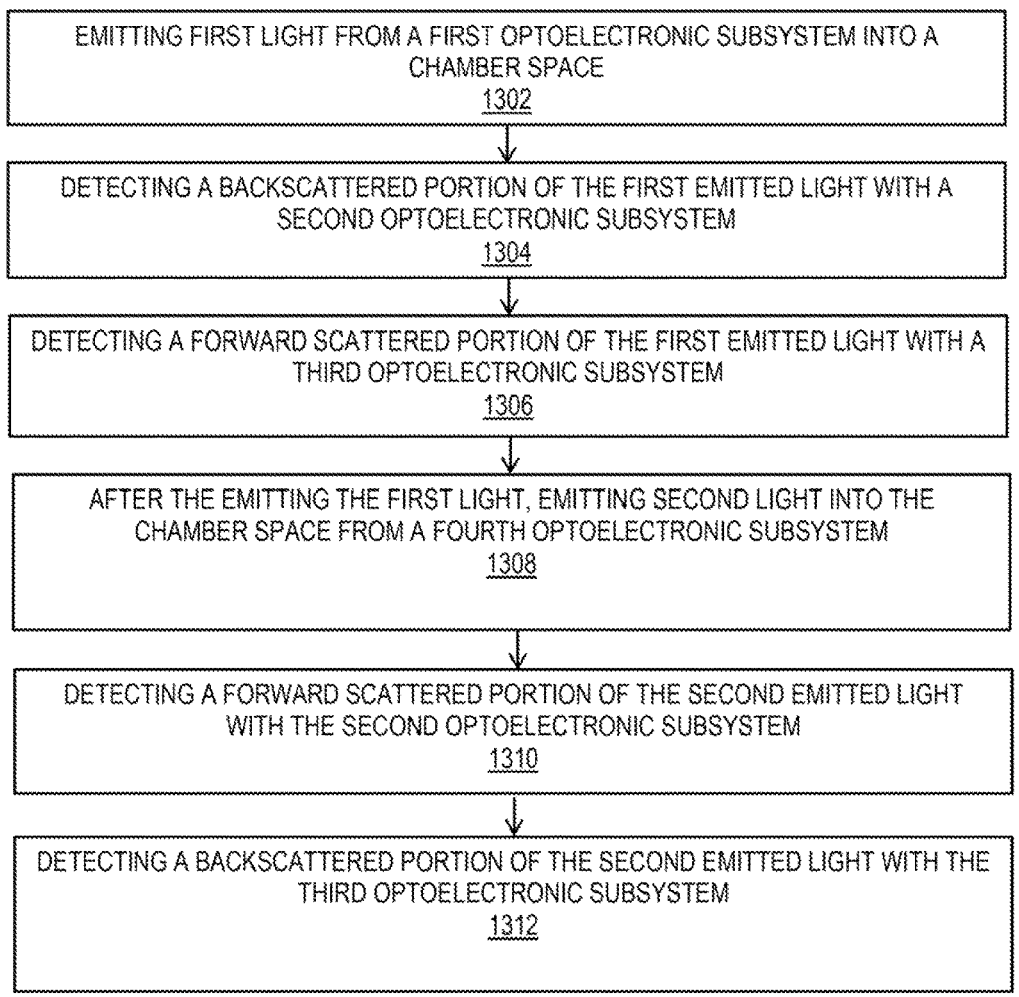

FIG. 13 is a flowchart of an illustrative process 1300 for operating an electronic device that includes a chamber body that at least partially defines a chamber space, a first optoelectronic subsystem, a second optoelectronic subsystem, a third optoelectronic subsystem, and a fourth optoelectronic subsystem. At step 1302, process 1300 may include emitting first light into the chamber space from the first optoelectronic subsystem (e.g., light L1a_e may be emitted into space 303 from LS 340a). At step 1304, process 1300 may include detecting a backscattered portion of the first emitted light with the second optoelectronic subsystem (e.g., light L2a_bs of light L1a_e may be detected by LS 340c). At step 1306, process 1300 may include detecting a forward scattered portion of the first emitted light with the third optoelectronic subsystem (e.g., light L2a_fs of light L1a_e may be detected by LS 340d). At step 1308, after the emitting of step 1302, process 1300 may include emitting second light into the chamber space from the fourth optoelectronic subsystem (e.g., light L1b_e may be emitted into space 303 from LS 340b). At step 1310, process 1300 may include detecting a forward scattered portion of the second emitted light with the second optoelectronic subsystem (e.g., light L2b_fs of light L1b_e may be detected by LS 340c). At step 1312, process 1300 may include detecting a backscattered portion of the second emitted light with the third optoelectronic subsystem (e.g., light L2b_bs of light L1b_e may be detected by LS 340d).

It is understood that the steps shown in process 1300 of FIG. 13 are merely illustrative and that existing steps may be modified or omitted, additional steps may be added, and the order of certain steps may be altered.

Any processes described with respect to FIGS. 1-13, as well as any other aspects of the disclosure, may each be implemented by software, but may also be implemented in hardware, firmware, or any combination of software, hardware, and firmware. They each may also be embodied as machine- or computer-readable code recorded on a machine- or computer-readable medium. The computer-readable medium may be any data storage device that can store data or instructions that can thereafter be read by a computer system. Examples of the computer-readable medium may include, but are not limited to, read-only memory, random-access memory, flash memory, CD-ROMs, DVDs, magnetic tape, and optical data storage devices. The computer-readable medium can also be distributed over network-coupled computer systems so that the computer-readable code may be stored and executed in a distributed fashion. For example, the computer-readable medium may be communicated from one electronic subsystem or device to another electronic subsystem or device using any suitable communications protocol. The computer-readable medium may embody computer-readable code, instructions, data structures, program modules, or other data in a modulated data signal, such as a carrier wave or other transport mechanism, and may include any information delivery media. A modulated data signal may be a signal that has one or more of its characteristics set or changed in such a manner as to encode information in the signal. Program modules, program components, and/or programmatic objects may include computer-readable and/or computer-executable instructions of and/or corresponding to any suitable computer programming language. In at least one embodiment, a computer-readable medium may be tangible. In at least one embodiment, a computer-readable medium may be non-transitory in time. Based on the disclosure and teachings provided herein, a person of ordinary skill in the art will appreciate other ways and/or methods to implement the various embodiments.

It is to be understood that any or each portion of any process discussed herein may be provided as a software construct, firmware construct, one or more hardware components, or a combination thereof. For example, any or each portion of any process discussed herein may be described in the general context of computer-executable instructions, such as program modules, that may be executed by one or more computers or other devices. Generally, a program module may include one or more routines, programs, objects, components, and/or data structures that may perform one or more particular tasks and/or that may implement one or more particular abstract data types.

Each one of the terms "computer-readable medium" or "machine-readable medium" may include, but is not limited to portable or fixed storage devices, optical storage devices, wireless channels and/or various other mediums that may be capable of storing, containing, and/or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, and/or the like may be passed, forwarded, or transmitted via any suitable technique, including, but not limited to, memory sharing, message passing, token passing, network transmission, and/or the like.

Furthermore, embodiments of the disclosure may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine-readable medium. One or more processors may perform the necessary tasks.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, and/or the like. When a process corresponds to a function, its termination may correspond to a return of the function to the calling function or the main function.

Any machine-readable medium tangibly embodying instructions may be used in implementing the methodologies described herein. For example, software codes may be stored in a memory. Memory may be implemented within the processor or external to the processor. As used herein the term "memory" may refer to any type of long term, short term, volatile, non-volatile, or other storage medium and is not to be limited to any particular type of memory or number of memories, or type of media upon which memory is stored.

Moreover, as disclosed herein, the term "storage medium" may represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" may include, but is not limited to portable or fixed storage devices, optical storage devices, wireless channels, and/or various other storage mediums capable of storing that contain or carry instruction(s) and/or data.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

Also, the words "comprise," "comprising," "include," "including," and "includes" when used in this specification and in the following claims are intended to specify the presence of stated features, intergers, components, or steps, but they do not preclude the presence or addition of one or more other features, integers, components, steps, acts, or groups.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Therefore, reference to the details of any preferred embodiments is not intended to limit their scope.

What is claimed is:

1. A hazard detection system comprising:
   a chamber body defining a chamber space;
   a light emitting diode operative to emit light with an emitted magnitude;
   a first light detecting diode;
   an optical coupling structure operative to:
      enable a first portion of the emitted light with a detected magnitude to be detected by the first light detecting diode;
      enable a second portion of the emitted light to be emitted into the chamber space; and
      maintain a constant ratio between the value of the emitted magnitude and the value of the detected magnitude despite variation in the value of the emitted magnitude;
   a second light detecting diode operative to detect the second portion of the emitted light; and
   a processing subsystem operative to:
      determine the current value of the detected magnitude based on the current value of a power characteristic of the first light detecting diode;
      compare the determined current value of the detected magnitude with a particular value;
      dictate the value of a power characteristic of the light emitting diode based on the comparison; and
      determine a current particular smoke condition within the chamber space based on the current amount of the second portion of the emitted light detected by the second light detecting diode.

2. The hazard detection system of claim 1, wherein the processing subsystem is operative to dictate the value of the power characteristic of the light emitting diode based on the comparison for maintaining the value of the emitted magnitude at another particular value.

3. The hazard detection system of claim 2, wherein the power characteristic of the light emitting diode is a current flowing through the light emitting diode.

4. The hazard detection system of claim 1, wherein the processing subsystem comprises analog feedback circuitry that is operative to:
   determine the current value of the detected magnitude based on the current value of the power characteristic of the first light detecting diode;
   compare the determined current value of the detected magnitude with the particular value; and
   dictate the value of the power characteristic of the light emitting diode based on the comparison.

5. The hazard detection system of claim 1, further comprising a die, wherein:
   the light emitting diode is provided on the die; and
   the first light detecting diode is provided on the die.

6. The hazard detection system of claim 1, further comprising:
   a package;
   a first die provided on the package; and
   a second die provided on the package, wherein:
      the light emitting diode is provided on the first die; and
      the first light detecting diode is provided on the second die.

7. The hazard detection system of claim 6, wherein:
   the optical coupling structure comprises a lens;
   the light emitting diode is operative to emit the light within the lens; and
   the first light detecting diode is operative to detect the first portion of the emitted light within the lens.

8. The hazard detection system of claim 1, wherein:
   the optical coupling structure comprises:
      a first lens;
      a second lens; and
      a light guide extending between the first lens and the second lens;
   the light emitting diode is operative to emit the light within the first lens;
   the light guide is operative to pass the first portion of the emitted light from the first lens to the second lens; and
   the first light detecting diode is operative to detect the first portion of the emitted light within the second lens.

9. The hazard detection system of claim 8, wherein the first light detecting diode is positioned outside of the chamber space.

10. The hazard detection system of claim 1, wherein the processing subsystem is operative to:
    determine the current temperature of the first light detecting diode; and
    determine the current particular smoke condition within the chamber space based on:
       the current amount of the second portion of the emitted light detected by the second light detecting diode; and
       the determined current temperature of the first light detecting diode.

11. The hazard detection system of claim 1, wherein the processing subsystem is operative to:
    determine the current temperature of the first light detecting diode;

access a temperature gain coefficient of the first light detecting diode; and determine the current particular smoke condition within the chamber space based on:
the current amount of the second portion of the emitted light detected by the second light detecting diode;
the determined current temperature of the first light detecting diode; and
the accessed temperature gain coefficient of the first light detecting diode.

12. The hazard detection system of claim 1, wherein the processing subsystem is operative to:
determine the current temperature of the first light detecting diode;
determine the current temperature of the second light detecting diode;
access a temperature gain coefficient of the first light detecting diode;
access a temperature gain coefficient of the second light detecting diode; and
determine the current particular smoke condition within the chamber space based on:
the current amount of the second portion of the emitted light detected by the second light detecting diode;
the determined current temperature of the first light detecting diode;
the determined current temperature of the second light detecting diode;
the accessed temperature gain coefficient of the first light detecting diode; and
the accessed temperature gain coefficient of the second light detecting diode.

13. The hazard detection system of claim 1, wherein the processing subsystem is operative to prevent a change in the temperature of the light emitting diode from affecting the value of the emitted magnitude.

14. A method for operating a hazard detection system, wherein the hazard detection system comprises a chamber body defining a chamber space, an optoelectronic emitter, a first optoelectronic detector, a second optoelectronic detector, an optical coupling structure ensuring a light path between the optoelectronic emitter and the first optoelectronic detector, and a processing subsystem, the method comprising:
emitting light from the optoelectronic emitter;
detecting a first portion of the emitted light with the first optoelectronic detector via the optical coupling structure;
detecting a second portion of the emitted light with the second optoelectronic detector via the chamber space;
varying, with the processing subsystem, the value of a power characteristic of the optoelectronic emitter based on the radiance of the first portion of the emitted light detected with the first optoelectronic detector; and
determining, with the processing subsystem, a smoke condition within the chamber space based on the radiance of the second portion of the emitted light detected with the second optoelectronic detector.

15. The method of claim 14, wherein the varying prevents a change in the temperature of the optoelectronic emitter from affecting the radiance of the light emitted from the optoelectronic emitter.

16. The method of claim 14, further comprising:
determining, with the processing subsystem, the temperature of the first optoelectronic detector; and
accessing, with the processing subsystem, a temperature gain coefficient of the first optoelectronic detector, wherein the determining the smoke condition within the chamber space comprises determining the smoke condition within the chamber space based on:
the radiance of the second portion of the emitted light detected with the second optoelectronic detector;
the determined temperature of the first optoelectronic detector; and
the accessed temperature gain coefficient of the first optoelectronic detector.

17. The method of claim 16, further comprising:
determining, with the processing subsystem, the temperature of the second optoelectronic detector; and
accessing, with the processing subsystem, a temperature gain coefficient of the second optoelectronic detector, wherein the determining the smoke condition within the chamber space comprises determining the smoke condition within the chamber space based on:
the radiance of the second portion of the emitted light detected with the second optoelectronic detector;
the determined temperature of the first optoelectronic detector;
the accessed temperature gain coefficient of the first optoelectronic detector;
the determined temperature of the second optoelectronic detector; and
the accessed temperature gain coefficient of the second optoelectronic detector.

18. The method of claim 16, wherein:
the method further comprises, during the detecting the first portion of the emitted light with the first optoelectronic detector via the optical coupling structure, determining, with the processing subsystem, a value of a power characteristic of the first optoelectronic detector; and
the determining the temperature of the first optoelectronic detector comprises determining the temperature of the first optoelectronic detector based on the determined value of the power characteristic of the first optoelectronic detector.

19. The method of claim 18, wherein the determining the temperature of the first optoelectronic detector comprises:
accessing, with the processing subsystem, correlator data indicative of another value of the power characteristic of the first optoelectronic detector at another temperature of the first optoelectronic detector; and
estimating, with the processing subsystem, the temperature of the first optoelectronic detector based on:
the determined value of the power characteristic of the first optoelectronic detector; and
the accessed correlator data.

20. A method for operating an electronic device, wherein the electronic device comprises a chamber body that at least partially defines a chamber space, a light emitting diode, and a photodiode, the method comprising:
while the light emitting diode is emitting light for enabling the determination of a smoke condition within the chamber space, detecting a first portion of the emitted light with the photodiode; and
dictating the amount of current injected into the light emitting diode based on the magnitude of the first portion of the emitted light detected with the photodiode.

* * * * *